United States Patent [19]
Miyamoto et al.

[11] Patent Number: 5,830,615
[45] Date of Patent: Nov. 3, 1998

[54] NAPHTHYLENEDIAMINE DERIVATIVE AND ELECTROPHOTOSENSITIVE MATERIAL USING THE SAME

[75] Inventors: Eiichi Miyamoto; Mikio Kakui; Hideo Nakamori; Yukikatsu Imanaka; Tadashi Sakuma; Maki Uchida; Hiroaki Iwasaki; Yasuyuki Hanatani; Nariaki Tanaka; Yuka Nakamura, all of Osaka, Japan

[73] Assignee: Mita Industrial Co., Ltd., Osaka, Japan

[21] Appl. No.: 865,196

[22] Filed: May 29, 1997

Related U.S. Application Data

[62] Division of Ser. No. 539,620, Oct. 5, 1995.

[30] Foreign Application Priority Data

Oct. 18, 1994 [JP] Japan .................................. 6-252399
Feb. 10, 1995 [JP] Japan .................................. 7-022572
Apr. 20, 1995 [JP] Japan .................................. 7-120688

[51] Int. Cl.⁶ .................................................. G03G 5/06
[52] U.S. Cl. .............................. 430/72; 430/56; 430/59; 430/73; 430/78
[58] Field of Search .............................. 430/56, 73, 78, 430/72, 59

[56] References Cited

U.S. PATENT DOCUMENTS 3,461,165  8/1969  Frye ................................. 564/429
4,666,810  5/1987  Umehara et al. ...................... 430/71

FOREIGN PATENT DOCUMENTS 0650955    5/1995   European Pat. Off. .
62-018566  1/1987   Japan .
03121889   5/1991   Japan .
A04118286  4/1992   Japan .
A05038877  2/1993   Japan .
05080550   4/1993   Japan .

*Primary Examiner*—Richard L. Raymond
*Attorney, Agent, or Firm*—Beveridge, Degrandi Weilacher & Young, LLP

[57] ABSTRACT

The present invention provides a novel naphthylenediamine derivative which is superior in electric charge transferring capability, compatibility with binding resin and stability, and an electrophotosensitive material which has a higher sensitivity and an excellent durability. The above naphthylenediamine derivative is represented by the following general formula (1), and the electrophotosensitive material is formed by providing a photosensitive layer having this naphthylenediamine derivative as an electric charge transferring material on a conductive substrate.

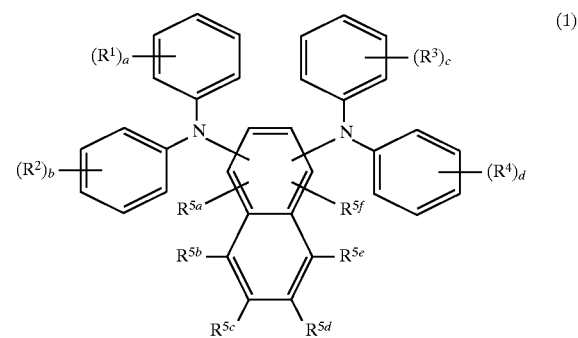

wherein $R^1$ to $R^4$, $R^{5a}$ to $R^{5f}$ and a to d are as defined.

12 Claims, 2 Drawing Sheets

NAPHTHYLENEDIAMINE DERIVATIVE AND ELECTROPHOTOSENSITIVE MATERIAL USING THE SAME

This is a divisional of co-pending application Ser. No. 08/539,620 filed on Oct. 5, 1995.

BACKGROUND OF THE INVENTION

The present invention relates to a novel naphthylenediamine derivative which is suitably used as an electric charge transferring material, particularly hole transferring material in applications such as solar battery, electroluminescent device, electrophotosensitive material, etc., and an electrophotosensitive material using the same, which is used for image forming apparatuses such as electrostatic copying machine, laser beam printer, etc.

As the electric charge transferring material to be used for the above applications, there have been known various organic compounds such as carbazole compound, oxadiazole compound, pyrazoline compound, hydrazone compound, stilbene compound, phenylenediamine compound, benzidine compound, etc.

These electric charge transferring materials are normally used in a state where they are dispersed in a membrane of a suitable binding resin. In case of electrophotoconductor, for example, so-called organic photoconductor (OPC) such as single-layer type photoconductor comprising a single-layer type photosensitive layer wherein the above electric charge transferring material and an electric charge generating material which generates an electric charge due to light irradiation are dispersed in a binding resin, multi-layer type photoconductor comprising an electric charge transferring layer containing the above electric transferring material and an electric charge generating layer containing an electric charge generating material, etc. are normally used.

Such an organic photoconductor has an advantage that it is easily produced in comparison with an inorganic photoconductor using an inorganic semi-conductor material and can select its material from electric charge generating material, electric charge transferring material, binding resin, etc., thereby offering a great degree of freedom for design of performance.

Typical examples of the electric charge transferring material include an m-phenylenediamine derivative represented by the general formula (71):

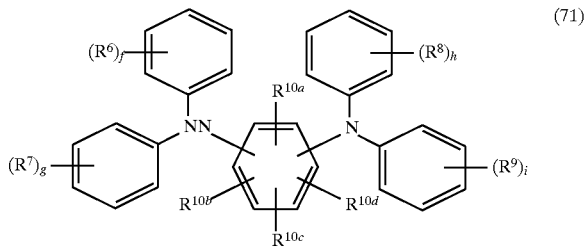

wherein $R^6$, $R^7$, $R^8$ and $R^9$ are same or different and indicate a hydrogen atom, a halogen atom, an alkyl group which may contain a substituent, an alkoxy group which may contain a substituent or an aryl group which may contain a substituent; $R^{10a}$, $R^{10b}$, $R^{10c}$ and $R^{10d}$ are same or different and indicate a hydrogen atom, a halogen atom, a cyano group, a nitro group, an alkyl group which may contain a substituent, an alkoxy group which may contain a substituent or an aryl group which may contain a substituent; and f, g, h and i are the same or different and indicate an integer of 1 to 5.

The above m-phenylenediamine derivative is superior in compatibility with binding resin and also superior in electric charge transferring capability. However, the m-phenylenediamine derivative has a problem that it is insufficient in stability and is liable to be deteriorated or decomposed when it changed into a singlet excited state where a reactivity is high due to light irradiation.

The reason is that electrons at a HOMO (Highest Occupied Molecular Orbital) level, which have relation to transferring of holes, are localized on carbons at the 4- and 6-positions of the benzene ring, which constitute a center skeleton of the molecule, thereby increasing a chemical reactivity of these positions.

Therefore, the electrophotosensitive material using the above m-phenylenediamine derivative as the electric charge transferring material has a problem that the m-phenylenediamine derivative causes a photochemical reaction in case of repeating processes of charging, exposure and discharging to form a deteriorated substance, which causes the deterioration of sensitivity and increase in charging, which results in insufficient durability.

SUMMARY OF THE INVENTION

It is a main object of the present invention is to provide a novel electric charge transferring material which is superior in electric charge transferring capability, compatibility with binding resin and stability.

It is another object of the present invention to provide an electrophotosensitive material using the above electric charge transferring material, which has a high sensitivity and an excellent durability.

The present inventors have studied to improve the stability of the material by introducing a naphthalene ring having a quenching effect, i.e. effect of accelerating deactivation from a photoexcited state in place of a benzene ring constituting a center skeleton of the above phenylenediamine derivative, and then carried out a molecular designing of the naphthylenediamine derivative as a novel compound.

As a result, it has been found that, when two 6-membered rings constituting the naphthalene ring are respectively substituted with one nitrogen atom, the resulting derivative is inferior in compatibility with binding resin because a symmetry of the molecule is high and, furthermore, the resulting derivative has low electric charge transferring capability, resulting in being unsuitable for practical use.

Therefore, the present inventors have further studied about the position where naphthalene rings are substituted with two nitrogen atoms. As a result, it has been found that a naphthylenediamine derivative represented by the general formula (1):

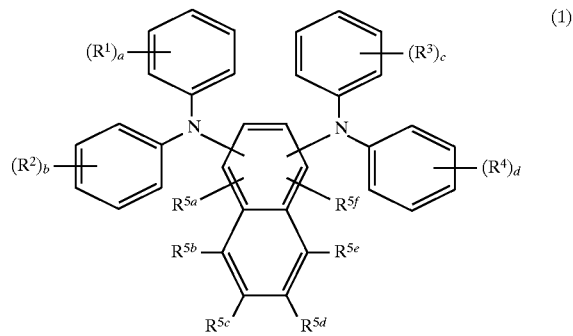

wherein $R^1$, $R^2$, $R^3$ and $R^4$ are same or different and indicate a hydrogen atom, a halogen atom, an alkyl group which may have a substituent, an alkoxy group which may have a substituent or an aryl group which may have a substituent; $R^{5a}$, $R^{5b}$, $R^{5c}$, $R^{5d}$, $R^{5e}$ and $R^{5f}$ are same or different and indicate a hydrogen atom, a halogen atom, a cyano group, a nitro group, an alkyl group which may have a substituent, an alkoxy group which may have a substituent or an aryl group which may have a substituent; and a, b, c and d, which respectively indicate substituting numbers of the groups $R^1$, $R^2$, $R^3$ and $R^4$, are the same or different and indicate an integer of 1 to 5, has the following features.

(1) Since an asymmetry of the molecule becomes higher, the compatibility with binding resin is the same as that of the m-phenylenediamine derivative or it becomes higher.

(2) Regarding the above naphthylenediamine derivative, electrons at the HOMO level, which have relation to transfer of holes, are non-localized to spread through the molecule because of the following two main factors:

① four phenyl groups substituted on the respective nitrogen atoms are located close each other, and ② electrons at the HOMO level in the center naphthalene ring are not localized like the benzene ring, and they are liable to spread through the ring, which results in non-localization. As a result, the mobility of the electric charge becomes better than that of the m-phenylenediamine derivative in cooperation with the fact that the naphthalene ring has a π electron conjugate system larger than that of the benzene ring. Therefore, the electric charge transferring capability is further improved.

(3) As described above, regarding the naphthylenediamine derivative wherein electrons at the HOMO level are non-localized, a stereoscopic distribution of electrons is in a plane. Therefore, when this naphthylenediamine derivative as the electric charge transferring material is contained in the photosensitive layer of the electrophotosensitive material, together with an electric charge generating material, an interaction with the electric charge generating material, i.e. action of drawing an electric charge (particularly, hole) generated in the electric charge generating material becomes strong to improve the electric charge generation efficiency of the electric charge generating material. As a result, the sensitivity of the photosensitive material is improved.

(4) As described above, the naphthylenediamine derivative wherein electrons at the HOMO level are non-localized has not a position where electrons are localized to enhance a chemical reactivity, like the center benzene ring in the m-phenylenediamine derivative. Therefore, the stability at the time of light irradiation becomes excellent in cooperation with the fact that the center naphthalene ring has a quenching effect as described above. Thus, the present invention has been accomplished.

That is, the naphthylenediamine derivative of the present invention is characterized by being represented by the above general formula (1).

Also, the electrophotosensitive material of the present invention is characterized by providing a photosensitive layer containing the above naphthylenediamine derivative (1) on a conductive substrate.

Furthermore, the present inventors have found that it becomes possible to impart a high sensitivity to the photosensitive material and to improve the durability thereof by containing at least one selected from the following compounds represented by the general formulas (2), (3), (4), (5) and (6).

2,4,7-trinitrofluorenonimine derivative represented by the general formula (2):

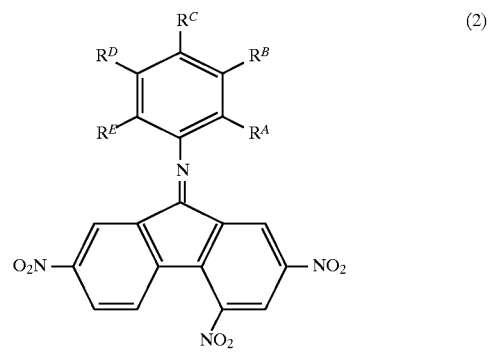

wherein $R^A$, $R^B$, $R^C$, $R^D$ and $R^E$ are same or different and indicate a hydrogen atom, a halogen atom, an alkyl group which may contain a substituent, an alkoxy group which may contain a substituent, an aryl group which may contain a substituent, an aralkyl group which may contain a substituent or a phenoxy group which may contain a substituent.

Diphenoquinone derivative represented by the general formula (3): 0 wherein $R^F$, $R^G$, $R^H$ and $R^I$ are same or different and indicate a hydrogen atom, an alkyl group which may contain a substituent, an alkoxy group which may contain a substituent, an aryl group which may contain a substituent or an aralkyl group which may contain a substituent.

Ethylated nitrofluorenonimine derivative represented by the general formula (4):

wherein $R^J$, $R^K$, $R^L$, $R^M$ and $R^N$ are same or different and indicate a hydrogen atom, a halogen atom, an alkyl group which may contain a substituent, an alkoxy group which may contain a substituent, an aryl group which may contain a substituent, an aralkyl group which may contain a substituent or a phenoxy group which may contain a substituent; and α is an integer of 1 to 4.

Tryptoanthrine derivative represented by the general formula (5):

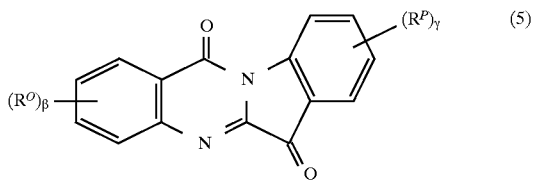

wherein $R^O$ and $R^P$ are same or different and indicate an alkyl group which may contain a substituent, an alkoxy group which may contain a substituent or a nitro group; and β and γ are the same or different and indicate an integer of 0 to 3.

Tryptoanthrinimine derivative represented by the general formula (6):

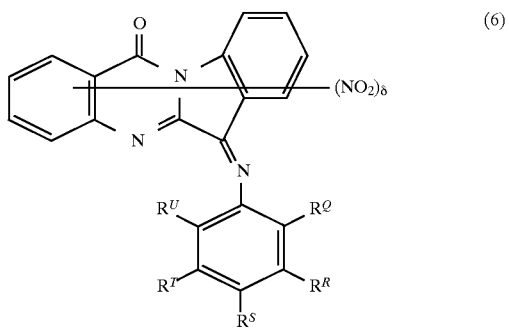

wherein $R^Q$, $R^R$, $R^S$, $R^T$ and $R^U$ are same or different and indicate a hydrogen atom, a halogen atom, an alkyl group which may contain a substituent, an alkoxy group which may contain a substituent, an aryl group which may contain a substituent, an aralkyl group which may contain a substituent or a phenoxy group which may contain a substituent; and δ is an integer of 1 to 4.

Another electrophotosensitive material of the present invention is characterized by providing a photosensitive layer containing the naphthylenediamine derivative (1) and 2,4,7-trinitrofluorenonimine derivative (2), a photosensitive layer containing the naphthylenediamine derivative (1) and diphenoquinone derivative (3), a photosensitive layer containing the naphthylenediamine derivative (1) and ethylated nitrofluorenonimine derivative (4), a photosensitive layer containing the naphthylenediamine derivative (1) and tryptoanthrine derivative (5) or a photosensitive layer containing the naphthylenediamine derivative (1) and tryptoanthrinimine derivative (6) on a conductive substrate.

Normally, when a hole transferring material and an electron transferring material are contained in the same layer, both materials forms a charge transfer complex to cause deterioration of the electric charge transferring capability of the whole photosensitive layer, which results in deterioration of the sensitivity of the photosensitive material.

However, in case of combination of the naphthylenediamine derivative (1) (hole transferring material) with the 2,4,7-trinitrofluorenonimine derivative (2), diphenoquinone derivative (3), ethylated nitrofluorenonimine derivative (4), tryptoanthrine derivative (5) or tryptoanthrinimine derivative (6), all of which are electron transferring materials, no charge transfer complex is formed in the layer even if both transferring materials are contained in a high concentration at which holes and electrons are efficiently transferred. Therefore, it shows such an unusual action that the hole transferring material and electron transferring material can efficiently transfer holes and electrons, respectively.

Therefore, the efficiency of electrons, which are remained as a trap of holes in the photosensitive layer, to be charged from the photosensitive layer is improved and the residual potential is lowered, thereby improving the sensitivity of the photoconductor. As described above, the generation of the trap is prevented so that an increase in charging (increase in surface potential and residual potential) is not generated when the image is repeatedly formed, and the durability of the photosensitive material is improved.

It also became apparent that a photosensitive material containing the naphthylenediamine derivative (1) and any one of the above five sorts of electron transferring materials has a specific action, i.e. particularly excellent light resistance to ultraviolet light.

That is, when ultraviolet light is irradiated to the photosensitive material, the naphthylenediamine derivative (1) becomes a singlet excited state where a reactivity is high, and is liable to be deteriorated or decomposed. However, when any one of the above five sorts of electron transferring materials is present in the same layer, these derivatives having excellent electron acceptive properties show a quenching effect, i.e. effect of accelerating deactivation from a photoexcited state. Therefore, deterioration of the material and formation of a radical are inhibited, thereby improving the light resistance.

Particularly, this effect is remarkably observed in the 2,4,7-trinitrofluorenonimine derivative (2), however, it is also observed in other four sorts of electron transferring materials. It is assumed that a specific chemical structure in the respective materials (e.g. imine skeleton, in case of 2,4,7-trinitrofluorenonimine derivative (2)) affords this effect, but a definite mechanism thereof has never been apparent.

Furthermore, the present inventors have found that it becomes possible to impart a higher sensitivity to the photosensitive material and to improve the durability thereof by blending a phenylenediamine derivative represented by the general formula (7):

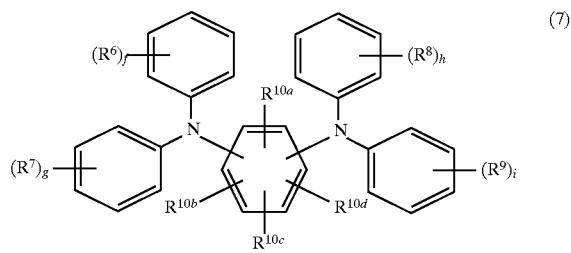

wherein $R^6$, $R^7$, $R^8$ and $R^9$ are same or different and indicate a hydrogen atom, a halogen atom, an alkyl group which may contain a substituent, an alkoxy group which may contain a substituent or an aryl group which may contain a substituent; $R^{10a}$, $R^{10b}$, $R^{10c}$ and $R^{10d}$ are same or different and indicate a hydrogen atom, a halogen atom, a cyano group, a nitro group, an alkyl group which may contain a substituent, an alkoxy group which may contain a substituent or an aryl group which may contain a substituent; and f, g, h and i are the same or different and indicate an integer of 1 to 5] including the above m-phenylenediamine derivative represented by the general formula (71) into a photosensitive layer containing the naphthylenediamine derivative (1), as is apparent from the Examples described hereinafter, although the mechanism is not apparent.

Also, the present inventors have found that it becomes possible to impart a further higher sensitivity to the photoconductor and to further improve the durability thereof by using the above combination system of the naphthylenediamine derivative (1) and phenylenediamine derivative (7) (both are hole transferring materials) in combination with any one of the above five sorts of electron transferring materials, because of the effect due to the above two sorts of hole transferring materials and effect due to the combination of the above-described hole transferring material and electron transferring material.

Accordingly, another electrophotosensitive material of the present invention is characterized by providing a photosensitive layer containing the naphthylenediamine derivative (1) and phenylenediamine derivative (7) and, if necessary, at least one of the above five sorts of electron transferring materials on a conductive substrate.

DETAILED EXPLANATION OF THE INVENTION

Figure 1:
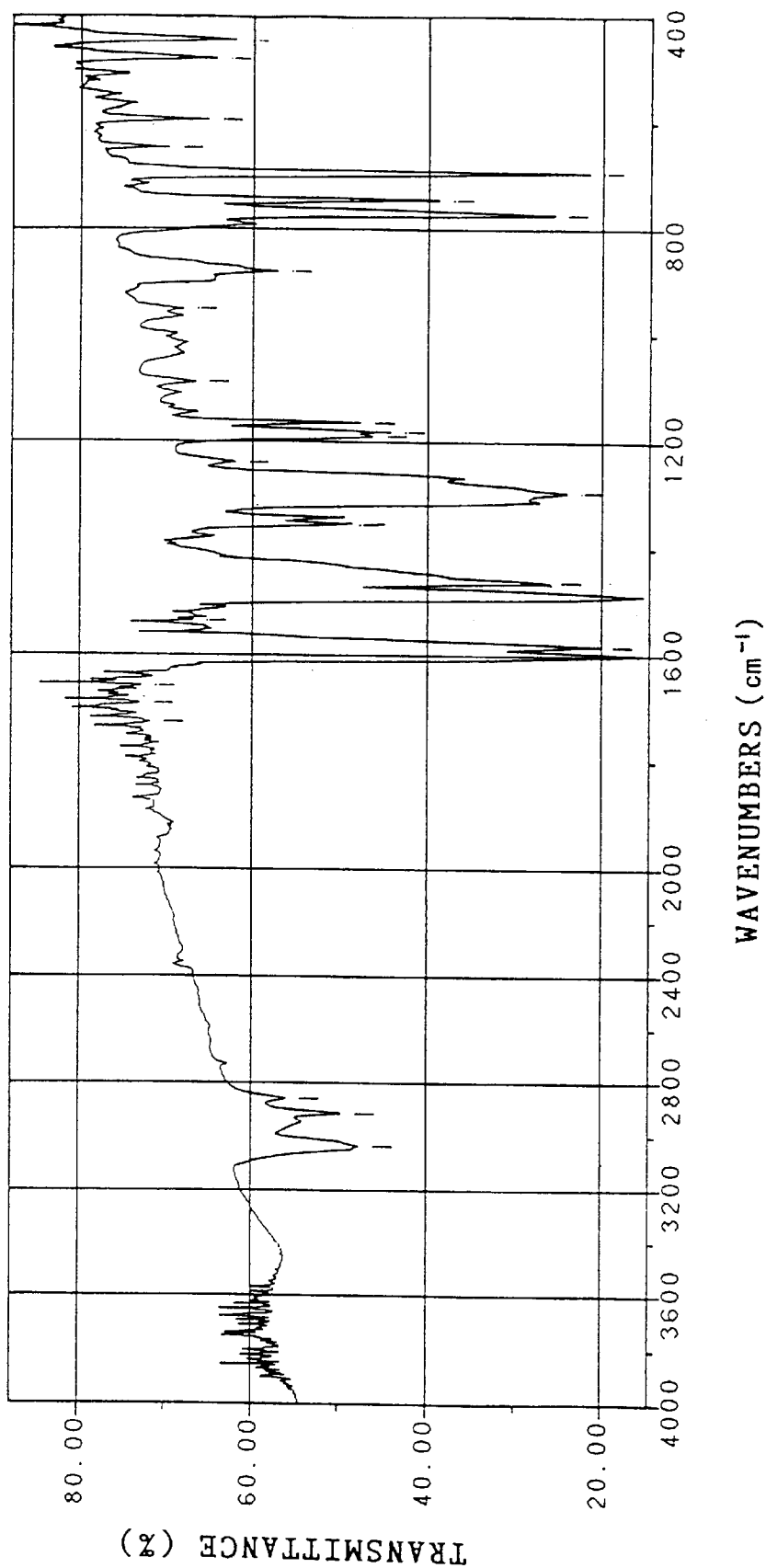
FIG. 1 is a graph illustrating the results of infrared spectroscopic analysis of the naphthylenediamine derivative of Example 1 according to the present invention.

Examples of the halogen atom corresponding to the groups $R^1$, $R^2$, $R^3$, $R^4$ and $R^{5a}$ to $R^{5f}$ in the above general formula (1) include fluorine atom, chlorine atom, bromine atom, iodine atom, etc.

Examples of the alkyl group include lower alkyl groups having 1 to 6 carbon atoms, such as methyl group, ethyl group, normal propyl group, isopropyl group, normal butyl group, isobutyl group, secondary butyl group, tertiary butyl group, pentyl group, hexyl group, etc.

Examples of the alkoxy group include lower alkoxy groups having 1 to 6 carbon atoms, such as methoxy group, ethoxy group, isopropoxy group, butoxy group, tertiary butoxy group, hexyloxy group, etc.

Examples of the aryl group include phenyl group, biphenyl group, naphthyl group, anthryl group, phenanthryl group, o-terphenyl group, etc.

Examples of the substituent with which the alkyl group, alkoxy group and aryl group may be substituted include the above alkyl group, halogen atom, alkoxy group, etc.

The naphthylenediamine derivative wherein the groups $R^1$ to $R^4$ and $R^{5a}$ to $R^{5e}$ indicate a hydrogen atom, simultaneously, is inferior in compatibility with binding resin in spite of the asymmetry of the above molecular structure. Therefore, it is preferred that the groups $R^1$ to $R^4$ and $R^{5a}$ to $R^{5e}$ do not indicate a hydrogen atom, simultaneously.

The substituting number of the groups $R^1$, $R^2$, $R^3$ and $R^4$ defined by the symbol a, b, c and d in the general formula (1) can be optionally selected within a range of 1 to 5, respectively.

In the naphthylenediamine derivative (1) of the present invention, the substitution position of two nitrogen atoms is limited to any one of two 6-membered rings constituting the napthalene ring, as described above. For example, four sorts such as 2,3-naphthylenediamine derivative represented by the general formula (11):

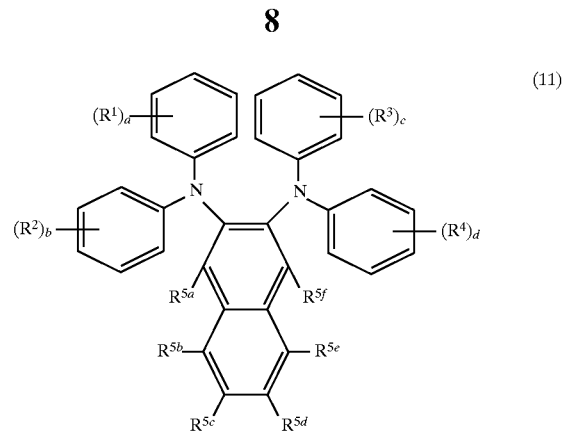

1,2-naphtylenediamine derivative represented by the general formula (12):

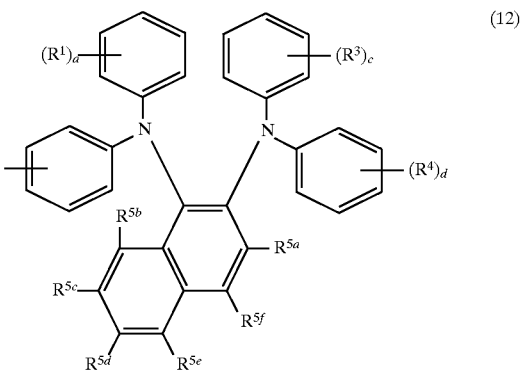

1,3-naphthylenediamine derivative represented by the general formula (13):

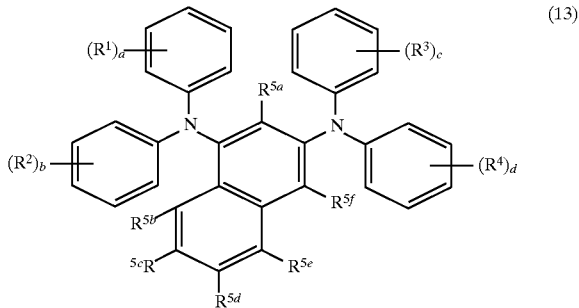

and 1,4-naphthylenediamine derivative represented by the general formula (14):

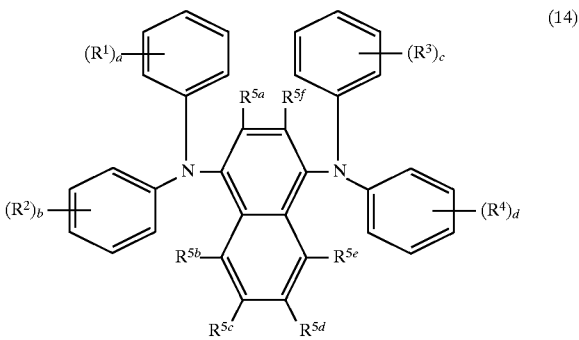

belong to the naphthylenediamine derivative of the present invention (in the above respective formulas $R^1$ to $R^4$, $R^{5a}$ to $R^{5f}$ and a to d are as defined above).

Among these four sorts of naphthylenediamine derivatives, the 2,3-naphthylenediamine derivative represented by the general formula (11) and 1,3-naphthylenediamine derivative represented by the general formula (13) are particularly preferred.

The former derivative (11) is superior in electric charge transferring capability due to the above effect of non-localization of electrons at the HOMO level because four phenyl groups substituted on two nitrogen atoms are located close each other, and is also particularly superior in stability at the time of light irradiation. In addition, it seemed that such a 2,3-naphthylenediamine derivative (11) has low asymmetry of the molecule in comparison with the 1,3-naphthylenediamine derivative (13). However, the derivative has a right compatibility with binding resin for practical use because a slight torsion is formed in the molecular structure due to a steric hindrance of phenyl groups substituted on two nitrogen atoms and the non-symmetry is enhanced.

Accordingly, regarding the electrophotosensitive material comprising a photosensitive layer containing the 2,3-naphthylenediamine derivative (11), the electric charge generation efficiency in the electric charge generating material is improved because of excellent electric charge transferring capability of the derivative (11) and, at the same time, the residual potential at the time of image formation is lowered and the sensitivity is improved. In addition, the electrophotosensitive material comprising a photosensitive layer containing the 2,3-naphthylenediamine derivative (11) is also superior in durability because of stability of the derivative (11).

Non-limited examples of the 2,3-naphthylenediamine derivative include the compounds represented by the formulas (11-1) to (11-27).

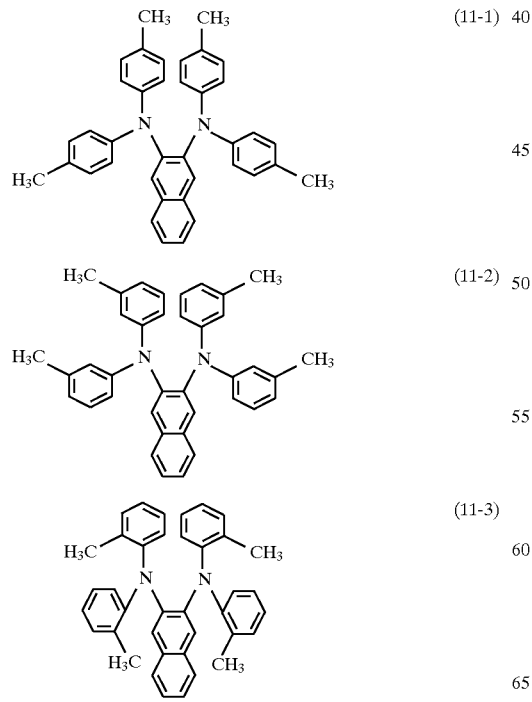

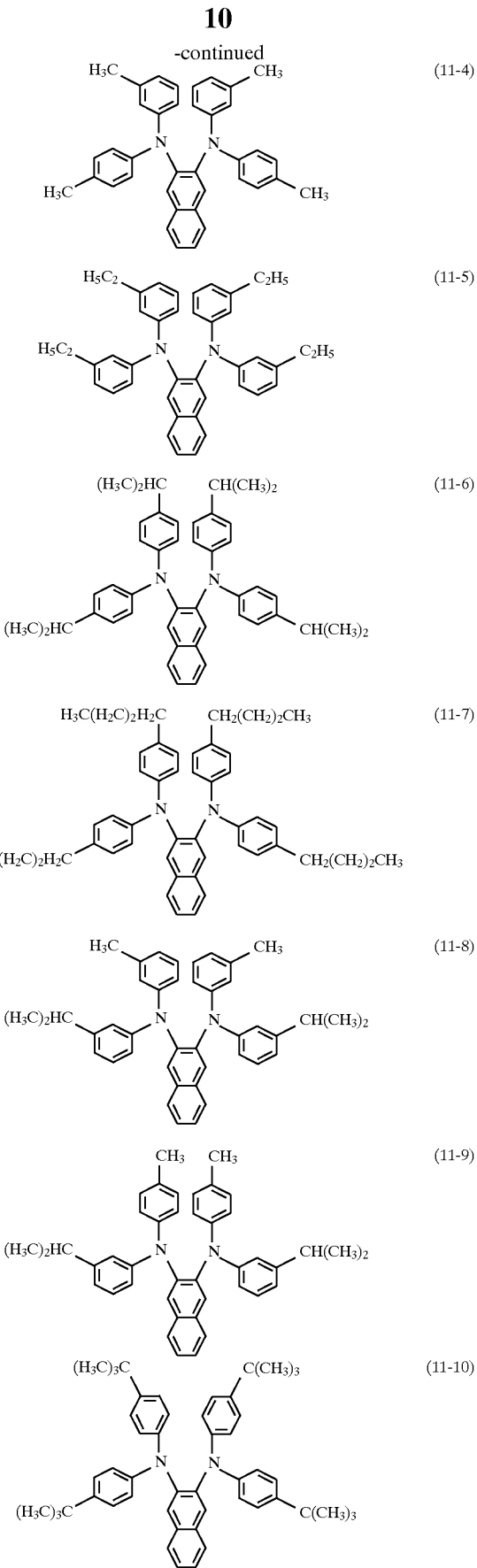

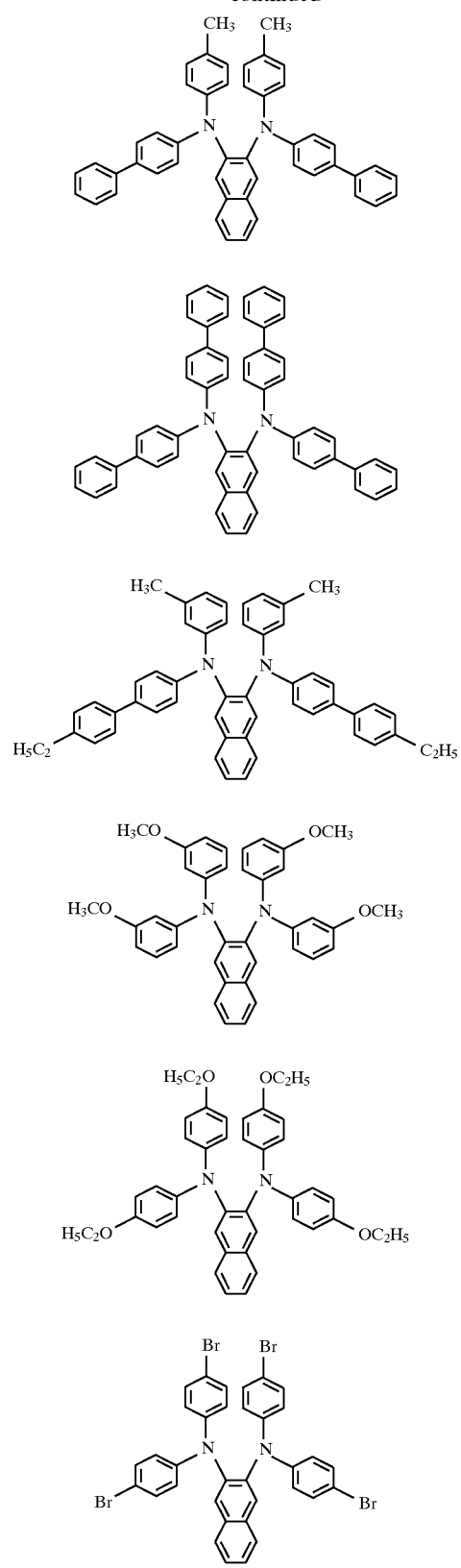
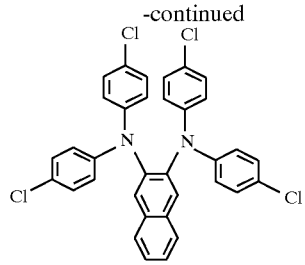
(11-17)
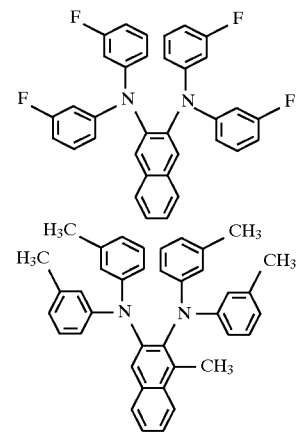
(11-18)
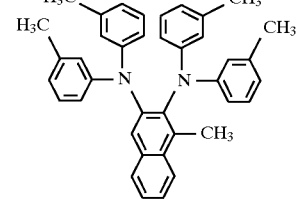
(11-19)
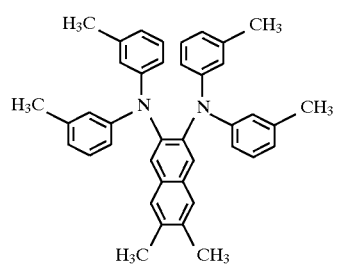
(11-20)
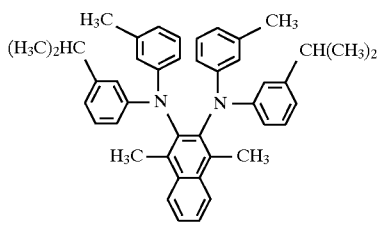
(11-21)
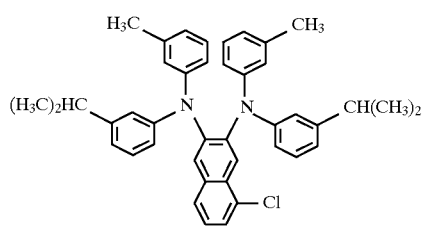
(11-22)
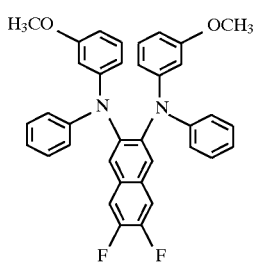
(11-23)

-continued

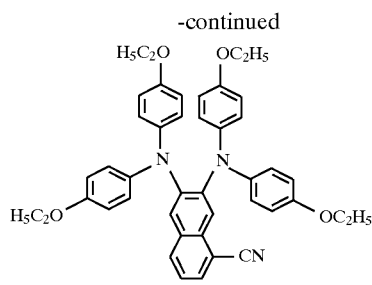 (11-24)

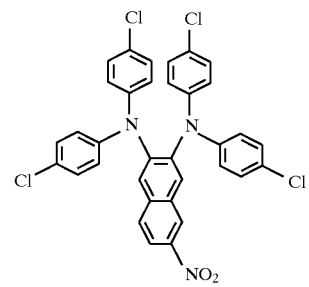 (11-25)

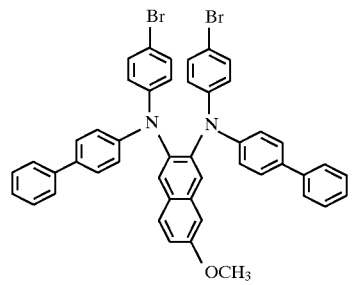 (11-26)

-continued

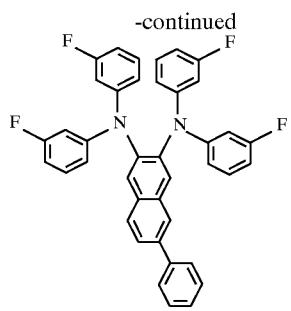 (11-27)

On the other hand, regarding the latter 1,3-naphthylenediamine derivative (13), four phenyl groups substituted on two nitrogen atoms are located separately in comparison with the 2,3-naphthylenediamine derivative (11). However, four phenyl groups are located close each other in comparison with those wherein two 6-membered rings constituting the naphthalene ring is respectively substituted with one nitrogen atom. Therefore, the derivative has a right electric charge transferring capability for practical use and stability at the time of light irradiation due to the effect of non-localization of electrons at the HOMO level. Furthermore, it is particularly superior in compatibility with binding resin because of strong asymmetry of the molecule.

Therefore, the electrophotosensitive material using the above 1,3-naphthylenediamine derivative (13) has the same sensitivity characteristics as those of the derivative using the 2,3-naphthylenediamine derivative (11), and is also superior in durability.

Example of the 1,3-naphthylenediamine derivative include the compounds represented by the formulas (13-1) to (13-26).

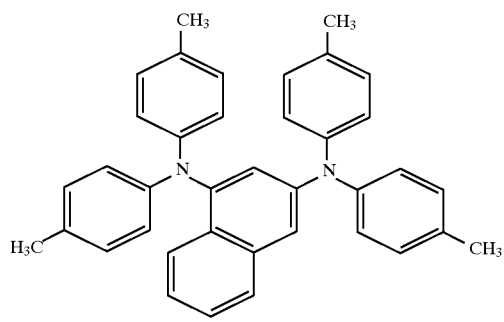 (13-1)

-continued
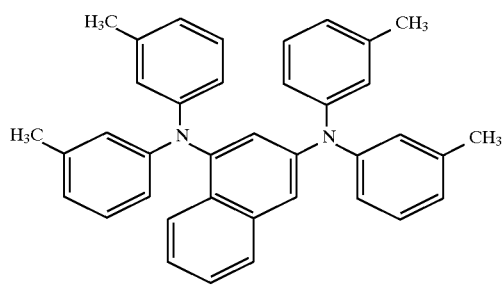
(13-2)
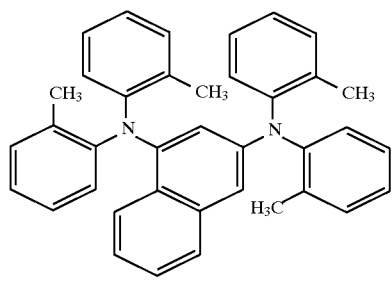
(13-3)
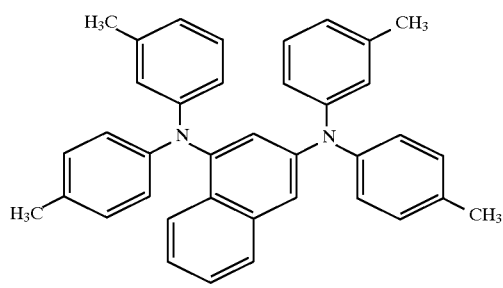
(13-4)
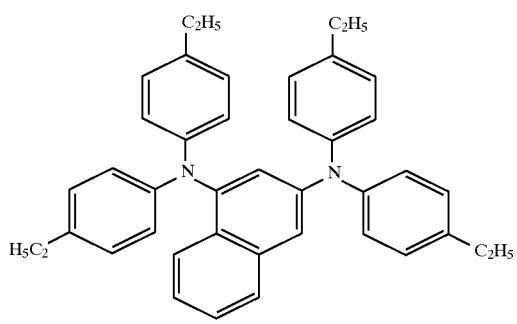
(13-5)
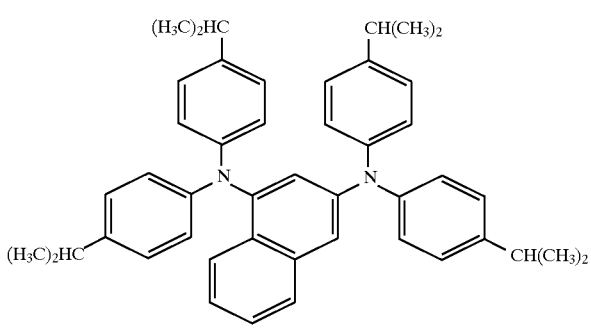
(13-6)

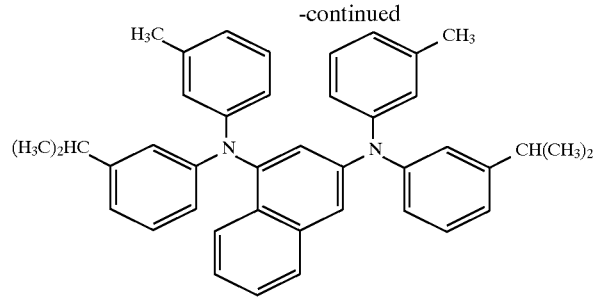
(13-7)
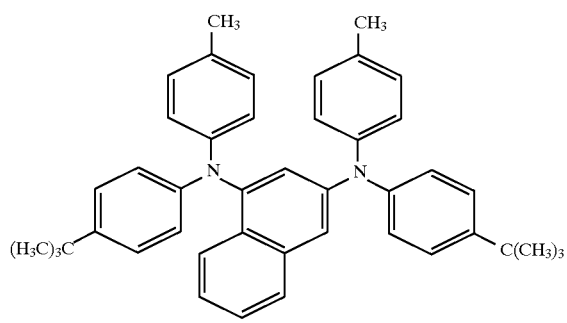
(13-8)
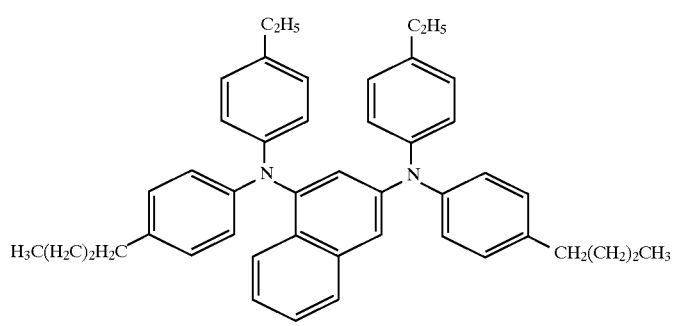
(13-9)
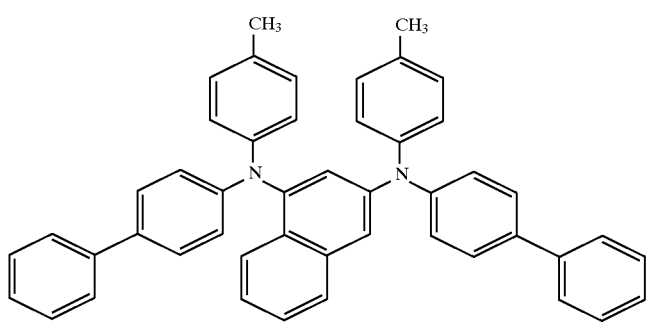
(13-10)
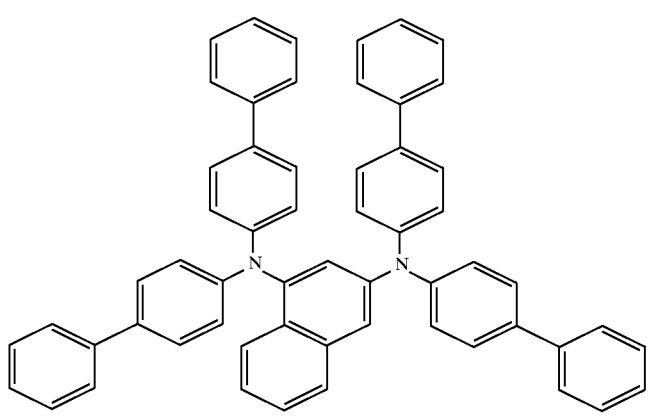
(13-11)

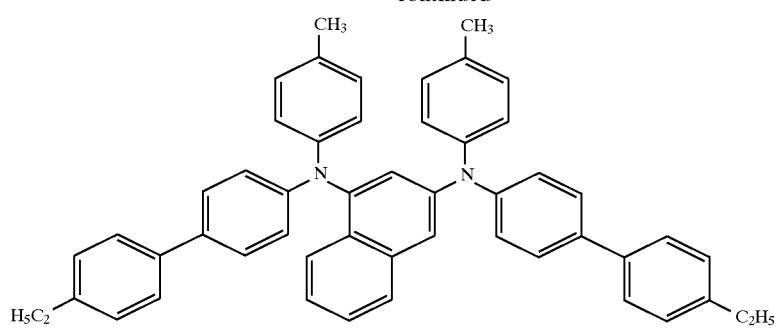
(13-12)
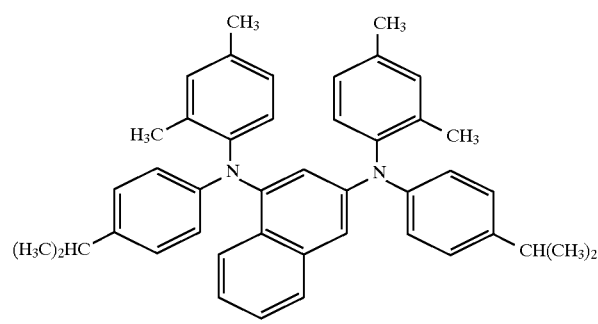
(13-13)
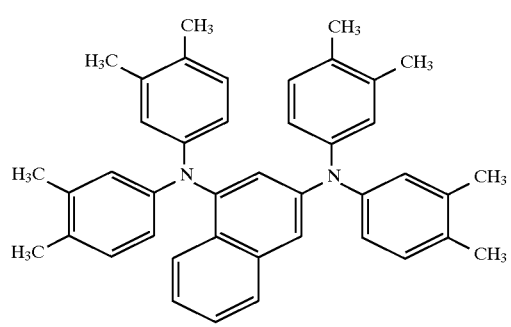
(13-14)
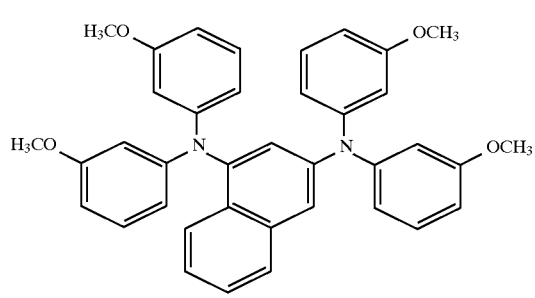
(13-15)
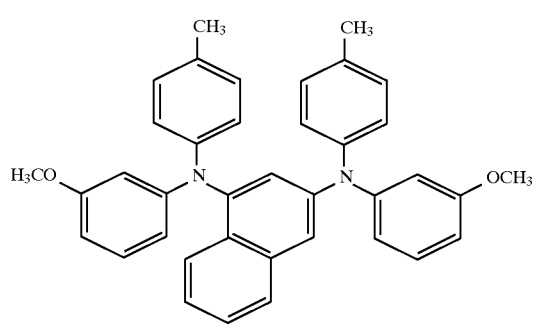
(13-16)

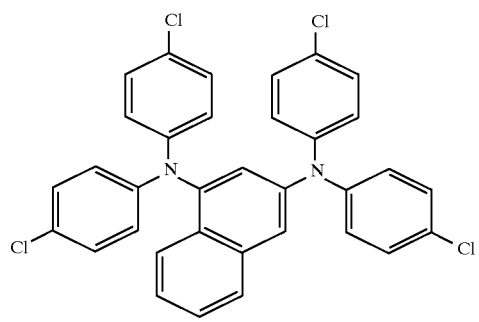
(13-17)
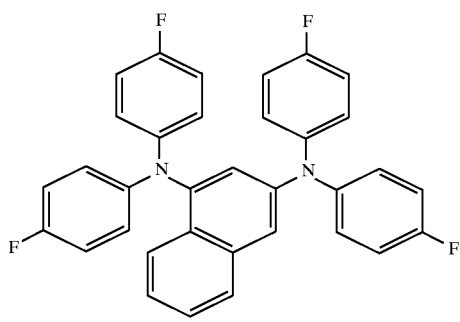
(13-18)
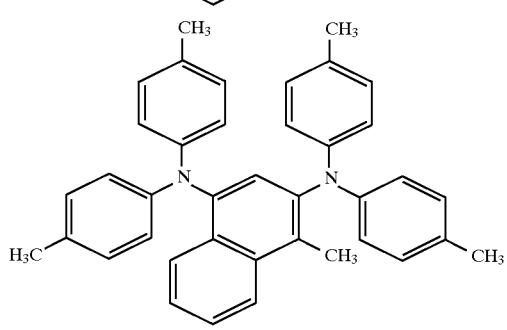
(13-19)
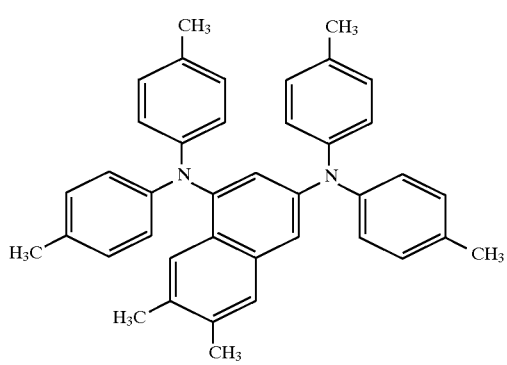
(13-20)
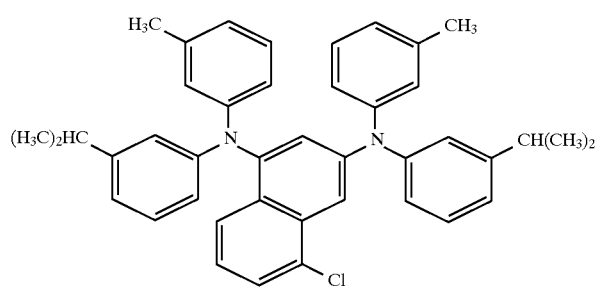
(13-21)

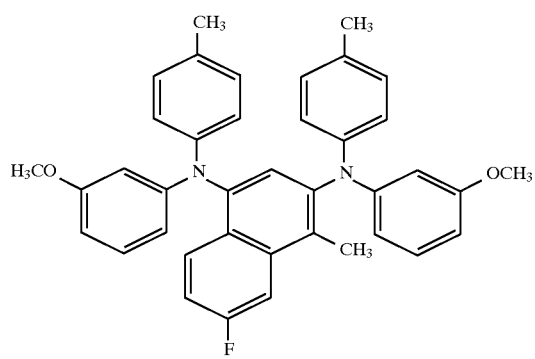
(13-22)
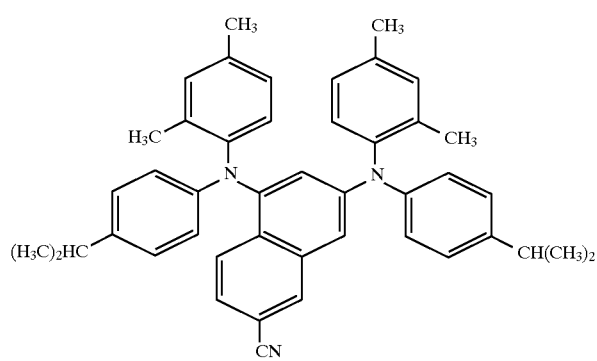
(13-23)
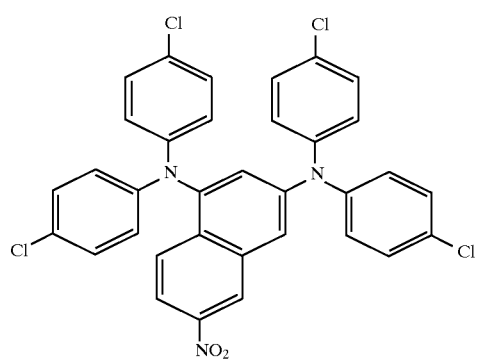
(13-24)
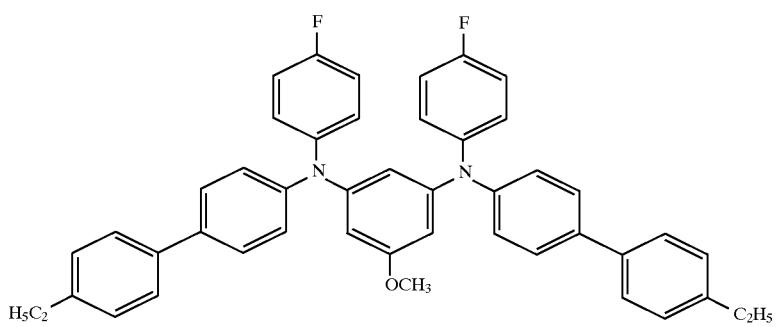
(13-25)

(13-26)

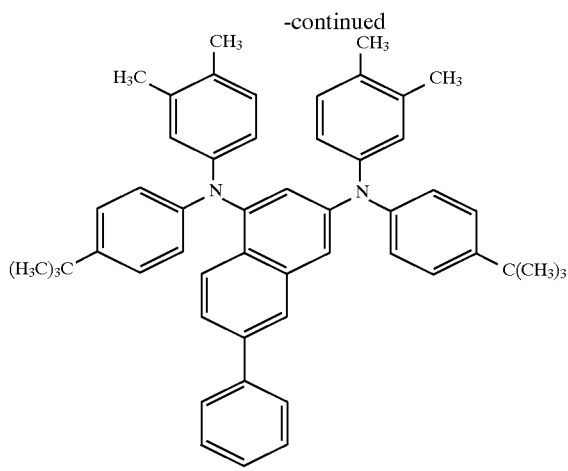

The naphthylenediamine derivative (1) of the present invention can be synthesized by various methods. For example, the 2,3-naphthylenediamine derivative represented by the following general formula (11a), wherein the groups $R^1$ to $R^4$ indicate the same group $R^{11}$, simultaneously, and the substituting number k and position to be substituted on the phenyl group are the same, among the compounds included in the 2,3-naphthylenediamine derivative (11) can be synthesized according to the following reaction scheme.

That is, a 2,3-naphthylenediamine derivative represented by the general formula (1a) is mixed with an iodobenzene derivative represented by the general formula (1b) in a molar ratio of 1:4, together with copper powder, copper oxide or halogenated copper, and the mixture is reacted under the presence of a basic substance to synthesize a 2,3-naphthylenediamine derivative (11a).

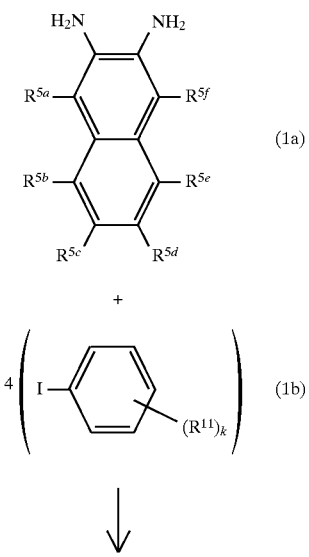

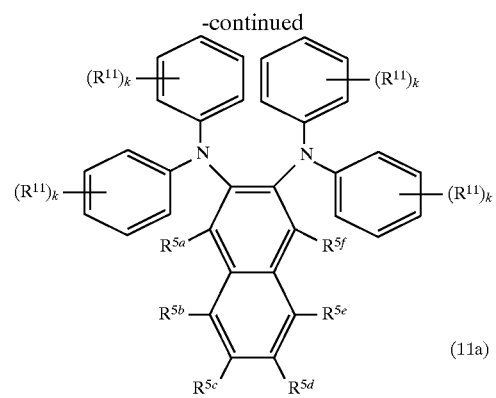

In order to synthesize a similar derivative which belongs to the 1,3-naphthylenediamine derivative (13), the same amount of a 1,3-naphthylenediamine derivative represented by the general formula (1c):

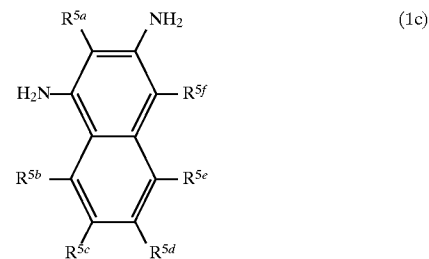

may be used in place of the 2,3-naphthylenediamine derivative (1a) as a starting material in the above reaction.

In addition, the compound represented by the following general formula (11b), wherein the groups $R^1$ and $R^3$ indicate the same group $R^{12}$, simultaneously, and the substituting number m and position to be substituted on the phenyl group are the same; the groups $R^2$ and $R^4$ indicate the same group $R^{13}$, simultaneously, and the substituting number n and position to be substituted on the phenyl group are the same; and the groups $R^{12}$ and $R^{13}$ are different each other, or the substituting numbers m and n are different or position of the groups $R^{12}$ and $R^{13}$ to be substituted on phenyl groups are different, among the compounds included in the 2,3-naphthylenediamine derivative (11) can be synthesized according to the following reaction scheme.

That is, an acetylated 2,3-naphthylenediamine derivative represented by the general formula (1d) is mixed with an iodobenzene derivative represented by the general formula (1e) in a molar ratio of 1:2, together with copper powder, copper oxide or halogenated copper, and the mixture is reacted under the presence of a basic substance to synthesize a reaction intermediate represented by the general formula (1f).

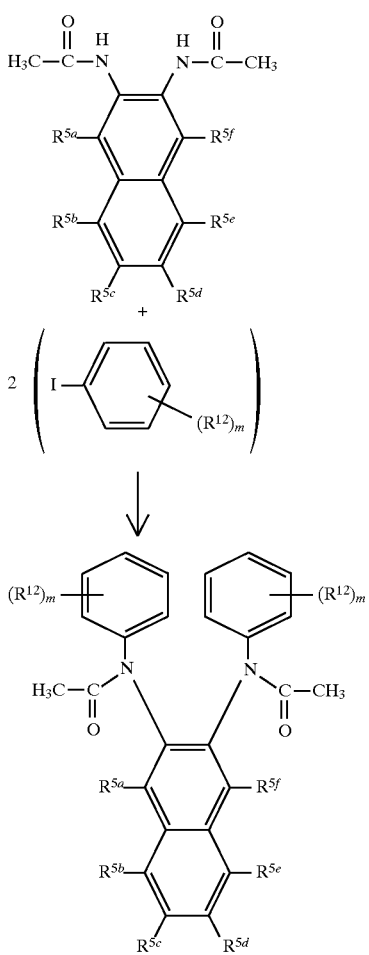

Then, this reaction intermediate is deacetylated by reacting with hydrochloric acid etc. in a suitable solvent to give a second intermediate. The obtained second intermediate is similarly reacted with an iodobenzene derivative represented by the general formula (1h) in a molar ratio of 1:2 to synthesize a 2,3-naphthylenediamine derivative (11b).

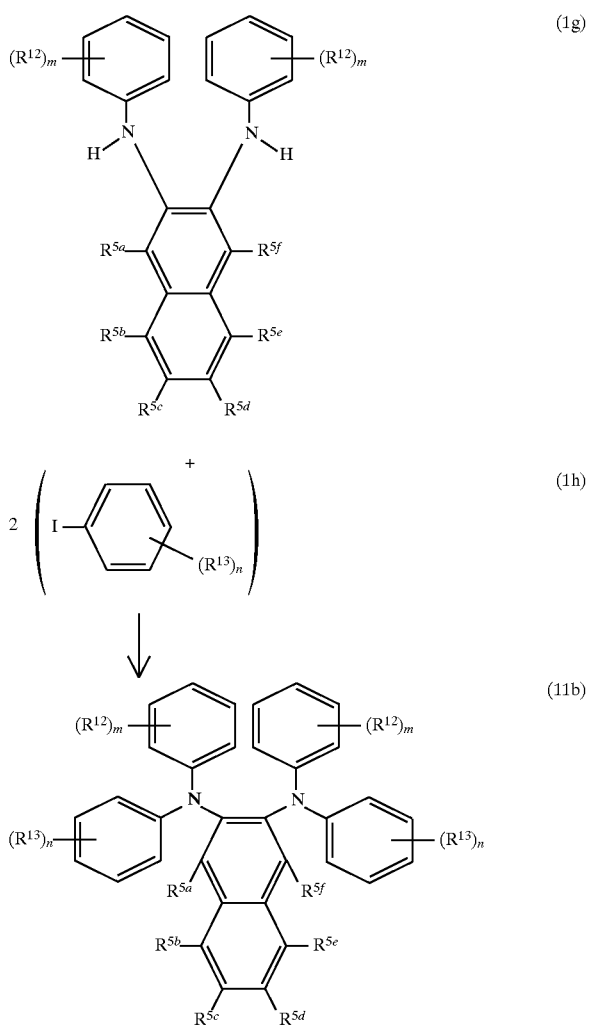

In order to synthesize a similar derivative which belongs to the 1,3-naphthylenediamine derivative (13), the same amount of an acetylated 1,3-naphthylenediamine derivative represented by the general formula (1i):

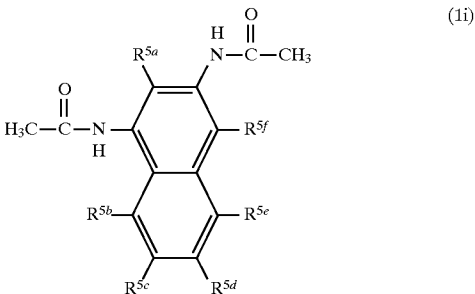

may be used in place of the acetylated 2,3-naphthylenediamine derivative (1d) as a starting material in the above reaction.

The naphthylenediamine derivative of the present invention is suitably used as an electric charge transferring material, particularly hole transferring material in applications such as solar battery, electroluminescent device, electrophotosensitive material, etc., and can also be used in other various fields.

The electrophotosensitive material of the present invention comprises a photosensitive layer containing at least one sort of the above naphthylenediamine derivative (1) on a conductive substrate. The photosensitive layer is classified into two types, i.e. a single-layer type photosensitive layer and a multi-layer type photosensitive layer. The present invention can be applied to both photosensitive layers.

The action and effect of the electrophotosensitive material using the naphthylenediamine derivative (1) as the hole transferring material and, if necessary, phenylenediamine derivative (7) and at least one sort of the above five sorts of electron transferring materials in combination is remarkably observed in the single-layer type photosensitive layer, particularly. In that case, there is an advantage that the resulting photosensitive material can be used for positive and negative charging. However, it is also possible to use it for the above-described multi-layer type photosensitive layer, as a matter of course.

The single-layer type photosensitive layer can be formed by applying a coating solution, which is prepared by dissolving or dispersing at least naphthylenediamine derivative among the naphthylenediamine derivative (1) and phenylenediamine derivative (7) as the electron transferring material, an electric charge generating material and a binding resin and, if necessary, at least one sort of the above five sorts of electron transferring materials in a suitable solvent, on a conductive substrate using a means such as application, followed by drying.

In addition, the multi-layer type photosensitive layer can be formed by forming an electric charge generating layer containing an electric charge generating material on a conductive substrate using a means such as deposition or application. Next, a coating solution containing a naphthylenediamine derivative (1) as an electron transferring material and a binding resin is applied on the electric charge generating layer using a means such as application, followed by drying to form an electric charge transferring layer. To the contrary, an electric charge transferring layer may be formed on a conductive substrate and then an electric charge generating layer may be formed thereon.

In case of multi-layer type photosensitive layer, the electron transferring material is normally contained in the electric charge generating layer, but it may also be contained in the electric charge transferring layer. In addition, the phenylenediamine derivative (7) as the hole transferring material is normally contained in the electric charge transferring layer, together with the naphthylenediamine derivative (1), but it may also be contained in the electric charge generating layer.

Examples of the electric charge generating material include powder of inorganic photoconductive materials (e.g. selenium, selenium-tellurium, selenium-arsenic, cadmium sulfide, α-silicon), azo pigments, bisazo pigments, perylene pigments, anthanthrone pigments, phthalocyanine pigments, indigo pigments, triphenylmethane pigments, therene pigments, toluidine pigments, pyrazoline pigments, quinacridone pigments, dithioketopyrrolopyrrole pigments, and the like. These electric charge generating materials can be used alone or in combination thereof according to the range of sensitivity of the electrophotosensitive material.

As the electric charge generating material suitable for an organic electrophotosensitive material having sensitivity at a wavelength within a range of not less than 700 nm, for example, there are phthalocyanine pigments such as X-type metal-free phthalocyanine, oxotitanyl phthalocyanine and the like. The electrophotosensitive material using these phthalocyanine pigments as the electric charge generating material and the naphthylenediamine derivative (1) as the electron transferring material has a high sensitivity in the above range of the wavelength. For example, it is suitably used for digital optical system image forming apparatuses such as laser beam printer and facsimile.

On the other hand, as the electric charge generating material which is suitable for the organic electrophotosensitive material having high sensitivity in the visible range, there are azo pigments, perylene pigments, etc. The electrophotosensitive material using these pigments as the electric charge generating material and the naphthylenediamine derivative (1) as the electron transferring material has a high sensitivity in the visible range. For example, it can be suitably used for analogue optical system image forming apparatuses such as electrostatic copying machine, etc.

The naphthylenediamine derivative (1) as the electron transferring material can be used alone or in combination with the 2,4,7-trinitrofluorenonimine derivative (2), diphenoquinone derivative (3), ethylated nitrofluorenonimine derivative (4), tryptoanthrine derivative (5), tryptoanthrinimine derivative (6) or phenylenediamine derivative (7), as described above. Furthermore, it can also be used in combination with other electric charge transferring materials which have hitherto been known.

Examples of the halogen atom, alkyl group, alkoxy group and aryl group, which correspond to the groups $R^A$, $R^B$, $R^C$, $R^D$ and $R^E$ in the above general formula (2) representing the 2,4,7-trinitrofluorenonimine derivative, include the same groups as those described above. In addition, examples of the aralkyl group include benzyl group, benzhydryl group, phenethyl group, etc. As substituents which may substituted on these groups or the naphthyl group, there are the same groups as those described above.

Examples of the 2,4,7-trinitrofluorenonimine derivative (2) include the compounds represented by the formulas (2-1) to (2-20).

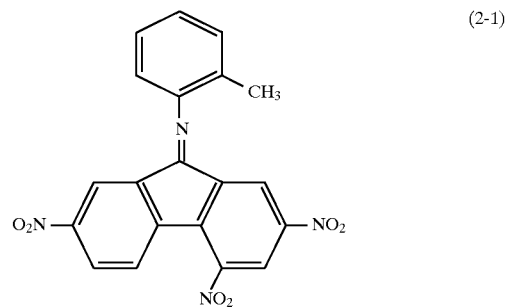

(2-1)

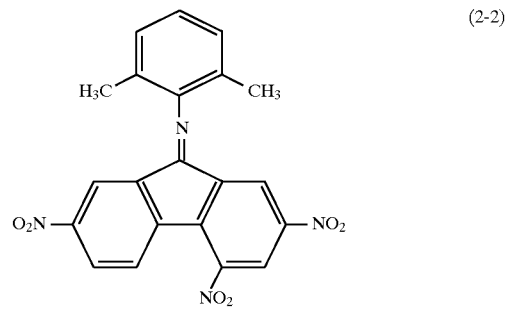

(2-2)

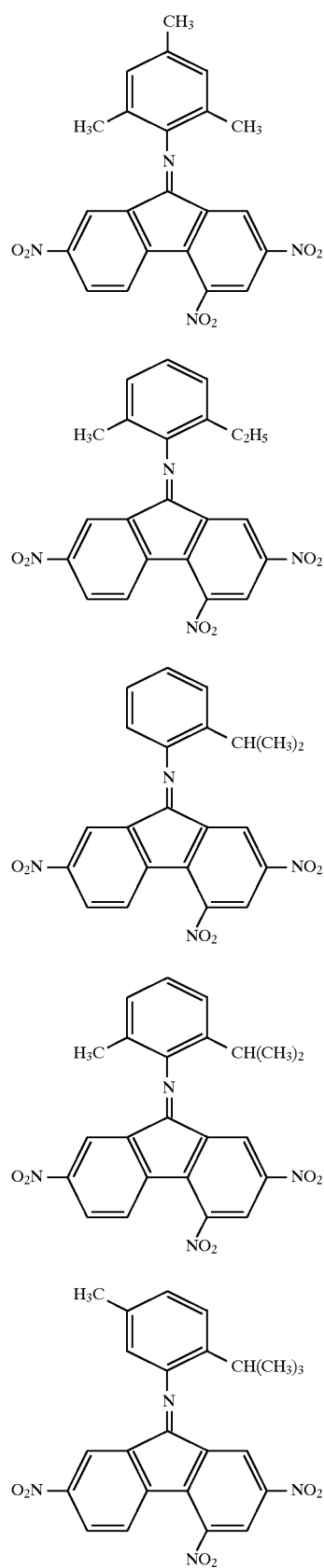
(2-3)
(2-4)
(2-5)
(2-6)
(2-7)
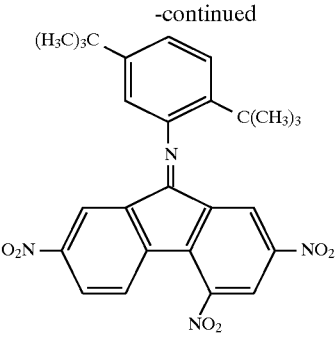
(2-8)
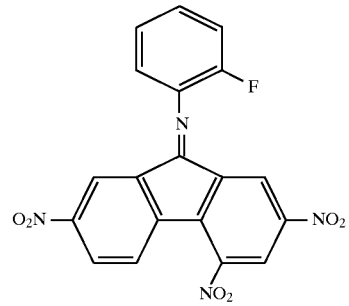
(2-9)
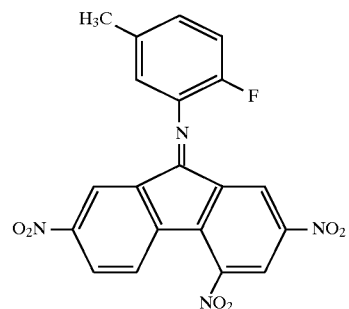
(2-10)
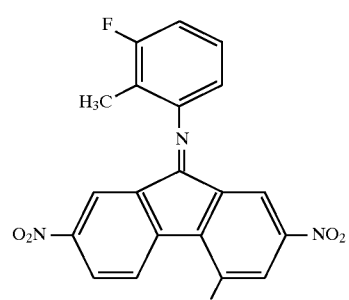
(2-11)
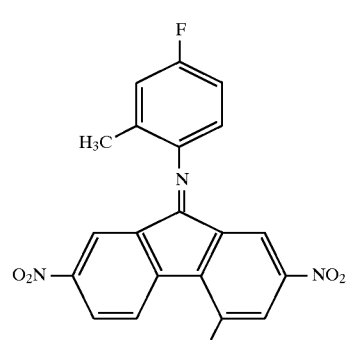
(2-12)

(2-13) 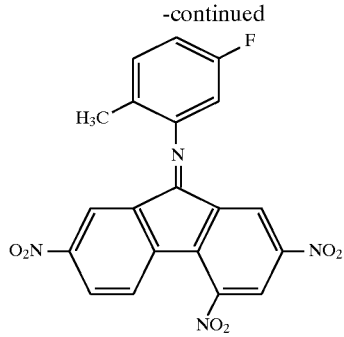

(2-14) 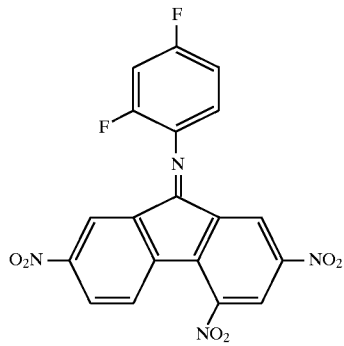

(2-15) 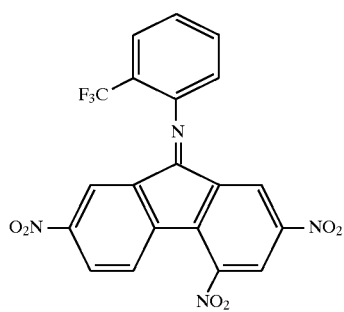

(2-16) 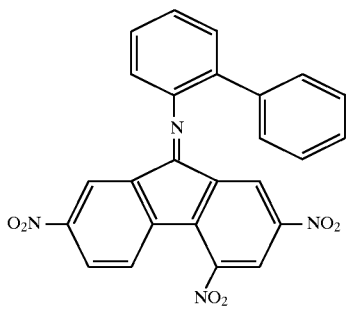

(2-17) 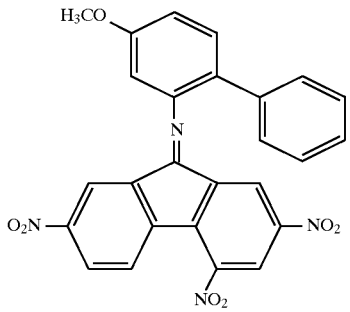

(2-18) 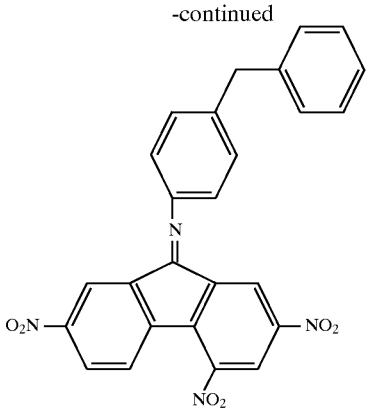

(2-19) 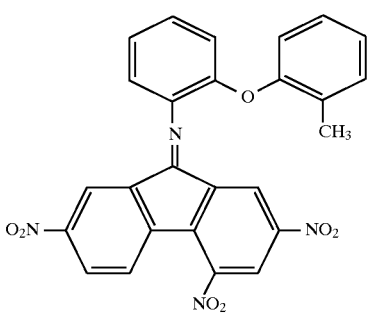

(2-20) 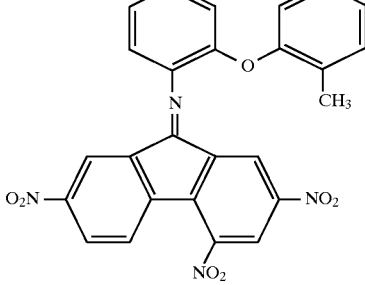

Examples of the halogen atom, alkoxy group, aryl group and aralkyl group, which correspond to the groups $R^F$, $R^G$, $R^H$ and $R^I$ in the above general formula (3) representing the diphenoquinone derivative, as well as substituents which may be substituted on these groups include the same groups as those described above. Examples of the alkyl group include cyclic alkyl groups such as cyclohexyl group, etc., in addition to the above respective groups.

Examples of the diphenoquinone derivative (3) include the compounds represented by the formulas (3-1) to (3-9).

(3-1) 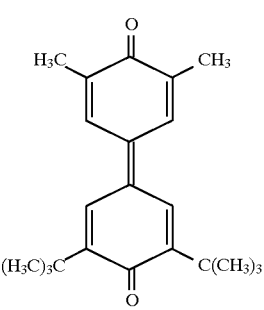

-continued

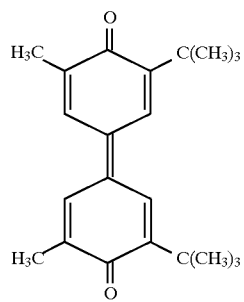
(3-2)

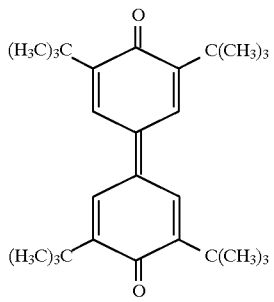
(3-3)

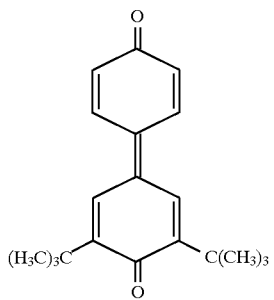
(3-4)

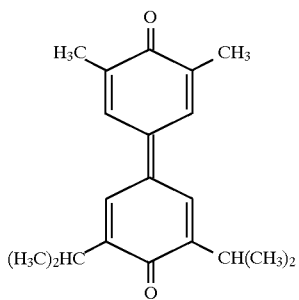
(3-5)

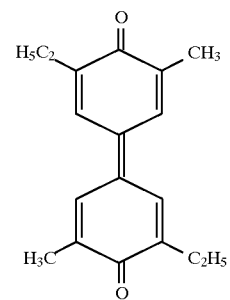
(3-6)

-continued

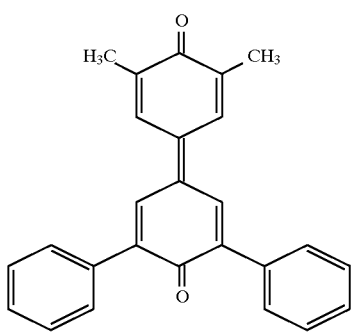
(3-7)

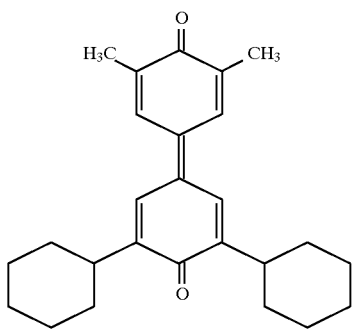
(3-8)

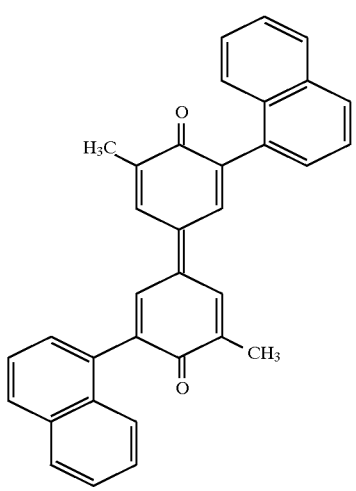
(3-9)

Examples of the halogen atom, alkyl group, alkoxy group, aryl group and aralkyl group, which correspond to the groups $R^J$, $R^K$, $R^L$, $R^M$ and $R^N$ in the above general formula (4) representing the ethylated nitrofluorenonimine derivative, as well as substituents which may be substituted on these groups or phenoxy group include the same groups as those described above.

Examples of the ethylated nitrofluorenonimine derivative (4) include the compounds represented by the formulas (4-1) to (4-9).

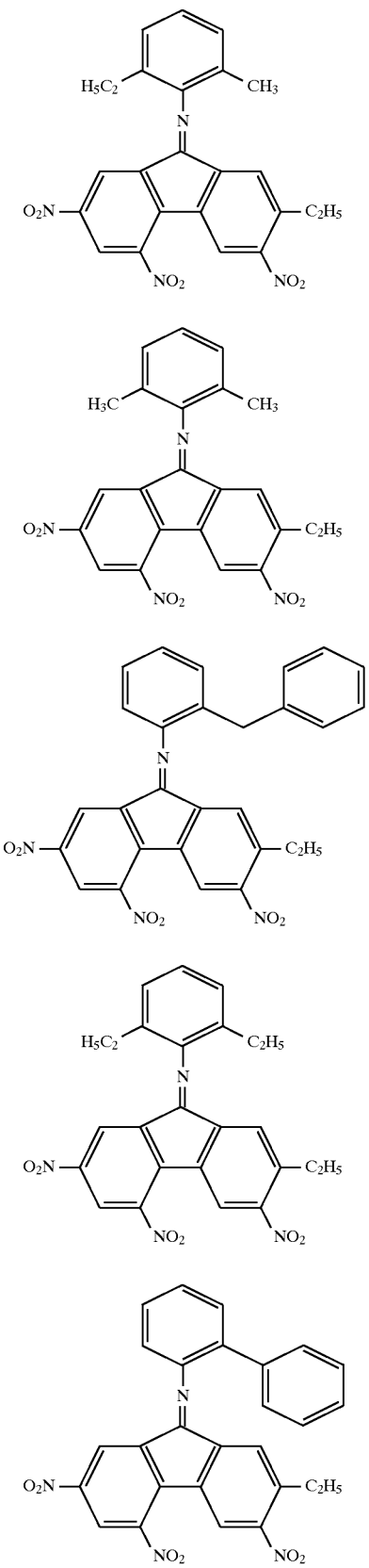

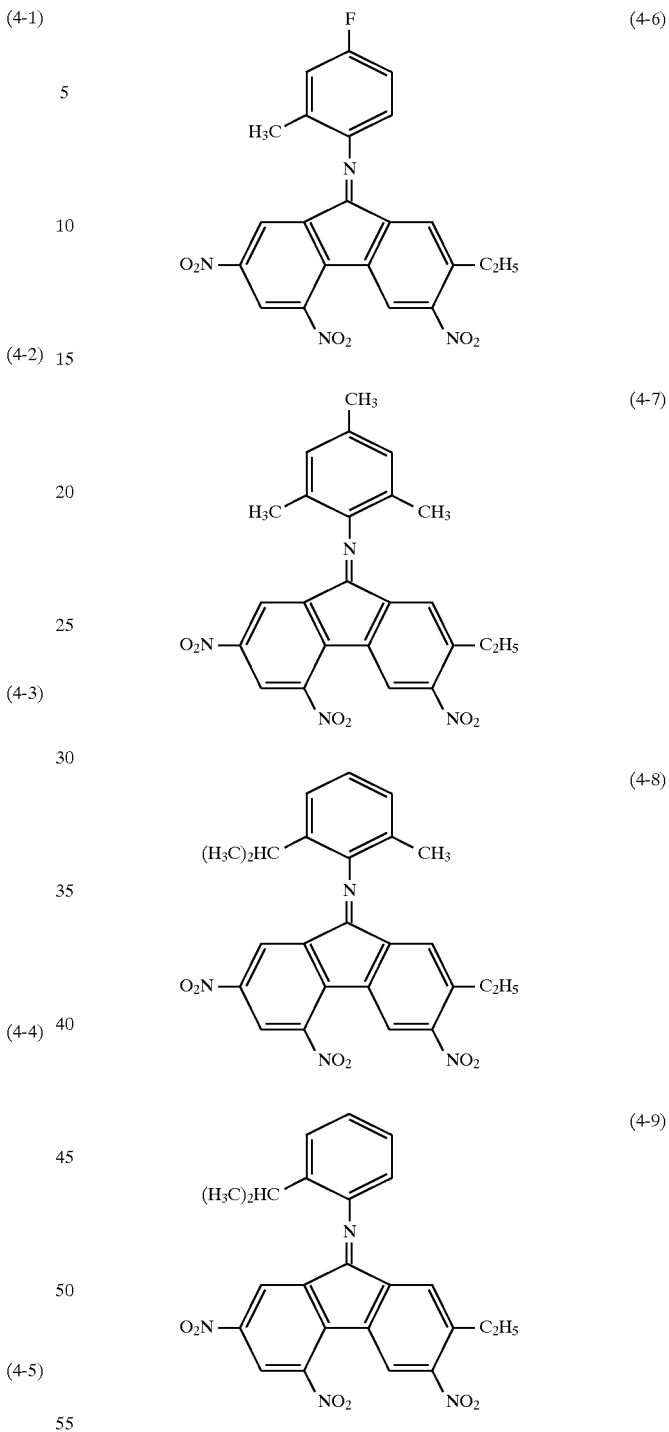

Examples of the alkyl group and alkoxy group, which correspond to the groups $R^O$ and $R^P$ in the above general formula (5) representing the tryptoanthrine derivative, as well as substituents which may be substituted on these groups include the same groups as those described above.

Examples of the tryptoanthrine derivative (5) include the compounds represented by the formulas (5-1) to (5-5).

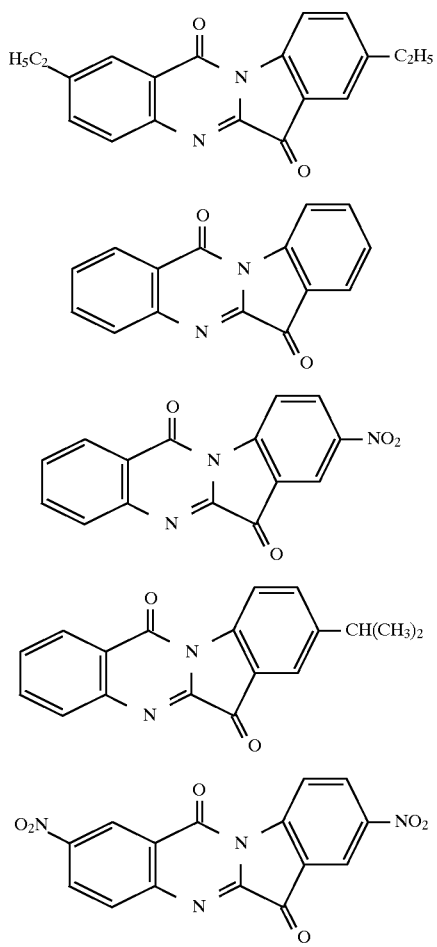

Examples of the halogen atom, alkyl group, alkoxy group, aryl group and aralkyl group, which correspond to the groups $R^Q$, $R^R$, $R^S$, $R^T$ and $R^U$ in the above general formula (6) representing the tryptoanthrinimine derivative, as well as substituents which may be substituted on these groups or phenoxy group include the same groups as those described above.

Examples of the tryptoanthrinimine derivative (6) include the compounds represented by the formulas (6-1) to (6-11).

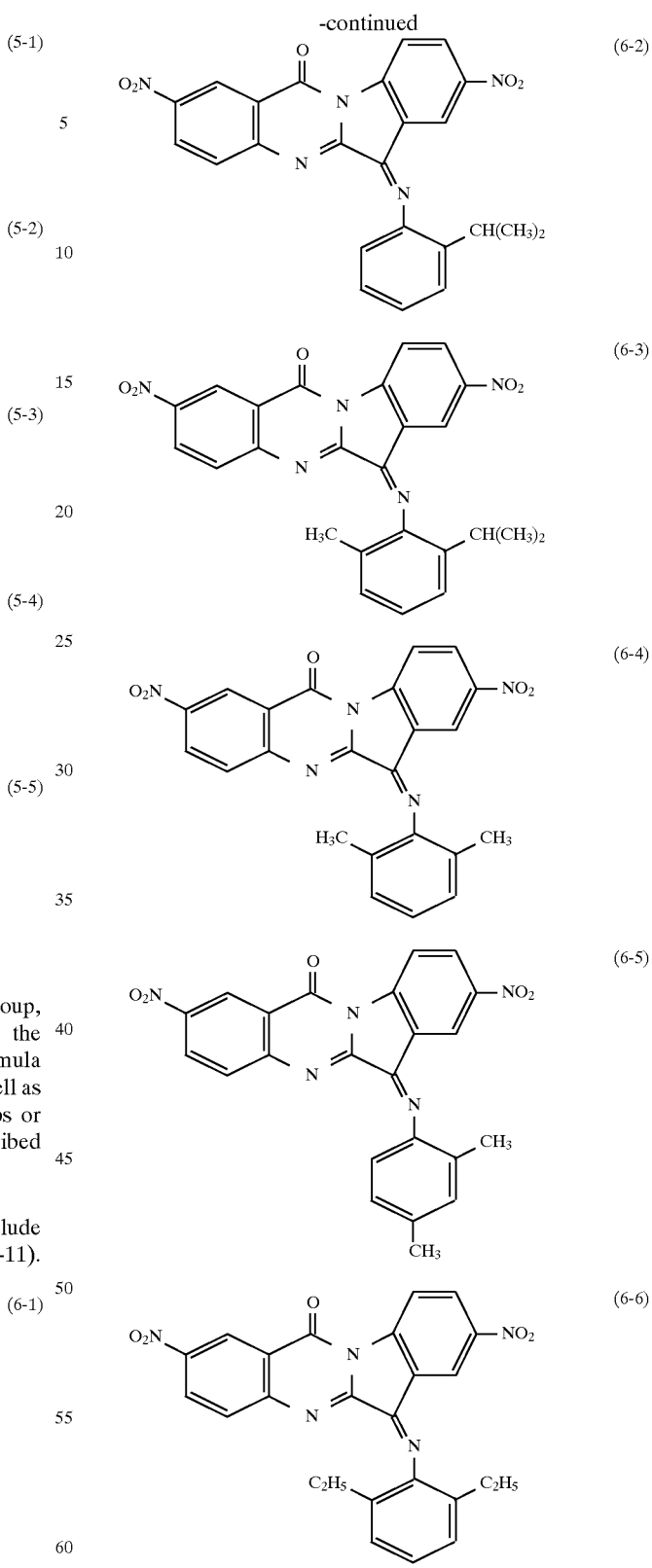

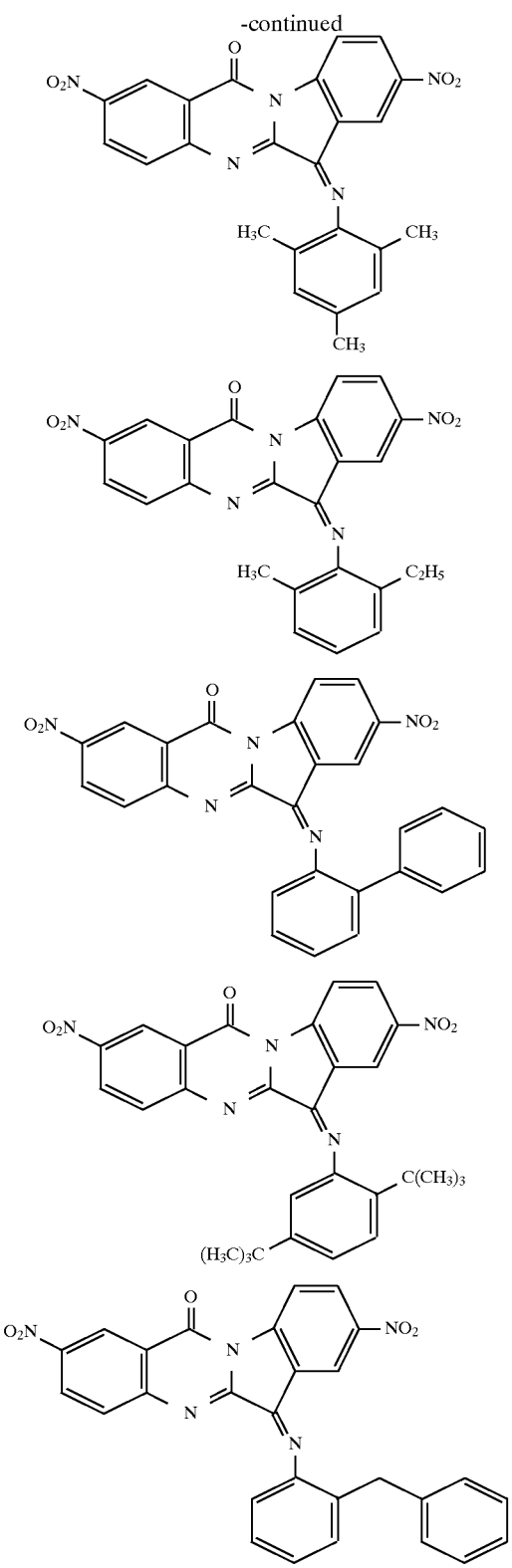

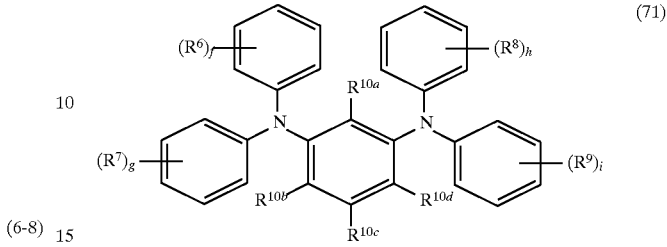

to be substituted on the center benzene ring, e.g. o-, m- and p-phenylenediamine derivatives. In the present invention, two sorts of them such as m-phenylenediamine derivative represented by the general formula (71):

and o-phenylenediamine derivative represented by the general formula (72):

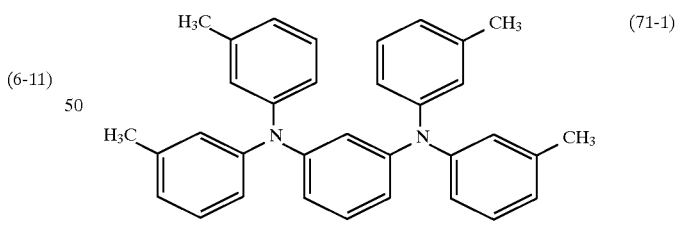

are suitably used (in the above formulas $R^6$ to $R^9$, $R^{10a}$ to $R^{10d}$ and f to i are as defined above) in view of intensity of an interaction with the naphthylenediamine derivative, compatibility with other materials, electric charge transferring capability, etc.

Examples of the m-phenylenediamine derivative (71) include the compounds represented by the formulas (71-1) to (71-3).

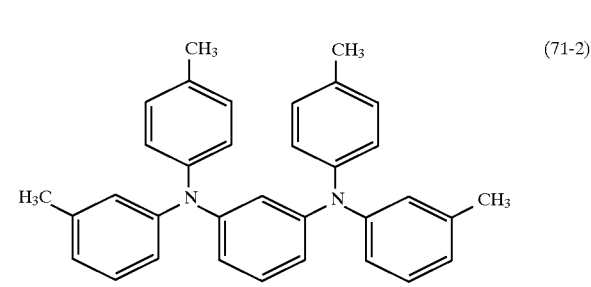

Examples of the halogen atom, alkyl group, alkoxy group and aryl group, which correspond to the groups $R^6$, $R^7$, $R^8$, $R^9$ and $R^{10a}$ to $R^{10d}$ in the above general formula (7) representing the phenylenediamine derivative, as well as substituents which may be substituted on these groups include the same groups as those described above.

The phenylenediamine derivative (7) is classified into three sorts according to the position of two nitrogen atoms

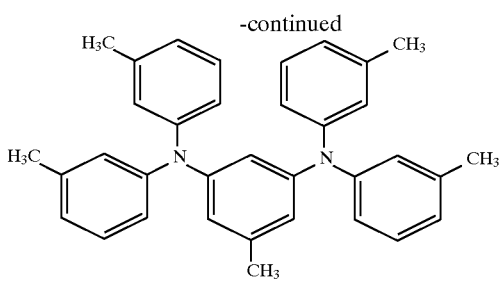

(71-3)

Examples of the o-phenylenediamine derivative (72) include the compound represented by the formula (72-1):

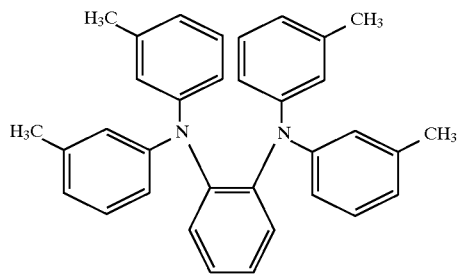

(72-1)

Examples of the other electric charge transferring material which may be used in combination with the above respective electric charge transferring materials include various electron transferring materials and hole transferring materials.

Examples of the electron transferring material among electric charge transferring materials include electron attractive materials such as benzoquinone compound, naphthoquinone compound, malononitrile, thiopyran compound, tetracyanoethylene, tetracyanoquinodimethane, chloroanil, bromoanil, 2,4,7-trinitro-9-dicyanomethylenefluorenone, 2,4,5,7-tetranitroxanthone, 2,4,8-trinitrothioxanthone, dinitrobenzene, dinitroanthracene, dinitroacridine, nitroanthraquinone, dinitroanthraquinone, succinic anhydride, maleic anhydride, dibromomaleic anhydride, etc., high-molecular compounds obtained by polymerizing the above electron attractive materials, and the like.

Examples of the hole transferring material include electron donative materials such as nitrogen-containing cyclic compounds and condensed polycyclic compounds, for example, diamine compounds other than naphthylenediamine derivative (1) and phenylenediamine derivative (7); diazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; pyrazoline compounds such as 1-phenyl-3-(p-dimethylaminophenyl)pyrazoline, etc.; hydrazone compounds; triphenylamine compounds; indol compounds; oxazole compounds; isooxazole compounds, thiazole compounds; thiadiazole compounds; imidazole compounds; pyrazole compounds; triazole compounds and the like.

These electric charge transferring materials can also be used alone or in combination thereof. Further, when using an electric charge transferring material having film forming properties such as polyvinyl carbazole, the binding resin is not necessarily required.

Examples of the binding resin include thermoplastic resins such as styrene polymer, styrene-butadiene copolymer, styrene-acrylonitrile copolymer, styrene-maleic acid copolymer, acrylic polymer, styrene-acrylic copolymer, polyethylene, ethylene-vinyl acetate copolymer, chlorinated polyethylene, polyvinyl chloride, polypropylene, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, etc.; crosslinking thermosetting resins such as silicone resin, epoxy resin, phenol resin, urea resin, melamine resin, etc.; photosetting resins such as epoxy acrylate, urethane acrylate, etc. These binding resins can be used alone or in combination thereof.

Additives such as sensitizers, fluorene compounds, ultraviolet absorbers, plasticizers, surfactants, leveling agents, etc. can be added to the photosensitive layer, in addition to the above respective components. In order to improve sensitivity of the electrophotosensitive material, there may be used sensitizers such as tertphenyl, halonaphthoquinones, acenaphthylene, etc. in combination with the electric charge generating agent.

In the multi-layer photosensitive material, the electric charge generating material and the binding resin, both of which constitute the electric charge generating layer, may be used in various proportions. It is preferred that 5 to 1000 parts by weight, particularly 30 to 500 parts by weight of the electric charge generating material is used, based on 100 parts by weight of the binding resin.

The electric charge transferring material and the binding resin, both of which constitute the electric charge transferring layer, can be used in various proportions within such a range as not to prevent the transmission of the electric charge and as to prevent the crystallization of the electric charge transferring material. It is preferred that 10 to 500 parts by weight, particularly 25 to 200 parts by weight of the electric charge transferring material containing the naphthylenediamine derivative (1) is used, based on 100 parts by weight of the binding resin so as to easily transfer the electric charge generated in the electric charge generating layer due to light irradiation. The amount of the electric charge transferring material is that of the naphthylenediamine derivative (1) when the naphthylenediamine derivative (1) is used alone. When using the naphthylenediamine derivative (1) in combination with the other electric charge transferring material, the amount of the electric charge transferring material is the total amount of both derivatives. For example, when using the naphthylenediamine derivative (1) in combination with the phenylenediamine derivative (7), the proportion (weight ratio) of both derivatives is preferably within a range of 20:80 to 80:20 (naphthylene derivative (1):phenylenediamine derivative (7)).

Regarding the thickness of the multi-layer type photosensitive layer, it is preferred that the thickness of the electric charge generating layer is about 0.01 to 5 $\mu$m, particularly about 0.1 to 3 $\mu$m and the thickness of the electric charge transferring layer is about 2 to 100 $\mu$m, particularly about 5 to 50 $\mu$m.

In the single-layer type photosensitive material, it is suitable that 0.1 to 50 parts by weight, particularly 0.5 to 30 parts by weight of the electric charge generating material and 20 to 500 parts by weight, particularly 30 to 200 parts by weight of the electric charge transferring material containing the naphthylenediamine derivative (1) are used, based on 100 parts by weight of the binding resin. The amount of the electric charge transferring material is that of the naphthylenediamine derivative (1) when the naphthylenediamine derivative (1) is used alone. When using the naphthylenediamine derivative (1) in combination with the other electric charge transferring material, the amount of the electric charge transferring material is the total amount of both derivatives.

In the system using the hole transferring material such as naphthylenediamine derivative (1), phenylenediamine derivative (7), etc. in combination with the electron transferring material such as 2,4,7-trinitrofluorenonimine derivative (2), diphenoquinone derivative (3), ethylated nitrofluorenonimine derivative (4), tryptoanthrine derivative (5), tryptoanthrinimine derivative (6), phenylenediamine derivative (7), etc., the proportion (weight ratio) of both transferring materials is preferably within a range of 90:10 to 40:60 (hole transferring material:electron transferring material).

Furthermore, in the system using the naphthylenediamine derivative (1) in combination with the phenylenediamine derivative (7), the proportion (weight ratio) of both transferring materials is preferably within a range of 20:80 to 80:20 (naphthylenediamine derivative (1):phenylenediamine derivative (7)).

It is preferred that the film thickness of the single-layer type photosensitive layer is 5 to 100 μm, particularly 10 to 50 μm.

A barrier layer may be formed, in such a range as not to injure the characteristics of the electrophotosensitive material, between the conductive substrate and the electrophotosensitive layer in the single-layer type photosensitive material, or between the conductive substrate and the electric charge generating layer, between the conductive substrate and the electric charge transferring layer or between the electric charge generating layer and the electric charge transferring layer in the multi-layer type photosensitive material. Further, a protective layer may be formed on the surface of the electrophotosensitive material.

As the conductive substrate on which the above respective layers are formed, various materials having conductivity can be used, and examples thereof include metals such as iron, aluminum, copper, tin, platinum, silver, vanadium, molybdenum, chromium, cadmium, titanium, nickel, palladium, indium, stainless steel, brass, etc.; plastic materials vapor-deposited or laminated with the above metal; glass materials coated with aluminum iodide, tin oxide, indium oxide, etc.

The conductive substrate may be made in the form of a sheet or a drum according to the structure of the image forming apparatus to be used. The substrate itself may have conductivity or only the surface of the substrate may have conductivity. It is preferred that the conductive substrate has a sufficient mechanical strength when used.

When the above respective layer constituting the electrophotosensitive material are formed by a coating method, the electric charge generating material, the electric charge transferring material, the binding resin, etc. may be dispersed/mixed with a suitable solvent by a known method, for example, using a roll mill, a ball mill, an atriter, a paint shaker, a supersonic dispenser, etc. to prepare a coating solution, which is applied by a known means and then allowed to dry.

As the solvent for preparing the coating solution, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; halogenated hydrocarbons such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethyl sulfoxide, etc. These solvents may be used alone or in combination thereof.

In order to improve dispersibility of the electric charge transferring material and electric charge generating material as well as smoothness of the surface of the photosensitive layer, there may be added surfactants, leveling agents, etc. to the coating solution.

EXAMPLES

The following Examples and Comparative Examples further illustrate the present invention.

Example 1

Synthesis of N,N,N', N'-tetrakis(3-methylphenyl)-2, 3-naphthyenediamine 2,3-Naphthylenediamine (15.8 g) represented by the formula (1A):

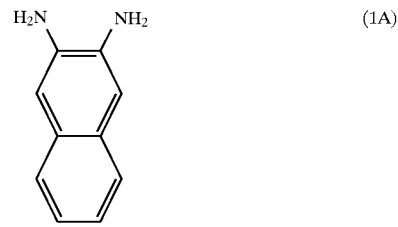

m-iodotoluene (87.2 g) represented by the formula (1B):

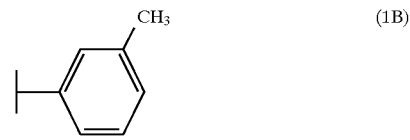

potassium carbonate (27.6 g) and copper powder (2 g) were added in 300 ml of nitrobenzene, and the mixture was refluxed while a nitrogen gas was blowing into this reaction system under vigorous stirring for 24 hours. The water content produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in cyclohexane. The solution was purified by subjecting to silica gel column chromatography and cyclohexane was distilled off to give a white precipitation. Then, the white precipitation was recrystallized from n-hexane to give the titled compound represented by the above formula (11-2) as an objective product (20.5 g, yield: 39.5%).

The results of the infrared spectroscopic analysis of the above compound are shown in FIG. 1. In addition, the results of the elemental analysis are shown below.

Elemental analysis (%):

Calcd.: C, 87.98; H, 6.61; N, 5.40

Found: C, 87.89; H, 6.66; N, 5.44

Example 2

Synthesis of N,N,N',N'-tetrakis(4-isopropylphenyl)-2,3-naphthylenediamine

According to the same manner as that described in Example 1 except for using 98.4 g of 4-isopropyl-iodobenzene represented by the formula (1C):

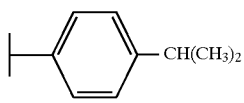

in place of m-iodotoluene represented by the formula (1B), the titled compound represented by the above formula (11-6) was obtained as an objective product (22.8 g, yield: 35.6%).

The results of the elemental analysis of the above compound are shown below.

Elemental analysis (%),

Calcd.: C, 86.18; H, 9.44; N, 4.37

Found: C, 86.01; H, 9.51; N, 4.47

Example 3

Synthesis of N,N'-bis(3-methylphenyl)-N,N'-bis(3-isopropylphenyl)-2,3-naphthylenediamine N,N'-diacetyl-2,3-naphthylenediamine (12.1 g) represented by the formula (1D):

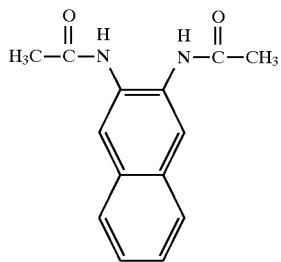

m-iodotoluene (21.8 g) represented by the above formula (1B), potassium carbonate (13.8 g) and copper powder (1 g) were added in 150 ml of nitrobenzene, and the mixture was refluxed while a nitrogen gas was blowing into this reaction system under vigorous stirring for 24 hours. The water content produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was added in 100 ml of tetrahydrofuran, together with 10% hydrochloric acid. The mixed solution was deacetylated by refluxing for two hours to give N,N'-bis(3-methylphenyl)-2,3-naphthylenediamine represented by the formula (1E):

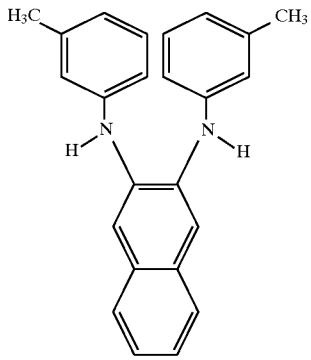

Then, this compound (8.46 g), 3-isopropyliodobenzene (12.3 g) represented by the formula (1F):

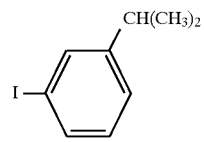

potassium carbonate (13.8 g) and copper powder (1 g) were added in 150 ml of nitrobenzene, and the mixture was refluxed while a nitrogen gas was blowing into this reaction system under vigorous stirring for 24 hours. The water content produced in the reaction was removed out of the reaction system by azeotropic distillation with nitrobenzene, according to the same manner as that described above.

After the reaction solution was cooled, the inorganic substance was filtered off. Further, nitrobenzene was distilled off by steam distillation to give the residue, which was dissolved in cyclohexane. The solution was purified by subjecting to silica gel column chromatography and cyclohexane was distilled off to give a white precipitation. Then, the white precipitation was recrystallized from n-hexane to give the titled compound represented by the above formula (11-8) as an objective product (6.35 g, yield: 22.1%).

Figure 2:
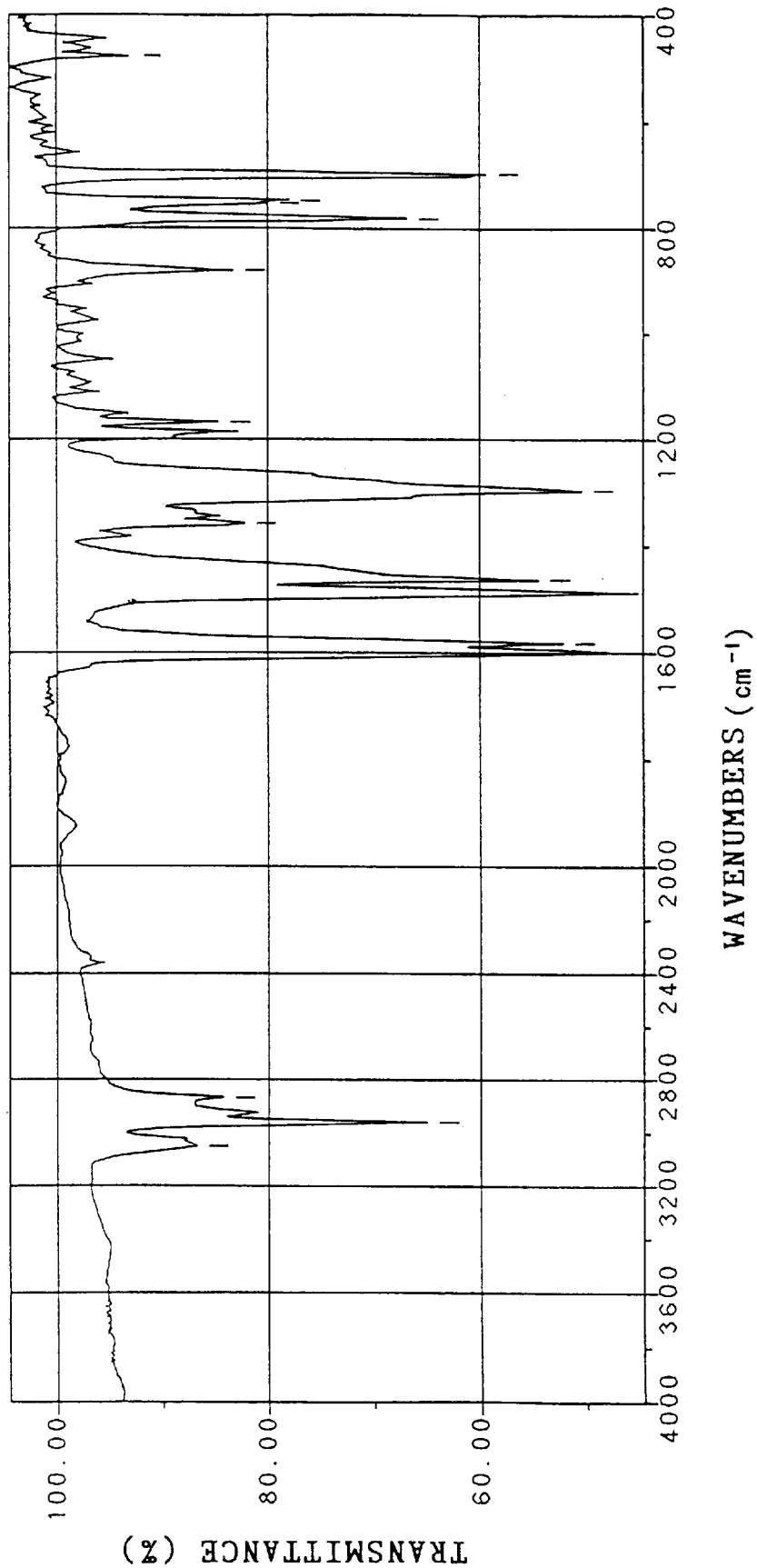
FIG. 2 is a graph illustrating the results of infrared spectroscopic analysis of the naphthylenediamine derivative of Example 3 according to the present invention.

The results of the infrared spectroscopic analysis of the resultant compound are shown in FIG. 2. In addition, the results of the elemental analysis are shown below.

Elemental analysis (%):

Calcd.: C, 87.75; H, 7.37; N, 4.88

Found: C, 87.80; H, 7.33; N, 4.89

Example 4

Synthesis of N,N,N', N'-tetrakis(4-biphenylyl)-2,3-naphthylenediamine

According to the same manner as that described in Example 1 except for using 112.0 g of 4-iodobiphenyl represented by the formula (1G):

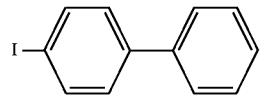

in place of m-iodotoluene represented by the formula (1B), the titled compound represented by the above formula (11-12) was obtained as an objective product (24.6 g, yield: 32.1%).

The results of the elemental analysis of the above compound are shown below.

Elemental analysis (%),

Calcd.: C, 90.82; H, 5.52; N, 3.65

Found: C, 90.56; H, 5.65; N, 3.78

Example 5

Synthesis of N,N'-bis(3-methylphenyl)-N,N'-bis(4-ethylbiphenyl-4-yl)-2,3-naphthylenediamine According to the same manner as that described in Example 3 except for using 15.4 g of 4-ethyl-4'-iodobiphenyl represented by the formula (1H):

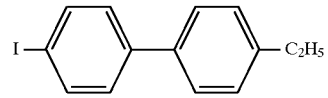

in place of 3-isopropyl-iodobenzene represented by the formula (1F), the titled compound represented by the above formula (11-13) was obtained as an objective product (9.82 g, yield: 23.1%).

The results of the elemental analysis of the above compound are shown below.

Elemental analysis (%):

Calcd.: C, 90.30; H, 6.40; N, 3.29

Found: C, 90.21; H, 6.45; N, 3.33

Example 6

Synthesis of N,N,N',N'-tetrakis(3-methylphenyl)-1,3-naphthylenediamine

According to the same manner as that described in Example 1 except for using 15.8 g of 1,3-naphthylenediamine represented by the formula (1I):

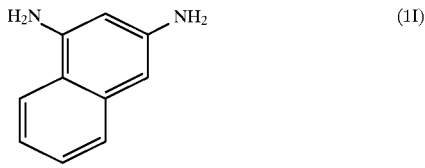

in place of 2,3-naphthylenediamine represented by the formula (1A), the titled compound represented by the above formula (13-2) was obtained as an objective product (14.7 g, yield: 28.3%).

The results of the elemental analysis of the above compound are shown below.

Elemental analysis (%):

Calcd.: C, 87.98; H, 6.61; N, 5.40

Found: C, 87.78; H, 6.66; N, 5.55

Example 7

Synthesis of N,N'-bis(3-methylphenyl)-N,N'-bis(3-isopropylphenyl)-1,3-naphthylenediamine According to the same manner as that described in Example 3 except for using 12.1 g of N,N'-diacetyl-1,3-naphthylenediamine represented by the formula (1J):

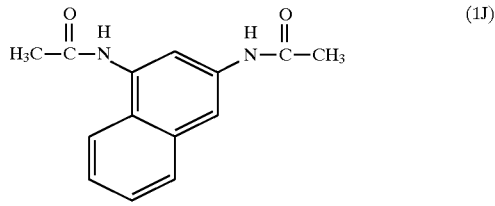

in place of N,N'-diacetyl-2,3-naphthylenediamine represented by the formula (1D), the titled compound represented by the above formula (13-7) was obtained as an objective product (5.72 g, yield: 19.9%).

The results of the elemental analysis of the above compound are shown below.

Elemental analysis (%):

Calcd.: C, 87.75; H, 7.37; N, 4.88

Found: C, 87.69; H, 7.25; N, 4.94

Example 8

Synthesis of N,N'-bis(4-methylphenyl)-N,N'-bis(4'-ethylbiphenyl-4-yl)-1,3-naphthylenediamine According to the same manner as that described in Example 3 except for using 12.1 g of N,N'-diacetyl-1,3-naphthylenediamine represented by the formula (1J) in place of N,N'-diacetyl-2,3-naphthylenediamine represented by the formula (1D), using 21.8 g of p-iodotoluene represented by the formula (1K):

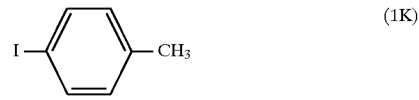

in place of m-iodotoluene represented by the formula (1B) and using 15.4 g of 4-ethyl-4'-iodobiphenyl represented by the formula (1H) in place of 3-isopropyl-iodobenzene represented by the formula (1F), the titled compound represented by the above formula (13-12) was obtained as an objective product (8.71 g, yield: 20.5%).

The results of the elemental analysis of the above compound are shown below.

Elemental analysis (%):

Calcd.: C, 90.30; H, 6.40; N, 3.29

Found: C, 90.39; H, 6.45; N, 3.25

Examples 9 to 15 and Comparative Example 1

(Single-layer type photosensitive material for digital light source)

Parts by weight of X-type metal-free phthalocyanine represented by the formula (8-1):

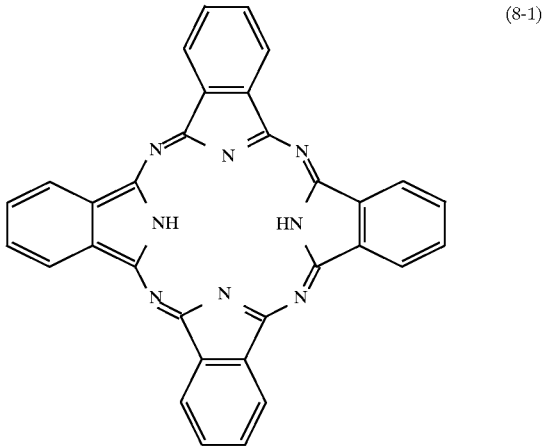

as the electric charge generating material, 100 parts by weight of an electric charge transferring material and 100 parts by weight of polycarbonate as the binding resin were mixed/dispersed with 800 parts by weight of tetrahydrofuran as the solvent using a ball mill for 50 hours to prepare a coating solution for single-layer type electrophotosensitive layer. Then, this coating solution was applied on an aluminum tube as the conductive substrate by a dip coating method, followed by hot-air drying at 110° C. for 30 minutes to produce a single-layer type electrophotosensitive material for digital light source, which has a single-layer type photosensitive layer of 25 μm in film thickness.

The electric charge transferring material used in the Examples is a naphthylenediamine derivative of the present invention. The respective compounds of the naphthylenediamine derivative are shown by the number of the above compounds in Table 1. In addition, the electric charge transferring material used in the Comparative Example is a m-phenylenediamine derivative represented by the above formula (71-1).

The electrophotosensitive materials of the above Examples and Comparative Example were subjected to the following initial electric characteristics test (I) and electric characteristics test (I) after repeated exposure, and their characteristics were evaluated.

Initial electric characteristics test (I)

By using a drum sensitivity tester manufactured by GENTEC Co., a voltage was applied on the surface of the electrophotosensitive materials of the respective Examples and Comparative Examples to charge the surface at +700±20V, and a surface potential $V_0$ (V) was measured. Then, monochromatic light having a wavelength of 780 nm (half-width: 20 nm) and a light intensity of 10 $\mu J/cm^2$ from white light of a halogen lamp as an exposure light source through a band-pass filter was irradiated on the surface of the electrophotosensitive material for 1.5 seconds (irradiation time) and the time which is necessary for the above surface potential to be reduced to half was measured, thereby calculating a half-life exposure $E_{1/2}$ ($\mu J/cm^2$). Further, a surface potential at the time at which 0.5 seconds has passed since the beginning of exposure was measured as a residual potential $V_r$ (V).

Electric characteristics test (I) after repeated exposure

An electrophotosensitive material of the respective Examples and Comparative Examples was fit with a laser beam printer (Model TC-650, manufactured by Mita Industrial Co., Ltd.) and, after the image was formed 10,000 times, a surface potential $V_0$ (V) and a residual potential $V_r$ (V) were measured using the above drum sensitivity tester according to the same manner as that described above. Then, a change in measured value from the initial value (i.e. $\Delta V_0$ (V) and $\Delta V_r$ (V)) was determined.

The results are shown in Table 1.

In the following tables, "CTM" denotes "charge transferring material."

TABLE 1

| | | Initial Characteristics | | | After Repeating | |
|---|---|---|---|---|---|---|
| | CTM | $V_0$ | Vr | $E_{1/2}$ | $\Delta V_0$ | $\Delta Vr$ |
| Ex. 9 | 11-2 | 706 | 49 | 1.35 | −15 | +5 |
| Ex. 10 | 11-6 | 701 | 54 | 1.36 | −20 | +4 |
| Ex. 11 | 11-8 | 702 | 48 | 1.40 | −25 | +7 |
| Ex. 12 | 11-13 | 700 | 51 | 1.36 | −24 | +9 |
| Ex. 13 | 13-2 | 702 | 42 | 1.36 | −20 | +9 |
| Ex. 14 | 13-7 | 700 | 53 | 1.37 | −15 | +5 |
| Ex. 15 | 13-12 | 703 | 49 | 1.39 | −25 | +8 |
| Comp. Ex. 1 | 71-1 | 700 | 130 | 2.45 | −220 | +55 |

Examples 16 to 21 and Comparative Example 2
(Single-layer type electrophotosensitive material for analogue light source)

According to the same manner as that described in Examples 9 to 15 and Comparative Example 1 except for using 5 parts by weight of a perylene pigment represented by the formula (9-1):

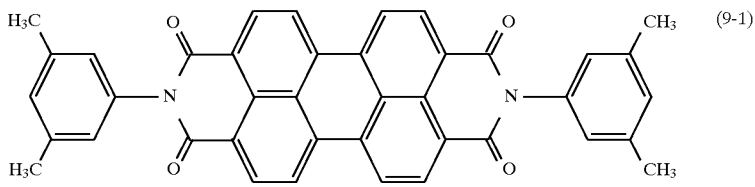

as the electric charge generating material, a single-layer type electrophotosensitive material for analogue light source was produced.

The electric charge transferring materials used in the Examples and Comparative Examples are shown by the number of the above compounds in Table 2, according to the same manner as that described above.

The electrophotosensitive materials of the above Examples and Comparative Examples were subjected to the following initial electric characteristics test (II) and electric characteristics test (II) after repeated exposure, and their characteristics were evaluated.

Initial electric characteristics test (II)

By using a drum sensitivity tester manufactured by GENTEC Co., a voltage was applied on the surface of the electrophotosensitive materials of the respective Examples and Comparative Examples to charge the surface at +700 V±20V, and a surface potential $V_0$ (V) was measured. Then, white light from a halogen lamp as an exposure light source (light intensity: 10 lux) was irradiated on the surface of the electrophotosensitive material for 1.5 seconds (irradiation time) and the time which is necessary for the above surface potential to be reduced to half was measured, thereby calculating a half-life exposure $E_{1/2}$ (lux·second). Further, a surface potential at the time at which 0.5 seconds has passed since the beginning of exposure was measured as a residual potential $V_r$ (V).

Electric characteristics test (II) after repeated exposure

An electrophotosensitive material of the respective Examples and Comparative Examples was fit with an electrostatic copying machine (Model DC2556, manufactured by Mita Industrial Co., Ltd.) and, after the image was formed 10,000 times, a surface potential $V_0$ (V) and a residual potential $V_r$ (V) were measured using the above drum sensitivity tester according to the same manner as that described above. Then, a change in measured value from the initial value (i.e. $\Delta V_0$ (V) and $\Delta V_r$ (V)) was determined.

The results are shown in Table 2.

TABLE 2

| | | Initial Characteristics | | | After Repeating | |
|---|---|---|---|---|---|---|
| | CTM | $V_0$ | Vr | $E_{1/2}$ | $\Delta V_0$ | $\Delta Vr$ |
| Ex. 16 | 11-2 | 700 | 125 | 1.75 | −15 | +15 |
| Ex. 17 | 11-8 | 701 | 135 | 1.73 | −20 | +10 |
| Ex. 18 | 11-13 | 699 | 135 | 1.79 | −30 | +10 |
| Ex. 19 | 13-2 | 700 | 130 | 1.76 | −15 | +10 |
| Ex. 20 | 13-7 | 701 | 136 | 1.75 | −20 | +15 |
| Ex. 21 | 13-10 | 695 | 134 | 1.80 | −25 | +15 |
| Comp. Ex. 2 | 71-1 | 703 | 195 | 2.48 | −90 | +55 |

Examples 22 to 28 and Comparative Example 3
(Single-layer type electrophotosensitive material for analogue light source)

According to the same manner as that described in Examples 9 to 15 and Comparative Example 1 except for using 5 parts by weight of a bisazo pigment represented by the formula (10-1):

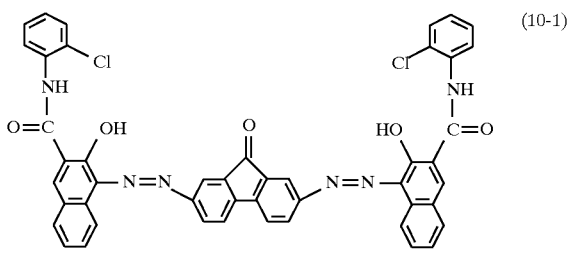
(10-1)

as the electric charge generating material, a single-layer type electrophotosensitive material for analogue light source was produced.

The electric charge transferring materials used in the Examples and Comparative Examples are shown by the number of the above compounds in Table 3, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 3.

TABLE 3

| | | Initial Characteristics | | | After Repeating | |
|---|---|---|---|---|---|---|
| | CTM | $V_o$ | Vr | $E_{1/2}$ | $\Delta V_o$ | $\Delta Vr$ |
| Ex. 22 | 11-2 | 698 | 95 | 1.35 | −20 | +5 |
| Ex. 23 | 11-8 | 702 | 70 | 1.32 | −30 | +15 |
| Ex. 24 | 11-13 | 698 | 65 | 1.48 | −20 | +15 |
| Ex. 25 | 11-6 | 701 | 49 | 1.30 | −15 | ±0 |
| Ex. 26 | 13-2 | 700 | 96 | 1.34 | −21 | +5 |
| Ex. 27 | 13-7 | 706 | 69 | 1.32 | −29 | +20 |
| Ex. 28 | 13-10 | 698 | 67 | 1.48 | −20 | +10 |
| Comp. Ex. 3 | 71-1 | 701 | 124 | 1.60 | −215 | +45 |

Examples 29 to 38 and Comparative Example 4
(Single-layer type electrophotosensitive material for analogue light source)

According to the same manner as that described in Examples 9 to 15 and Comparative Example 1 except for using 5 parts by weight of a bisazo pigment represented by the formula (10-2):

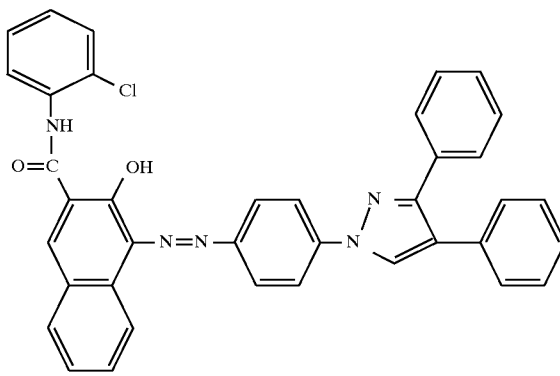
(10-2)

as the electric charge generating material, a single-layer type electrophotosensitive material for analogue light source was produced.

The electric charge transferring materials used in the Examples and Comparative Examples are shown by the number of the above compounds in Table 4, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 4.

TABLE 4

| | | Initial Characteristics | | | After Repeating | |
|---|---|---|---|---|---|---|
| | CTM | $V_o$ | Vr | $E_{1/2}$ | $\Delta V_o$ | $\Delta Vr$ |
| Ex. 29 | 11-2 | 695 | 80 | 1.30 | −20 | +5 |
| Ex. 30 | 11-8 | 699 | 69 | 1.45 | −40 | +15 |
| Ex. 31 | 11-13 | 698 | 52 | 1.40 | −15 | +20 |
| Ex. 32 | 11-6 | 702 | 44 | 1.43 | −55 | +10 |
| Ex. 33 | 11-14 | 702 | 43 | 1.45 | −45 | +15 |
| Ex. 34 | 11-18 | 705 | 42 | 1.40 | −40 | +15 |
| Ex. 35 | 11-20 | 704 | 45 | 1.46 | −10 | +15 |
| Ex. 36 | 13-2 | 695 | 82 | 1.30 | −15 | +5 |
| Ex. 37 | 13-7 | 700 | 70 | 1.42 | −45 | +10 |
| Ex. 38 | 13-10 | 698 | 56 | 1.42 | −20 | +20 |
| Comp. Ex. 4 | 71-1 | 702 | 131 | 1.72 | −180 | +55 |

Examples 39 to 45 and Comparative Example 5

(Single-layer type electrophotosensitive material for analogue light source)

According to the same manner as that described in Examples 9 to 15 and Comparative Example 1 except for using 5 parts by weight of a bisazo pigment represented by the formula (10-3):

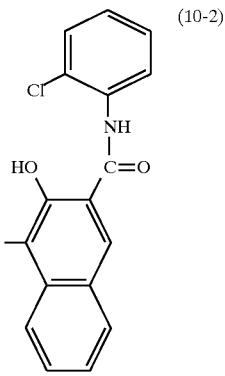

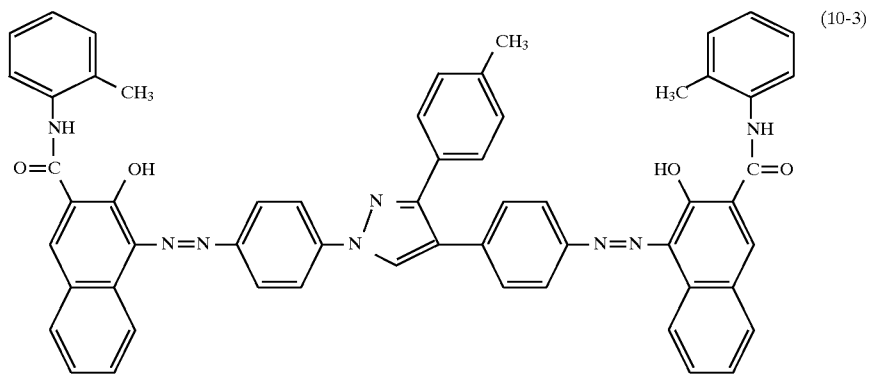

(10-3)

as the electric charge generating material, a single-layer type electrophotosensitive material for analogue light source was produced.

using 5 parts by weight of a bisazo pigment represented by the formula (10-4):

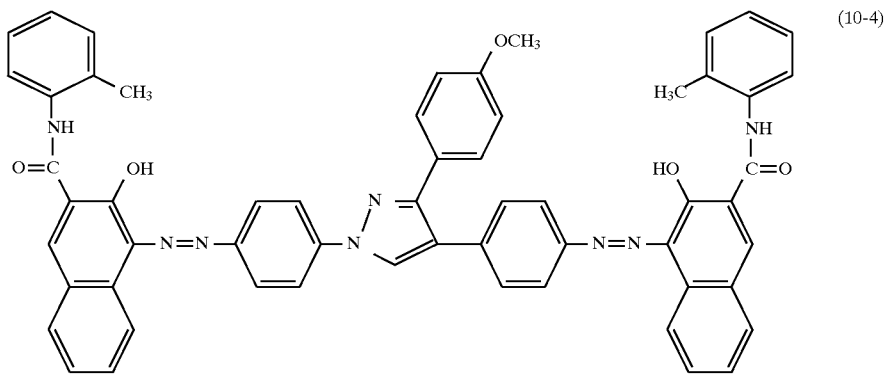

(10-4)

as the electric charge generating material, a single-layer type electrophotosensitive material for analogue light source was produced.

The electric charge transferring materials used in the Examples and Comparative Examples are shown by the number of the above compounds in Table 5, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 5.

TABLE 5

| | | Initial Characteristics | | | After Repeating | |
|---|---|---|---|---|---|---|
| | CTM | $V_0$ | Vr | $E_{1/2}$ | $\Delta V_0$ | $\Delta Vr$ |
| Ex. 39 | 11-2 | 698 | 75 | 1.29 | −30 | +20 |
| Ex. 40 | 11-8 | 698 | 60 | 1.50 | −35 | +20 |
| Ex. 41 | 11-13 | 701 | 54 | 1.40 | −10 | +35 |
| Ex. 42 | 11-6 | 702 | 45 | 1.50 | −20 | +15 |
| Ex. 43 | 13-2 | 698 | 77 | 1.30 | −30 | +10 |
| Ex. 44 | 13-7 | 698 | 62 | 1.48 | −40 | +25 |
| Ex. 45 | 13-10 | 700 | 50 | 1.41 | −10 | +40 |
| Comp. Ex. 5 | 71-1 | 703 | 124 | 1.62 | −165 | +40 |

Examples 46 to 51 and Comparative Example 6
(Single-layer type electrophotosensitive material for analogue light source)

According to the same manner as that described in Examples 9 to 15 and Comparative Example 1 except for The electric charge transferring materials used in the Examples and Comparative Examples are shown by the number of the above compounds in Table 6, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 6.

TABLE 6

| | | Initial Characteristics | | | After Repeating | |
|---|---|---|---|---|---|---|
| | CTM | $V_0$ | Vr | $E_{1/2}$ | $\Delta V_0$ | $\Delta Vr$ |
| Ex. 46 | 11-2 | 698 | 35 | 1.14 | −35 | +5 |
| Ex. 47 | 11-8 | 700 | 45 | 1.26 | −30 | +10 |
| Ex. 48 | 11-13 | 705 | 31 | 1.15 | −10 | +20 |
| Ex. 49 | 13-2 | 700 | 34 | 1.15 | −40 | +5 |
| Ex. 50 | 13-7 | 702 | 45 | 1.30 | −30 | +10 |
| Ex. 51 | 13-10 | 705 | 33 | 1.17 | −15 | +20 |
| Comp. Ex. 6 | 71-1 | 702 | 110 | 1.46 | −165 | +50 |

Examples 52 to 57 and Comparative Example 7
(Single-layer type electrophotosensitive material for analogue light source)

According to the same manner as that described in Examples 9 to 15 and Comparative Example 1 except for using 5 parts by weight of a bisazo pigment represented by the formula (10-5):

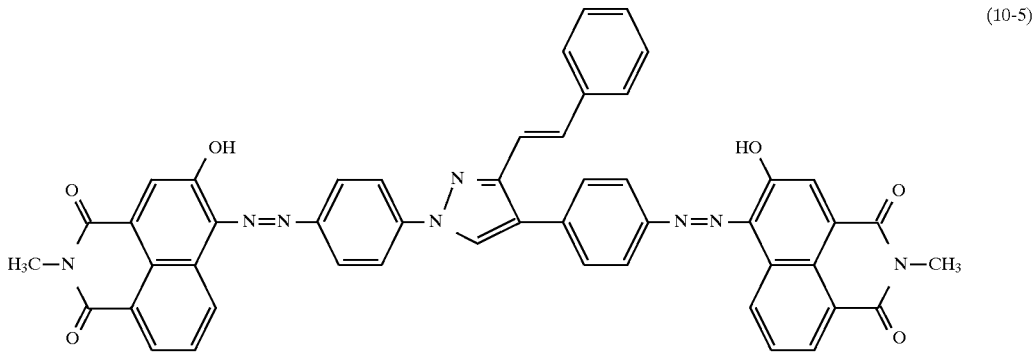

(10-5)

as the electric charge generating material, a single-layer type electrophotosensitive material for analogue light source was produced.

The electric charge transferring materials used in the Examples and Comparative Examples are shown by the number of the above compounds in Table 7, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 7.

as the electric charge generating material, a single-layer type electrophotosensitive material for analogue light source was produced.

The electric charge transferring materials used in the Examples and Comparative Examples are shown by the number of the compounds in Table 8, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 8.

TABLE 7

|  |  | Initial Characteristics | | | After Repeating | |
|---|---|---|---|---|---|---|
|  | CTM | $V_0$ | Vr | $E_{1/2}$ | $\Delta V_0$ | $\Delta Vr$ |
| Ex. 52 | 11-2 | 693 | 80 | 1.30 | −40 | +10 |
| Ex. 53 | 11-8 | 701 | 70 | 1.59 | −20 | +10 |
| Ex. 54 | 11-13 | 706 | 53 | 1.32 | −5 | +25 |
| Ex. 55 | 13-2 | 693 | 82 | 1.30 | −40 | +15 |
| Ex. 56 | 13-7 | 701 | 72 | 1.60 | −25 | +15 |
| Ex. 57 | 13-10 | 704 | 55 | 1.30 | −5 | +20 |
| Comp. Ex. 7 | 71-1 | 699 | 138 | 1.77 | −250 | +40 |

TABLE 8

|  |  | Initial Characteristics | | | After Repeating | |
|---|---|---|---|---|---|---|
|  | CTM | $V_0$ | Vr | $E_{1/2}$ | $\Delta V_0$ | $\Delta Vr$ |
| Ex. 58 | 11-2 | 700 | 50 | 1.35 | −20 | ±0 |
| Ex. 59 | 11-8 | 702 | 56 | 1.50 | −25 | ±0 |
| Ex. 60 | 11-13 | 700 | 50 | 1.43 | −50 | +10 |
| Ex. 61 | 11-6 | 705 | 50 | 1.20 | −30 | +20 |
| Ex. 62 | 13-2 | 701 | 50 | 1.35 | −25 | ±0 |
| Ex. 63 | 13-7 | 702 | 58 | 1.52 | −25 | ±0 |
| Ex. 64 | 13-10 | 702 | 54 | 1.42 | −50 | +15 |
| Comp. Ex. 8 | 11-1 | 698 | 140 | 2.17 | −225 | +65 |

Examples 58 to 64 and Comparative Example 8
(Single-layer type electrophotosensitive material for analogue light source)

According to the same manner as that described in Examples 9 to 15 and Comparative Example 1 except for using 5 parts by weight of a bisazo pigment represented by the formula (10-6):

Examples 65 to 70 and Comparative Example 9
(Single-layer type electrophotosensitive material for analogue light source)

According to the same manner as that described in Examples 9 to 15 and Comparative Example 1 except for using 5 parts by weight of a bisazo pigment represented by the formula (10-7):

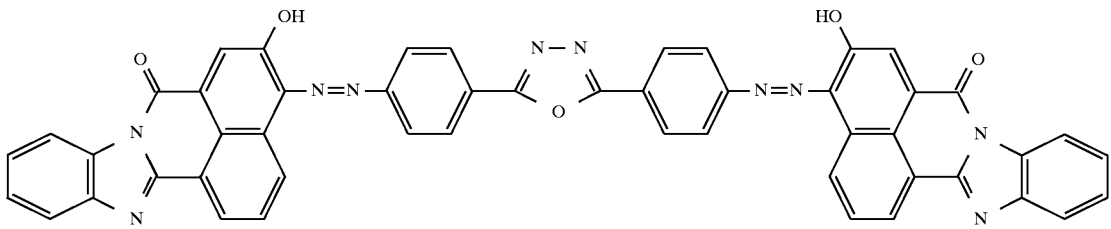

(10-6)

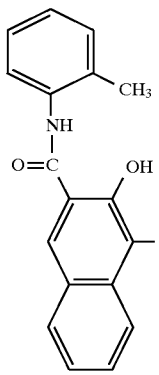
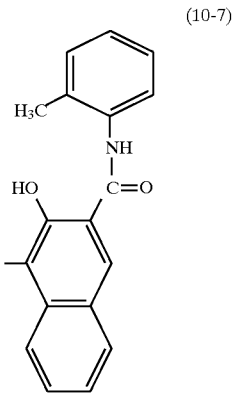

(10-7)

as the electric charge generating material, a single-layer type electrophotosensitive material for analogue light source was produced.

The electric charge transferring materials used in the Examples and Comparative Examples are shown by the number of the above compounds in Table 9, according to the same manner as that described above.

The electrophotosensitive materials of the above Examples and Comparative Examples were subjected to the above initial electric characteristics test (II) and electric characteristics test (II) after repeated exposure, and their characteristics were evaluated. The results are shown in Table 9.

TABLE 9

| | | Initial Characteristics | | | After Repeating | |
|---|---|---|---|---|---|---|
| | CTM | $V_o$ | Vr | $E_{1/2}$ | $\Delta V_o$ | $\Delta Vr$ |
| Ex. 65 | 11-2 | 705 | 52 | 1.30 | −15 | +5 |
| Ex. 66 | 11-8 | 703 | 60 | 1.35 | −15 | ±0 |
| Ex. 67 | 11-13 | 701 | 65 | 1.45 | −15 | ±0 |
| Ex. 68 | 13-2 | 705 | 53 | 1.29 | −17 | +5 |
| Ex. 69 | 13-7 | 703 | 62 | 1.37 | −15 | ±0 |
| Ex. 70 | 13-10 | 701 | 69 | 1.47 | −20 | ±0 |
| Comp. Ex. 9 | 71-1 | 695 | 138 | 1.98 | −250 | +50 |

Examples 71 to 77 and Comparative Example 10 (Multi-layer type electrophotosensitive material for digital light source)

2.5 Parts by weight of X-type metal-free phthalocyanine represented by the above formula (8-1) as the electric charge generating material and 1 part by weight of polyvinyl butyral as the binding resin were mixed/dispersed with 15 parts by weight of tetrahydrofuran as the solvent using a ball mill to prepare a coating solution for electric charge generating layer. Then, this coating solution was applied on an aluminum tube as the conductive substrate by a dip coating method, followed by hot-air drying at 110° C. for 30 minutes to form an electric charge generating layer of 0.5 μm in film thickness.

Then, 1 part by weight of an electric charge transferring material and 1 part by weight of polycarbonate as the binding resin were mixed/dispersed with 10 parts by weight of tetrahydrofuran as the solvent using a ball mill to prepare a coating solution for electric charge transferring layer. Then, this coating solution was applied on the electric charge generating layer by a dip coating method, followed by hot-air drying at 110° C. for 30 minutes to form an electric charge transferring layer of 20 μm in film thickness, thereby affording a multi-layer type electrophotosensitive material for digital light source.

The electric charge transferring materials used in the Examples and Comparative Examples are shown by the number of the above compounds in Table 10 according to the same manner as that described above.

The electrophotosensitive materials of the above Examples and Comparative Examples were subjected to the following initial electric characteristics test (III) and electric characteristics test (III) after repeated exposure, and their characteristics were evaluated.

Initial electric characteristics test (III)

By using a drum sensitivity tester manufactured by GENTEC Co., a voltage was applied on the surface of the electrophotosensitive materials of the respective Examples and Comparative Examples to charge the surface at −700±20V, and a surface potential $V_0$ (V) was measured. Then, monochromatic light having a wavelength of 780 nm (half-width: 20 nm) and a light intensity of 10 μJ/cm from white light of a halogen lamp as an exposure light source through a band-pass filter was irradiated on the surface of the electrophotosensitive material for 1.5 seconds. (irradiation time) and the time which is necessary for the above surface potential to be reduced to half was measured, thereby calculating a half-life exposure $E_{1/2}$ (μJ/cm$^2$). Further, a surface potential at the time at which 0.5 seconds has passed since the beginning of exposure was measured as a residual potential $V_r$ (V).

Electric characteristics test (III) after repeated exposure

An electrophotosensitive material of the respective Examples and Comparative Examples was fit with a laser beam printer (Model LP-2080, manufactured by Mita Industrial Co., Ltd.) and, after the image was formed 10,000 times, a surface potential $V_0$ (V) and a residual potential $V_r$ (V) were measured using the above drum sensitivity tester according to the same manner as that described above. Then, a change in measured value from the initial value (i.e. $\Delta V_0$ (V) and $\Delta V_r$ (V)) was determined.

The results are shown in Table 10.

TABLE 10

| | | Initial Characteristics | | | After Repeating | |
|---|---|---|---|---|---|---|
| | CTM | $V_o$ | Vr | $E_{1/2}$ | $\Delta V_o$ | $\Delta Vr$ |
| Ex. 71 | 11-2 | −700 | −11 | 0.41 | −40 | +5 |
| Ex. 72 | 11-6 | −700 | −12 | 0.42 | −45 | +5 |
| Ex. 73 | 11-8 | −701 | −15 | 0.48 | −20 | +10 |
| Ex. 74 | 11-13 | −702 | −13 | 0.65 | −15 | +15 |

TABLE 10-continued

| | CTM | Initial Characteristics | | | After Repeating | |
| | | $V_0$ | Vr | $E_{1/2}$ | $\Delta V_0$ | $\Delta Vr$ |
|---|---|---|---|---|---|---|
| Ex. 75 | 13-2 | −701 | −13 | 0.41 | −40 | +10 |
| Ex. 76 | 13-7 | −700 | −12 | 0.44 | −40 | +5 |
| Ex. 77 | 13-12 | −700 | −14 | 0.49 | −25 | +20 |
| Comp. Ex. 10 | 71-1 | −695 | −22 | 1.85 | −55 | +35 |

Examples 78 to 83 and Comparative Example 11
(Multi-layer type electrophotosensitive material for analogue light source)

According to the same manner as that described in Examples 71 to 77 and Comparative Example 10 except for using 2.5 parts by weight of the perylene pigment represented by the above formula (9-1) as the electric charge generating material, a multi-layer type electrophotosensitive material for analogue light source was produced.

The electric charge transferring materials used in the Examples and Comparative Examples are shown by the number of the above compounds in Table 11, according to the same manner as that described above.

The electrophotosensitive materials of the above Examples and Comparative Examples were subjected to the following initial electric characteristics test (IV) and electric characteristics test (IV) after repeated exposure, and their characteristics were evaluated.

Initial electric characteristics test (IV)

By using a drum sensitivity tester manufactured by GENTEC Co., a voltage was applied on the surface of the electrophotosensitive materials of the respective Examples and Comparative Examples to charge the surface at −700 V±20V, and a surface potential $V_0$ (V) was measured. Then, white light from a halogen lamp as an exposure light source (light intensity: 10 lux) was irradiated on the surface of the electrophotosensitive material for 1.5 seconds (irradiation time) and the time which is necessary for the above surface potential to be reduced to half was measured, thereby calculating a half-life exposure $E_{1/2}$ (lux·second). Further, a surface potential at the time at which 0.5 seconds has passed since the beginning of exposure was measured as a residual potential $V_r$ (V).

Electric characteristics test (IV) after repeated exposure

An electrophotosensitive material of the respective Examples and Comparative Examples was fit with an electrostatic copying machine (Model DC2556 which is reconstructed for the negative charging type, manufactured by Mita Industrial Co., Ltd.) and, after the image was formed 10,000 times, a surface potential $V_0$ (V) and a residual potential $V_r$ (V) were measured using the above drum sensitivity tester according to the same manner as that described above. Then, a change in measured value from the initial value (i.e. $\Delta V_0$ (V) and $\Delta V_r$ (V)) was determined.

The results are shown in Table 11.

TABLE 11

| | CTM | Initial Characteristics | | | After Repeating | |
| | | $V_0$ | Vr | $E_{1/2}$ | $\Delta V_0$ | $\Delta Vr$ |
|---|---|---|---|---|---|---|
| Ex. 78 | 11-2 | −702 | −130 | 1.93 | −65 | +20 |
| Ex. 79 | 11-8 | −698 | −134 | 1.92 | −75 | +10 |
| Ex. 80 | 11-13 | −689 | −135 | 1.96 | −60 | +5 |
| Ex. 81 | 13-2 | −700 | −125 | 1.90 | −70 | +15 |
| Ex. 82 | 13-7 | −699 | −135 | 1.90 | −80 | +10 |
| Ex. 83 | 13-12 | −698 | −135 | 1.96 | −60 | +5 |
| Comp. Ex. 11 | 71-1 | −699 | −157 | 2.53 | −40 | +65 |

Examples 84 to 90 and Comparative Example 12
(Multi-layer type electrophotosensitive material for analogue light source)

According to the same manner as that described in Examples 71 to 77 and Comparative Example 10 except for using 2.5 parts by weight of the bisazo pigment represented by the above formula (10-1) as the electric charge generating material, a multi-layer type electrophotosensitive material for analogue light source was produced.

The electric charge transferring materials used in the Examples and Comparative Examples are shown by the number of the above compounds in Table 12, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 12.

TABLE 12

| | CTM | Initial Characteristics | | | After Repeating | |
| | | $V_0$ | Vr | $E_{1/2}$ | $\Delta V_0$ | $\Delta Vr$ |
|---|---|---|---|---|---|---|
| Ex. 84 | 11-2 | −702 | −25 | 0.51 | −55 | +15 |
| Ex. 85 | 11-8 | −699 | −29 | 0.53 | −70 | +10 |
| Ex. 86 | 11-13 | −697 | −25 | 0.40 | −20 | ±0 |
| Ex. 87 | 11-6 | −705 | −27 | 0.36 | −45 | +5 |
| Ex. 88 | 13-2 | −701 | −26 | 0.55 | −55 | +20 |
| Ex. 89 | 13-7 | −701 | −30 | 0.55 | −70 | +15 |
| Ex. 90 | 13-12 | −697 | −25 | 0.40 | −20 | ±0 |
| Comp. Ex. 12 | 71-1 | −704 | −90 | 1.53 | −140 | +45 |

Examples 91 to 100 and Comparative Example 13
(Multi-layer type electrophotosensitive material for analogue light source)

According to the same manner as that described in Examples 71 to 77 and Comparative Example 10 except for using 2.5 parts by weight of the bisazo pigment represented by the above formula (10-2) as the electric charge generating material, a multi-layer type electrophotosensitive material for analogue light source was produced.

The electric charge transferring materials used in the Examples and Comparative Examples are shown by the number of the above compounds in Table 13, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 13.

TABLE 13

| | CTM | Initial Characteristics | | | After Repeating | |
| --- | --- | --- | --- | --- | --- | --- |
| | | $V_0$ | Vr | $E_{1/2}$ | $\Delta V_0$ | $\Delta Vr$ |
| Ex. 91 | 11-2 | −704 | −26 | 0.56 | −45 | +15 |
| Ex. 92 | 11-8 | −699 | −24 | 0.55 | −65 | ±0 |
| Ex. 93 | 11-13 | −698 | −25 | 0.42 | −50 | +15 |
| Ex. 94 | 11-6 | −762 | −23 | 0.34 | −20 | ±0 |
| Ex. 95 | 11-14 | −704 | −22 | 0.43 | −50 | +10 |
| Ex. 96 | 11-18 | −703 | −29 | 0.46 | −55 | +15 |
| Ex. 97 | 11-20 | −702 | −29 | 0.44 | −30 | +5 |
| Ex. 98 | 13-2 | −702 | −27 | 0.57 | −40 | +15 |
| Ex. 99 | 13-7 | −701 | −30 | 0.55 | −65 | ±0 |
| Ex. 100 | 13-12 | −698 | −30 | 0.42 | −50 | +15 |
| Comp. Ex. 13 | 71-1 | −697 | −125 | 1.65 | −175 | +50 |

Examples 101 to 107 and Comparative Example 14 (Multi-layer type electrophotosensitive material for analogue light source)

According to the same manner as that described in Examples 71 to 77 and Comparative Example 10 except for using 2.5 parts by weight of the bisazo pigment represented by the above formula (10-3) as the electric charge generating material, a multi-layer type electrophotosensitive material for analogue light source was produced.

The electric charge transferring materials used in the Examples and Comparative Examples are shown by the number of the above compounds in Table 14, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 14.

TABLE 14

| | CTM | Initial Characteristics | | | After Repeating | |
| --- | --- | --- | --- | --- | --- | --- |
| | | $V_0$ | Vr | $E_{1/2}$ | $\Delta V_0$ | $\Delta Vr$ |
| Ex. 101 | 11-2 | −704 | −28 | 0.52 | −60 | +20 |
| Ex. 102 | 11-8 | −700 | −24 | 0.56 | −60 | ±0 |
| Ex. 103 | 11-13 | −697 | −21 | 0.43 | −50 | +20 |
| Ex. 104 | 11-6 | −704 | −27 | 0.45 | −50 | +20 |
| Ex. 105 | 13-2 | −703 | −29 | 0.50 | −55 | +20 |
| Ex. 106 | 13-7 | −700 | −24 | 0.56 | −60 | ±0 |
| Ex. 107 | 13-12 | −699 | −21 | 0.43 | −50 | +20 |
| Comp. Ex. 14 | 71-1 | −701 | −104 | 1.74 | −125 | +40 |

Examples 108 to 113 and Comparative Example 15 (Multi-layer type electrophotosensitive material for analogue light source)

According to the same manner as that described in Examples 71 to 77 and Comparative Example 10 except for using 2.5 parts by weight of the bisazo pigment represented by the above formula (10-4) as the electric charge generating material, a multi-layer type electrophotosensitive material for analogue light source was produced.

The electric charge transferring materials used in the Examples and Comparative Examples are shown by the number of the above compounds in Table 15, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 15.

TABLE 15

| | CTM | Initial Characteristics | | | After Repeating | |
| --- | --- | --- | --- | --- | --- | --- |
| | | $V_0$ | Vr | $E_{1/2}$ | $\Delta V_0$ | $\Delta Vr$ |
| Ex. 108 | 11-2 | −704 | −12 | 0.38 | −40 | +10 |
| Ex. 109 | 11-8 | −701 | −13 | 0.42 | −60 | −5 |
| Ex. 110 | 11-13 | −699 | −14 | 0.35 | −25 | +15 |
| Ex. 111 | 13-2 | −703 | −15 | 0.40 | −50 | +20 |
| Ex. 112 | 13-7 | −702 | −15 | 0.42 | −60 | −5 |
| Ex. 113 | 13-12 | −699 | −15 | 0.35 | −25 | +15 |
| Comp. Ex. 15 | 71-1 | −701 | −75 | 1.42 | −110 | +35 |

Examples 114 to 119 and Comparative Example 16 (Multi-layer type electrophotosensitive material for analogue light source)

According to the same manner as that described in Examples 71 to 77 and Comparative Example 10 except for using 2.5 parts by weight of the bisazo pigment represented by the above formula (10-5) as the electric charge generating material, a multi-layer type electrophotosensitive material for analogue light source was produced.

The electric charge transferring materials used in the Examples and Comparative Examples are shown by the number of the above compounds in Table 16, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 16.

TABLE 16

| | CTM | Initial Characteristics | | | After Repeating | |
| --- | --- | --- | --- | --- | --- | --- |
| | | $V_0$ | Vr | $E_{1/2}$ | $\Delta V_0$ | $\Delta Vr$ |
| Ex. 114 | 11-2 | −702 | −31 | 0.86 | −60 | +20 |
| Ex. 115 | 11-8 | −704 | −32 | 0.86 | −55 | +10 |
| Ex. 116 | 11-13 | −701 | −35 | 0.56 | −50 | +10 |
| Ex. 117 | 13-2 | −700 | −30 | 0.89 | −55 | +10 |
| Ex. 118 | 13-7 | −703 | −30 | 0.81 | −55 | +10 |
| Ex. 119 | 13-12 | −701 | −35 | 0.56 | −50 | +10 |
| Comp. Ex. 16 | 71-1 | −700 | −135 | 1.95 | −190 | +60 |

Examples 120 to 126 and Comparative Example 17 (Multi-layer type electrophotosensitive material for analogue light source)

According to the same manner as that described in Examples 71 to 77 and Comparative Example 10 except for using 2.5 parts by weight of the bisazo pigment represented by the above formula (10-6) as the electric charge generating material, a multi-layer type electrophotosensitive material for analogue light source was produced.

The electric charge transferring materials used in the Examples and Comparative Examples are shown by the number of the above compounds in Table 17, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 17.

TABLE 17

|  | CTM | Initial Characteristics | | | After Repeating | |
|---|---|---|---|---|---|---|
|  |  | $V_0$ | Vr | $E_{1/2}$ | $\Delta V_0$ | $\Delta Vr$ |
| Ex. 120 | 11-2 | −699 | −34 | 0.81 | −55 | +5 |
| Ex. 121 | 11-8 | −700 | −30 | 0.73 | −20 | +15 |
| Ex. 122 | 11-13 | −702 | −34 | 0.55 | −55 | +35 |
| Ex; 123 | 11-6 | −701 | −35 | 0.62 | −50 | +35 |
| Ex. 124 | 13-2 | −700 | −35 | 0.83 | −55 | +5 |
| Ex. 125 | 13-7 | −700 | −25 | 0.73 | −20 | +15 |
| Ex. 126 | 13-12 | −700 | −34 | 0.55 | −55 | +35 |
| Comp. Ex. 17 | 71-1 | −699 | −134 | 1.82 | −200 | +70 |

Examples 127 to 132 and Comparative Example 18 (Multi-layer type electrophotosensitive material for analogue light source)

According to the same manner as that described in Examples 71 to 77 and Comparative Example 10 except for using 2.5 parts by weight of the bisazo pigment represented by the above formula (10-7) as the electric charge generating material, a multi-layer type electrophotosensitive material for analogue light source was produced.

The electric charge transferring materials used in the Examples and Comparative Examples are shown by the number of the above compounds in Table 18, according to the same manner as that described above.

The electrophotosensitive materials of the above Examples and Comparative Examples were subjected to the above initial electric characteristics test (IV) and electric characteristics test (IV) after repeated exposure, and their characteristics were evaluated. The results are shown in Table 18.

TABLE 18

|  | CTM | Initial Characteristics | | | After Repeating | |
|---|---|---|---|---|---|---|
|  |  | $V_0$ | Vr | $E_{1/2}$ | $\Delta V_0$ | $\Delta Vr$ |
| Ex. 127 | 11-2 | −698 | −33 | 0.83 | −45 | ±0 |
| Ex. 128 | 11-8 | −702 | −29 | 0.59 | −25 | +15 |
| Ex. 129 | 11-13 | −703 | −34 | 0.53 | −55 | +34 |
| Ex. 130 | 13-2 | −699 | −30 | 0.84 | −40 | ±0 |
| Ex. 131 | 13-7 | −701 | −29 | 0.59 | −25 | +15 |
| Ex. 132 | 13-12 | −703 | −35 | 0.53 | −55 | +34 |
| Comp. Ex. 18 | 71-1 | −700 | −138 | 1.81 | −130 | +75 |

Examples 133 to 144
(Single-layer type electrophotosensitive material for digital light source)

According to the same manner as that described in Examples 9 to 15 except for using 5 parts by weight of X-type metal-free phthalocyanine represented by the above formula (8-1) as the electric charge generating material, 100 parts by weight of a naphthylenediamine derivative as the hole transferring material, 100 parts by weight of polycarbonate as the binding resin and 30 parts by weight (15 parts by weight, in case of Examples 135, 139 and 143) of a 2,4,7-trinitrofluorenonimine derivative as the electron transferring material, a single-layer type electrophotosensitive material for digital light source was produced.

The hole transferring materials and electron transferring materials used in the Examples are shown by the number of the above compounds in Table 19, according to the same manner as that described above.

The electrophotosensitive materials of the above respective Examples were subjected to the above initial electric characteristics test (I) and electric characteristics test (I) after repeated exposure, and their characteristics were evaluated. The results are shown in Table 19.

In the following tables, "HTM" and "ETM" denote "hole transferring material" and "electron transferring material", respectively.

TABLE 19

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 133 | 11-8 | 2-5 | 702 | 24 | 1.28 | −16 | +3 |
| Ex. 134 | 11-8 | 2-6 | 701 | 23 | 1.29 | −15 | +2 |
| Ex. 135 | 11-8 | 2-16 | 698 | 25 | 1.30 | −16 | +4 |
| Ex. 136 | 11-8 | 2-16 | 705 | 19 | 1.25 | −11 | +5 |
| Ex. 137 | 11-11 | 2-5 | 699 | 24 | 1.28 | −19 | +3 |
| Ex. 138 | 11-11 | 2-6 | 706 | 25 | 1.27 | −15 | +1 |
| Ex. 139 | 11-11 | 2-16 | 695 | 25 | 1.29 | −13 | +2 |
| Ex. 140 | 11-11 | 2-16 | 699 | 20 | 1.25 | −9 | +5 |
| Ex. 141 | 13-2 | 2-5 | 703 | 21 | 1.27 | −13 | +4 |
| Ex. 142 | 13-2 | 2-6 | 706 | 23 | 1.23 | −14 | +3 |
| Ex. 143 | 13-2 | 2-16 | 710 | 23 | 1.24 | −10 | +2 |
| Ex. 144 | 13-2 | 2-16 | 697 | 19 | 1.28 | −9 | +3 |

Examples 145 to 151
(Single-layer type electrophotosensitive material for analogue light source)

According to the same manner as that described in Examples 133 to 144 except for using 5 parts by weight of the perylene pigment represented by the above formula (9-1) as the electric charge generating material, a single-layer type electrophotosensitive material for analogue light source was produced.

The amount of the 2,4,7-trinitrofluorenonimine derivative was 15 parts by weight only in Example 146, and it was 30 parts by weight in other Examples. In addition, the hole transferring materials and electron transferring materials used in the Examples are shown by the number of the above compounds in Table 20, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 20.

TABLE 20

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 145 | 11-8 | 2-5 | 697 | 83 | 1.33 | −20 | +9 |
| Ex. 146 | 11-8 | 2-5 | 701 | 85 | 1.35 | −28 | +16 |
| Ex. 147 | 11-8 | 2-6 | 708 | 79 | 1.32 | −18 | +13 |
| Ex. 148 | 11-11 | 2-5 | 702 | 77 | 1.30 | −13 | +11 |
| Ex. 149 | 11-11 | 2-16 | 701 | 81 | 1.34 | −14 | +10 |
| Ex. 150 | 13-2 | 2-5 | 699 | 80 | 1.33 | −12 | +8 |
| Ex. 151 | 13-2 | 2-6 | 704 | 78 | 1.32 | −16 | +5 |

Examples 152 to 158
(Single-layer type electrophotosensitive material for analogue light source)

According to the same manner as that described in Examples 133 to 144 except for using 5 parts by weight of the bisazo pigment represented by the above formula (10-1) as the electric charge generating material, a single-layer type electrophotosensitive material for analogue light source was produced.

The amount of the 2,4,7-trinitrofluorenonimine 5 derivative was 15 parts by weight only in Example 155, and it was 30 parts by weight in other Examples. In addition, the hole transferring materials and electron transferring materials used in the Examples are shown by the number of the above compounds in Table 21, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 21.

TABLE 21

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 152 | 11-8 | 2-5 | 702 | 65 | 1.23 | −15 | +3 |
| Ex. 153 | 11-8 | 2-6 | 706 | 63 | 1.21 | −18 | +7 |
| Ex. 154 | 11-11 | 2-5 | 697 | 62 | 1.21 | −10 | +8 |
| Ex. 155 | 11-11 | 2-5 | 703 | 64 | 1.23 | −18 | +11 |
| Ex. 156 | 11-11 | 2-16 | 706 | 60 | 1.20 | −12 | +10 |
| Ex. 157 | 13-2 | 2-5 | 700 | 59 | 1.19 | −12 | +11 |
| Ex. 158 | 13-2 | 2-6 | 695 | 60 | 1.21 | −19 | +9 |

Examples 159 to 165
(Single-layer type electrophotosensitive material for analogue light source)

According to the same manner as that described in Examples 133 to 144 except for using 5 parts by weight of the bisazo pigment represented by the above formula (10-2) as the electric charge generating material, a single-layer type electrophotosensitive material for analogue light source was produced.

The amount of the 2,4,7-trinitrofluorenonimine derivative was 15 parts by weight only in Example 161, and it was 30 parts by weight in other Examples. In addition, the hole transferring materials and electron transferring materials used in the Examples are shown by the number of the above compounds in Table 22, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 22.

TABLE 22

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 159 | 11-8 | 2-5 | 702 | 50 | 1.14 | −12 | +7 |
| Ex. 160 | 11-8 | 2-6 | 705 | 49 | 1.13 | −16 | +8 |
| Ex. 161 | 11-11 | 2-5 | 699 | 52 | 1.21 | −18 | +9 |
| Ex. 162 | 11-11 | 2-5 | 699 | 48 | 1.13 | −15 | +5 |
| Ex. 163 | 11-11 | 2-16 | 694 | 45 | 1.12 | −13 | +5 |
| Ex. 164 | 13-2 | 2-5 | 689 | 43 | 1.13 | −15 | +3 |
| Ex. 165 | 13-2 | 2-6 | 697 | 50 | 1.15 | −14 | +6 |

Examples 166 to 172
(Single-layer type electrophotosensitive material for analogue light source)

According to the same manner as that described in Examples 133 to 144 except for using 5 parts by weight of the bisazo pigment represented by the above formula (10-3) as the electric charge generating material, a single-layer type electrophotosensitive material for analogue light source was produced.

The amount of the 2,4,7-trinitrofluorenonimine derivative was 15 parts by weight only in Example 168, and it was 30 parts by weight in other Examples. In addition, the hole transferring materials and electron transferring materials used in the Examples are shown by the number of the above compounds in Table 23, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 23.

TABLE 23

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 166 | 11-8 | 2-5 | 703 | 41 | 1.11 | −19 | +5 |
| Ex. 167 | 11-8 | 2-6 | 704 | 42 | 1.12 | −12 | +8 |
| Ex. 168 | 11-11 | 2-5 | 699 | 45 | 1.14 | −14 | +6 |
| Ex. 169 | 11-11 | 2-5 | 700 | 39 | 1.09 | −13 | +4 |
| Ex. 170 | 11-11 | 2-16 | 703 | 41 | 1.13 | −15 | +6 |
| Ex. 171 | 13-2 | 2-5 | 700 | 37 | 1.09 | −14 | +10 |
| Ex. 172 | 13-2 | 2-6 | 699 | 36 | 1.07 | −12 | +9 |

Examples 173 to 179
(Single-layer type electrophotosensitive material for analogue light source)

According to the same manner as that described in Examples 133 to 144 except for using 5 parts by weight of the bisazo pigment represented by the above formula (10-4) as the electric charge generating material, a single-layer type electrophotosensitive material for analogue light source was produced.

The amount of the 2,4,7-trinitrofluorenonimine derivative was 15 parts by weight only in Example 175, and it was 30 parts by weight in other Examples. In addition, the hole transferring materials and electron transferring materials used in the Examples are shown by the number of the above compounds in Table 24, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 24.

TABLE 24

|  | HTM | ETM | Initial Characteristics | | | After Repeating | |
|---|---|---|---|---|---|---|---|
|  |  |  | $V_0$ | Vr | $E_{1/2}$ | $\Delta V_0$ | $\Delta Vr$ |
| Ex. 173 | 11-8 | 2-5 | 703 | 23 | 1.01 | −10 | +5 |
| Ex. 174 | 11-8 | 2-6 | 705 | 21 | 1.00 | −12 | +7 |
| Ex. 175 | 11-11 | 2-5 | 701 | 28 | 1.09 | −13 | +4 |
| Ex. 176 | 11-11 | 2-5 | 704 | 23 | 1.01 | −9 | +6 |
| Ex. 177 | 11-11 | 2-16 | 702 | 19 | 1.00 | −8 | +3 |
| Ex. 178 | 13-2 | 2-5 | 700 | 18 | 0.98 | −11 | +2 |
| Ex. 179 | 13-2 | 2-6 | 703 | 17 | 0.97 | −13 | +4 |

Examples 180 to 188
(Single-layer type electrophotosensitive material for digital light source)

According to the same manner as that described in Examples 133 to 144 except for using a diphenoquinone derivative as the electron transferring material, a single-layer type electrophotosensitive material for digital light source was produced.

The amount of the diphenoquinone derivative was 30 parts by weight in all Examples. In addition, the hole transferring materials and electron transferring materials used in the Examples are shown by the number of the above compounds in Table 25, according to the same manner as that described above.

The electrophotosensitive materials of the above respective Examples were subjected to the above initial electric characteristics test (I) and electric characteristics test (I) after repeated exposure, and their characteristics were evaluated. The results are shown in Table 25.

TABLE 25

|  | HTM | ETM | Initial Characteristics | | | After Repeating | |
|---|---|---|---|---|---|---|---|
|  |  |  | $V_0$ | $Vr$ | $E_{1/2}$ | $\Delta V_0$ | $\Delta Vr$ |
| Ex. 180 | 11-8 | 3-1 | 710 | 35 | 1.31 | −15 | +3 |
| Ex. 181 | 11-8 | 3-3 | 705 | 38 | 1.32 | −14 | +3 |
| Ex. 182 | 11-8 | 3-7 | 702 | 36 | 1.30 | −18 | +4 |
| Ex. 183 | 11-11 | 3-1 | 704 | 35 | 1.35 | −23 | +5 |
| Ex. 184 | 11-11 | 3-3 | 697 | 37 | 1.31 | −19 | +5 |
| Ex. 185 | 11-11 | 3-7 | 709 | 39 | 1.33 | −17 | +4 |
| Ex. 186 | 13-2 | 3-1 | 698 | 37 | 1.34 | −15 | +6 |
| Ex. 187 | 13-2 | 3-3 | 699 | 36 | 1.30 | −18 | +5 |
| Ex. 188 | 13-2 | 3-7 | 704 | 38 | 1.31 | −13 | +4 |

Examples 189 to 195
(Single-layer type electrophotosensitive material for analogue light source)

According to the same manner as that described in Examples 180 to 188 except for using 5 parts by weight of the perylene pigment represented by the above formula (9-1) as the electric charge generating material, a single-layer type electrophotosensitive material for analogue light source was produced.

The amount of the diphenoquinone derivative was 15 parts by weight only in Example 190, and it was 30 parts by weight in other Examples. In addition, the hole transferring materials and electron transferring materials used in the Examples are shown by the number of the above compounds in Table 26, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 26.

TABLE 26

|  | HTM | ETM | Initial Characteristics | | | After Repeating | |
|---|---|---|---|---|---|---|---|
|  |  |  | $V_0$ | $Vr$ | $E_{1/2}$ | $\Delta V_0$ | $\Delta Vr$ |
| Ex. 189 | 11-8 | 3-1 | 697 | 89 | 1.35 | −25 | +15 |
| Ex. 190 | 11-8 | 3-1 | 705 | 88 | 1.38 | −28 | +16 |
| Ex. 191 | 11-8 | 3-3 | 705 | 88 | 1.34 | −21 | +13 |
| Ex. 192 | 11-11 | 3-1 | 702 | 78 | 1.31 | −23 | +12 |
| Ex. 193 | 11-11 | 3-7 | 698 | 76 | 1.31 | −24 | +16 |
| Ex. 194 | 13-2 | 3-1 | 699 | 83 | 1.33 | −28 | +17 |
| Ex. 195 | 13-2 | 3-3 | 696 | 75 | 1.29 | −27 | +13 |

Examples 196 to 202
(Single-layer type electrophotosensitive material for analogue light source)

According to the same manner as that described in Examples 180 to 188 except for using 5 parts by weight of the bisazo pigment represented by the above formula (10-1) as the electric charge generating material, a single-layer type electrophotosensitive material for analogue light source was produced.

The amount of the diphenoquinone derivative was 15 parts by weight only in Example 197, and it was 30 parts by weight in other Examples. In addition, the hole transferring materials and electron transferring materials used in the Examples are shown by the number of the above compounds in Table 27, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 27.

TABLE 27

|  | HTM | ETM | Initial Characteristics | | | After Repeating | |
|---|---|---|---|---|---|---|---|
|  |  |  | $V_0$ | $Vr$ | $E_{1/2}$ | $\Delta V_0$ | $\Delta Vr$ |
| Ex. 196 | 11-8 | 3-1 | 705 | 70 | 1.25 | −21 | +12 |
| Ex. 197 | 11-8 | 3-1 | 706 | 72 | 1.26 | −20 | +10 |
| Ex. 198 | 11-8 | 3-3 | 697 | 69 | 1.23 | −23 | +11 |
| Ex. 199 | 11-11 | 3-1 | 703 | 65 | 1.21 | −28 | +10 |
| Ex. 200 | 11-11 | 3-7 | 701 | 68 | 1.22 | −26 | +15 |
| Ex. 201 | 13-2 | 3-1 | 697 | 63 | 1.21 | −25 | +13 |
| Ex. 202 | 13-2 | 3-3 | 704 | 65 | 1.22 | −23 | +14 |

Examples 203 to 209
(Single-layer type electrophotosensitive material for analogue light source)

According to the same manner as that described in Examples 180 to 188 except for using 5 parts by weight of the bisazo pigment represented by the above formula (10-2) as the electric charge generating material, a single-layer type electrophotosensitive material for analogue light source was produced.

The amount of the diphenoquinone derivative was 15 parts by weight only in Example 204, and it was 30 parts by weight in other Examples. In addition, the hole transferring materials and electron transferring materials used in the Examples are shown by the number of the above compounds in Table 28, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 28.

TABLE 28

|  | HTM | ETM | Initial Characteristics | | | After Repeating | |
|---|---|---|---|---|---|---|---|
|  |  |  | $V_0$ | $Vr$ | $E_{1/2}$ | $\Delta V_0$ | $\Delta Vr$ |
| Ex. 203 | 11-8 | 3-1 | 703 | 59 | 1.19 | −32 | +14 |
| Ex. 204 | 11-8 | 3-1 | 698 | 63 | 1.23 | −35 | +16 |
| Ex. 205 | 11-8 | 3-3 | 702 | 62 | 1.21 | −31 | +13 |
| Ex. 206 | 11-11 | 3-1 | 699 | 55 | 1.18 | −29 | +15 |
| Ex. 207 | 11-11 | 3-7 | 701 | 51 | 1.16 | −30 | +12 |
| Ex. 208 | 13-2 | 3-1 | 700 | 63 | 1.23 | −26 | +13 |
| Ex. 209 | 13-2 | 3-3 | 705 | 61 | 1.21 | −23 | +13 |

Examples 210 to 216
(Single-layer type electrophotosensitive material for analogue light source)

According to the same manner as that described in Examples 180 to 188 except for using 5 parts by weight of the bisazo pigment represented by the above formula (10-3) as the electric charge generating material, a single-layer type electrophotosensitive material for analogue light source was produced.

The amount of the diphenoquinone derivative was 15 parts by weight only in Example 211, and it was 30 parts by weight in other Examples. In addition, the hole transferring materials and electron transferring materials used in the Examples are shown by the number of the above compounds in Table 29, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 29.

TABLE 29

| | HTM | ETM | Initial Characteristics | | | After Repeating | |
| --- | --- | --- | --- | --- | --- | --- | --- |
| | | | $V_0$ | Vr | $E_{1/2}$ | $\Delta V_0$ | $\Delta Vr$ |
| Ex. 210 | 11-8 | 3-1 | 706 | 55 | 1.18 | −30 | +15 |
| Ex. 211 | 11-8 | 3-1 | 701 | 59 | 1.20 | −34 | +14 |
| Ex. 212 | 11-8 | 3-3 | 708 | 53 | 1.17 | −29 | +13 |
| Ex. 213 | 11-11 | 3-1 | 706 | 58 | 1.19 | −27 | +12 |
| Ex. 214 | 11-11 | 3-7 | 701 | 52 | 1.17 | −28 | +11 |
| Ex. 215 | 13-2 | 3-1 | 699 | 50 | 1.14 | −23 | +13 |
| Ex. 216 | 13-2 | 3-3 | 696 | 51 | 1.16 | −28 | +16 |

Examples 217 to 223
(Single-layer type electrophotosensitive material for analogue light source)

According to the same manner as that described in Examples 180 to 188 except for using 5 parts by weight of the bisazo pigment represented by the above formula (10-4) as the electric charge generating material, a single-layer type electrophotosensitive material for analogue light source was produced.

The amount of the diphenoquinone derivative was 15 parts by weight only in Example 218, and it was 30 parts by weight in other Examples. In addition, the hole transferring materials and electron transferring materials used in the Examples are shown by the number of the above compounds in Table 30, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 30.

TABLE 30

| | HTM | ETM | Initial Characteristics | | | After Repeating | |
| --- | --- | --- | --- | --- | --- | --- | --- |
| | | | $V_0$ | Vr | $E_{1/2}$ | $\Delta V_0$ | $\Delta Vr$ |
| Ex. 217 | 11-8 | 3-1 | 703 | 30 | 1.05 | −25 | +12 |
| Ex. 218 | 11-8 | 3-1 | 701 | 33 | 1.07 | −26 | +14 |
| Ex. 219 | 11-8 | 3-3 | 697 | 28 | 1.04 | −28 | +14 |
| Ex. 220 | 11-11 | 3-1 | 700 | 26 | 1.02 | −27 | +13 |
| Ex. 221 | 11-11 | 3-7 | 705 | 32 | 1.06 | −28 | +17 |
| Ex. 222 | 13-2 | 3-1 | 701 | 30 | 1.03 | −29 | +11 |
| Ex. 223 | 13-2 | 3-3 | 709 | 29 | 1.03 | −21 | +14 |

Examples 224 to 233
(Single-layer type electrophotosensitive material for analogue light source)

According to the same manner as that described in Examples 145 to 151 except for using an ethylated nitrofluorenonimine derivative as the electron transferring material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 31, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 31.

TABLE 31

| Example No. | HTM | ETM | Initial Characteristics | | | After Repeating | |
| --- | --- | --- | --- | --- | --- | --- | --- |
| | | | $V_0$ | Vr | $E_{1/2}$ | $\Delta V_0$ | $\Delta Vr$ |
| 224 | 11-2 | 4-1 | 699 | 86 | 1.44 | −20 | +10 |
| 225 | 11-2 | 4-2 | 703 | 85 | 1.44 | −15 | +5 |
| 226 | 11-2 | 4-3 | 704 | 90 | 1.53 | −22 | +13 |
| 227 | 11-2 | 4-4 | 707 | 95 | 1.55 | −22 | +15 |
| 228 | 11-11 | 4-1 | 695 | 88 | 1.49 | −25 | +13 |
| 229 | 11-11 | 4-2 | 700 | 87 | 1.49 | −20 | +10 |
| 230 | 11-11 | 4-3 | 700 | 93 | 1.54 | −22 | +15 |
| 231 | 13-2 | 4-1 | 702 | 88 | 1.48 | −21 | +14 |
| 232 | 13-2 | 4-2 | 701 | 88 | 1.48 | −18 | +11 |
| 233 | 13-2 | 4-3 | 701 | 92 | 1.53 | −17 | +14 |

Examples 234 to 243
(Single-layer type electrophotosensitive material for analogue light source)

According to the same manner as that described in Examples 224 to 233 except for using 5 parts by weight of the bisazo pigment represented by the above formula (10-1) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 32, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 32.

TABLE 32

| Example No. | HTM | ETM | Initial Characteristics | | | After Repeating | |
| --- | --- | --- | --- | --- | --- | --- | --- |
| | | | $V_0$ | Vr | $E_{1/2}$ | $\Delta V_0$ | $\Delta Vr$ |
| 234 | 11-2 | 4-1 | 704 | 66 | 1.30 | −18 | +14 |
| 235 | 11-2 | 4-2 | 700 | 65 | 1.29 | −13 | +6 |
| 236 | 11-2 | 4-3 | 700 | 70 | 1.35 | −15 | +12 |
| 237 | 11-2 | 4-4 | 703 | 74 | 1.38 | −20 | +10 |
| 238 | 11-11 | 4-1 | 710 | 67 | 1.34 | −15 | +11 |
| 239 | 11-11 | 4-2 | 691 | 65 | 1.30 | −10 | +3 |
| 240 | 11-11 | 4-3 | 697 | 73 | 1.37 | −20 | +15 |
| 241 | 13-2 | 4-1 | 699 | 70 | 1.35 | −16 | +12 |

TABLE 32-continued

| Example No. | HTM | ETM | Initial Characteristics $V_0$ | $V_r$ | $E_{1/2}$ | After Repeating $\Delta V_0$ | $\Delta V_r$ |
|---|---|---|---|---|---|---|---|
| 242 | 13-2 | 4-2 | 702 | 66 | 1.30 | −11 | +9 |
| 243 | 13-2 | 4-3 | 703 | 72 | 1.35 | −19 | +10 |

Examples 244 to 253
(Single-layer type electrophotosensitive material for analogue light source)

According to the same manner as that described in Examples 224 to 233 except for using 5 parts by weight of the bisazo pigment represented by the above formula (10-2) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 33, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 33.

TABLE 33

| Example No. | HTM | ETM | Initial Characteristics $V_0$ | $V_r$ | $E_{1/2}$ | After Repeating $\Delta V_0$ | $\Delta V_r$ |
|---|---|---|---|---|---|---|---|
| 244 | 11-2 | 4-1 | 695 | 50 | 1.18 | −16 | +9 |
| 245 | 11-2 | 4-2 | 700 | 51 | 1.19 | −10 | +7 |
| 246 | 11-2 | 4-3 | 703 | 55 | 1.22 | −18 | +9 |
| 247 | 11-2 | 4-4 | 705 | 60 | 1.23 | −20 | +10 |
| 248 | 11-11 | 4-1 | 701 | 48 | 1.15 | −17 | +10 |
| 249 | 11-11 | 4-2 | 702 | 49 | 1.15 | −15 | +9 |
| 250 | 11-11 | 4-3 | 699 | 56 | 1.23 | −20 | +9 |
| 251 | 13-2 | 4-1 | 712 | 42 | 1.13 | −15 | +13 |
| 252 | 13-2 | 4-2 | 705 | 45 | 1.13 | −17 | +11 |
| 253 | 13-2 | 4-3 | 704 | 53 | 1.20 | −19 | +14 |

Examples 254 to 263
(Single-layer type electrophotosensitive material for analogue light source)

According to the same manner as that described in Examples 224 to 233 except for using 5 parts by weight of the bisazo pigment represented by the above formula (10-3) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 34, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 34.

TABLE 34

| Example No. | HTM | ETM | Initial Characteristics $V_0$ | $V_r$ | $E_{1/2}$ | After Repeating $\Delta V_0$ | $\Delta V_r$ |
|---|---|---|---|---|---|---|---|
| 254 | 11-2 | 4-1 | 706 | 44 | 1.14 | −16 | +12 |
| 255 | 11-2 | 4-2 | 708 | 40 | 1.10 | −13 | +6 |
| 256 | 11-2 | 4-3 | 701 | 50 | 1.19 | −17 | +10 |
| 257 | 11-2 | 4-4 | 696 | 53 | 1.19 | −21 | +14 |
| 258 | 11-11 | 4-1 | 698 | 45 | 1.14 | −18 | +15 |
| 259 | 11-11 | 4-2 | 699 | 44 | 1.14 | −15 | +14 |
| 260 | 11-11 | 4-3 | 700 | 49 | 1.19 | −19 | +11 |
| 261 | 13-2 | 4-1 | 706 | 41 | 1.11 | −20 | +13 |
| 262 | 13-2 | 4-2 | 695 | 43 | 1.12 | −15 | +10 |
| 263 | 13-2 | 4-3 | 691 | 45 | 1.15 | −20 | +12 |

Examples 264 to 273
(Single-layer type electrophotosensitive material for analogue light source)

According to the same manner as that described in Examples 224 to 233 except for using 5 parts by weight of the bisazo pigment represented by the above formula (10-4) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 35, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 35.

TABLE 35

| Example No. | HTM | ETM | Initial Characteristics $V_0$ | $V_r$ | $E_{1/2}$ | After Repeating $\Delta V_0$ | $\Delta V_r$ |
|---|---|---|---|---|---|---|---|
| 264 | 11-2 | 4-1 | 710 | 37 | 1.09 | −21 | +13 |
| 265 | 11-2 | 4-2 | 708 | 33 | 1.08 | −15 | +9 |
| 266 | 11-2 | 4-3 | 691 | 40 | 1.10 | −16 | +11 |
| 267 | 11-2 | 4-4 | 693 | 45 | 1.13 | −25 | +14 |
| 268 | 11-11 | 4-1 | 709 | 40 | 1.10 | −20 | +10 |
| 269 | 11-11 | 4-2 | 705 | 36 | 1.08 | −18 | +11 |
| 270 | 11-11 | 4-3 | 700 | 42 | 1.10 | −19 | +13 |
| 271 | 13-2 | 4-1 | 703 | 43 | 1.12 | −17 | +15 |
| 272 | 13-2 | 4-2 | 702 | 35 | 1.08 | −15 | +8 |
| 273 | 13-2 | 4-3 | 702 | 40 | 1.10 | −23 | +13 |

Examples 274 to 280
(Single-layer type electrophotosensitive material for analogue light source)

According to the same manner as that described in Examples 145 to 151 except for using a tryptoanthrine derivative as the electron transferring material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 36, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 36.

TABLE 36

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 274 | 11-2 | 5-3 | 710 | 99 | 1.30 | −30 | +18 |
| 275 | 11-2 | 5-1 | 708 | 89 | 1.20 | −24 | +15 |
| 276 | 11-2 | 5-4 | 700 | 92 | 1.18 | −28 | +10 |
| 277 | 11-11 | 5-1 | 704 | 88 | 1.25 | −25 | +13 |
| 278 | 11-11 | 5-4 | 702 | 85 | 1.27 | −25 | +13 |
| 279 | 13-2 | 5-1 | 700 | 83 | 1.15 | −23 | +12 |
| 280 | 13-2 | 5-4 | 705 | 83 | 1.15 | −28 | +15 |

Examples 281 to 287
(Single-layer type electrophotosensitive material for analogue light source)

According to the same manner as that described in Examples 274 to 280 except for using 5 parts by weight of the bisazo pigment represented by the above formula (10-1) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 37, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 37.

TABLE 37

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 281 | 11-2 | 5-3 | 702 | 81 | 1.11 | −30 | +17 |
| 282 | 11-2 | 5-1 | 695 | 75 | 1.03 | −20 | +15 |
| 283 | 11-2 | 5-4 | 698 | 78 | 1.05 | −23 | +15 |
| 284 | 11-11 | 5-1 | 702 | 74 | 1.04 | −25 | +15 |
| 285 | 11-11 | 5-4 | 704 | 72 | 1.01 | −24 | +14 |
| 286 | 13-2 | 5-1 | 703 | 70 | 0.99 | −28 | +13 |
| 287 | 13-2 | 5-4 | 705 | 70 | 0.99 | −28 | +13 |

Examples 288 to 294
(Single-layer type electrophotosensitive material for analogue light source)

According to the same manner as that described in Examples 274 to 280 except for using 5 parts by weight of the bisazo pigment represented by the above formula (10-2) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 38, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 38.

TABLE 38

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 288 | 11-2 | 5-3 | 706 | 70 | 1.03 | −30 | +18 |
| 289 | 11-2 | 5-1 | 701 | 66 | 1.03 | −25 | +12 |
| 290 | 11-2 | 5-4 | 699 | 62 | 1.01 | −25 | +12 |
| 291 | 11-11 | 5-1 | 700 | 60 | 0.98 | −30 | +15 |
| 292 | 11-11 | 5-4 | 704 | 60 | 0.98 | −30 | +15 |
| 293 | 13-2 | 5-1 | 705 | 63 | 1.00 | −27 | +13 |
| 294 | 13-2 | 5-4 | 701 | 63 | 1.00 | −27 | +12 |

Examples 295 to 301
(Single-layer type electrophotosensitive material for analogue light source)

According to the same manner as that described in Examples 274 to 280 except for using 5 parts by weight of the bisazo pigment represented by the above formula (10-3) as the electric charge generating material, a single-layer type electrophotosensitive material for analogue light source was produced The amount of the tryptoanthrine derivative was 30 parts by weight in all Examples. In addition, the hole transferring materials and electron transferring materials used in the Examples are shown by the number of the above compounds in Table 39, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 39.

TABLE 39

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 295 | 11-2 | 5-3 | 702 | 71 | 1.06 | −35 | +19 |
| 296 | 11-2 | 5-1 | 704 | 65 | 1.03 | −25 | +15 |
| 297 | 11-2 | 5-4 | 704 | 60 | 0.97 | −35 | +17 |
| 298 | 11-11 | 5-1 | 705 | 64 | 1.03 | −27 | +13 |
| 299 | 11-11 | 5-4 | 700 | 65 | 1.03 | −24 | +12 |
| 300 | 13-2 | 5-1 | 702 | 66 | 1.05 | −23 | +15 |
| 301 | 13-2 | 5-4 | 701 | 66 | 1.05 | −25 | +13 |

Examples 302 to 308
(Single-layer type electrophotosensitive material for analogue light source)

According to the same manner as that described in Examples 274 to 280 except for using 5 parts by weight of the bisazo pigment represented by the above formula (10-4) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 40, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 40.

TABLE 40

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 302 | 11-2 | 5-3 | 700 | 68 | 1.04 | −35 | +20 |
| 303 | 11-2 | 5-1 | 704 | 55 | 0.98 | −25 | +13 |
| 304 | 11-2 | 5-4 | 697 | 61 | 1.00 | −20 | +15 |
| 305 | 11-11 | 5-1 | 695 | 57 | 0.99 | −25 | +12 |
| 306 | 11-11 | 5-4 | 700 | 59 | 1.00 | −23 | +13 |
| 307 | 13-2 | 5-1 | 705 | 55 | 0.99 | −23 | +15 |
| 308 | 13-2 | 5-4 | 705 | 57 | 0.99 | −20 | +10 |

Examples 309 to 317
(Single-layer type electrophotosensitive material for analogue light source)

According to the same manner as that described in Examples 145 to 151 except for using a tryptoanthrinimine derivative as the electron transferring material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 41, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 41.

TABLE 41

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 309 | 11-2 | 6-3 | 705 | 80 | 1.40 | −21 | +12 |
| 310 | 11-2 | 6-6 | 704 | 90 | 1.54 | −25 | +15 |
| 311 | 11-2 | 6-10 | 701 | 85 | 1.43 | −23 | +13 |
| 312 | 11-11 | 6-3 | 701 | 83 | 1.42 | −25 | +14 |
| 313 | 11-11 | 6-6 | 700 | 89 | 1.53 | −25 | +10 |
| 314 | 11-11 | 6-10 | 695 | 86 | 1.45 | −20 | +10 |
| 315 | 13-2 | 6-3 | 704 | 84 | 1.44 | −20 | +12 |
| 316 | 13-2 | 6-6 | 703 | 83 | 1.43 | −18 | +12 |
| 317 | 13-2 | 6-10 | 704 | 86 | 1.44 | −23 | +13 |

Examples 318 to 326
(Single-layer type electrophotosensitive material for analogue light source)

According to the same manner as that described in Examples 309 to 317 except for using 5 parts by weight of the bisazo pigment represented by the above formula (10-1) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 42, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 42.

TABLE 42

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 318 | 11-2 | 6-3 | 706 | 60 | 1.25 | −20 | +10 |
| 319 | 11-2 | 6-6 | 703 | 69 | 1.35 | −15 | +12 |
| 320 | 11-2 | 6-10 | 700 | 64 | 1.30 | −18 | +9 |
| 321 | 11-11 | 6-3 | 697 | 65 | 1.30 | −18 | +10 |
| 322 | 11-11 | 6-6 | 701 | 72 | 1.37 | −17 | +10 |
| 323 | 11-11 | 6-10 | 701 | 70 | 1.36 | −15 | +12 |
| 324 | 13-2 | 6-3 | 695 | 66 | 1.29 | −12 | +11 |
| 325 | 13-2 | 6-6 | 702 | 71 | 1.35 | −16 | +11 |
| 326 | 13-2 | 6-10 | 700 | 69 | 1.30 | −16 | +13 |

Examples 327 to 335
(Single-layer type electrophotosensitive material for analogue light source)

According to the same manner as that described in Examples 309 to 317 except for using 5 parts by weight of the bisazo pigment represented by the above formula (10-2) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 43, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 43.

TABLE 43

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 327 | 11-2 | 6-3 | 705 | 50 | 1.18 | −10 | +10 |
| 328 | 11-2 | 6-6 | 700 | 55 | 1.25 | −15 | +9 |
| 329 | 11-2 | 6-10 | 702 | 52 | 1.21 | −14 | +8 |
| 330 | 11-11 | 6-3 | 703 | 52 | 1.20 | −16 | +12 |
| 331 | 11-11 | 6-6 | 704 | 60 | 1.30 | −15 | +13 |
| 332 | 11-11 | 6-10 | 700 | 56 | 1.25 | −13 | +14 |
| 333 | 13-2 | 6-3 | 700 | 55 | 1.24 | −13 | +13 |
| 334 | 13-2 | 6-6 | 695 | 57 | 1.25 | −14 | +10 |
| 335 | 13-2 | 6-10 | 697 | 55 | 1.24 | −13 | +11 |

Examples 336 to 344
(Single-layer type electrophotosensitive material for analogue light source)

According to the same manner as that described in Examples 309 to 317 except for using 5 parts by weight of the bisazo pigment represented by the above formula (10-3) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 44, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 44.

TABLE 44

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 336 | 11-2 | 6-3 | 702 | 39 | 1.10 | −20 | +13 |
| 337 | 11-2 | 6-6 | 702 | 48 | 1.15 | −14 | +9 |
| 338 | 11-2 | 6-10 | 704 | 45 | 1.14 | −16 | +10 |
| 339 | 11-11 | 6-3 | 699 | 41 | 1.11 | −17 | +11 |
| 340 | 11-11 | 6-6 | 700 | 50 | 1.18 | −13 | +10 |
| 341 | 11-11 | 6-10 | 694 | 47 | 1.15 | −15 | +12 |
| 342 | 13-2 | 6-3 | 705 | 44 | 1.13 | −11 | +11 |
| 343 | 13-2 | 6-6 | 705 | 51 | 1.18 | −16 | +13 |
| 344 | 13-2 | 6-10 | 689 | 47 | 1.16 | −12 | +13 |

Examples 345 to 353
(Single-layer type electrophotosensitive material for analogue light source)

According to the same manner as that described in Examples 309 to 317 except for using 5 parts by weight of the bisazo pigment represented by the above formula (10-4) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 45, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 45.

TABLE 45

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 345 | 11-2 | 6-3 | 702 | 40 | 1.11 | −15 | +10 |
| 346 | 11-2 | 6-6 | 700 | 49 | 1.19 | −18 | +12 |
| 347 | 11-2 | 6-10 | 703 | 44 | 1.15 | −17 | +13 |
| 348 | 11-11 | 6-3 | 703 | 42 | 1.11 | −20 | +14 |
| 349 | 11-11 | 6-6 | 704 | 50 | 1.20 | −16 | +11 |
| 350 | 11-11 | 6-10 | 705 | 50 | 1.20 | −15 | +11 |
| 351 | 13-2 | 6-3 | 697 | 44 | 1.13 | −13 | +13 |
| 352 | 13-2 | 6-6 | 698 | 52 | 1.20 | −12 | +13 |
| 353 | 13-2 | 6-10 | 699 | 51 | 1.20 | −15 | +15 |

Examples 354 to 359
(Single-layer type electrophotosensitive material for digital light source)

According to the same manner as that described in Examples 9 to 15 except for using 50 parts by weight of the naphthylenediamine in combination with 50 parts by weight of the phenylenediamine derivative as the electric charge transferring material, a single-layer type electrophotosensitive material for digital light source was produced.

In addition, the electric charge transferring materials used in the Examples are shown by the number of the above compounds in Table 46, according to the same manner as that described above.

The electrophotosensitive materials of the above respective Examples were subjected to the above initial electric characteristics test (I) and electric characteristics test (I) after repeated exposure, and their characteristics were evaluated. The results are shown in Table 46.

TABLE 46

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 354 | 11-2 | 71-1 | 701 | 35 | 1.32 | −15 | +7 |
| 355 | 11-2 | 71-2 | 708 | 29 | 1.27 | −16 | +8 |
| 356 | 11-2 | 71-3 | 693 | 38 | 1.34 | −13 | +5 |
| 357 | 11-11 | 71-1 | 712 | 36 | 1.32 | −15 | +5 |
| 358 | 13-2 | 71-1 | 709 | 31 | 1.28 | −16 | +8 |
| 359 | 11-2 | 72-1 | 709 | 34 | 1.31 | −14 | +6 |

Examples 360 to 365
(Single-layer type electrophotosensitive material for analogue light source)

According to the same manner as that described in Examples 354 to 359 except for using 5 parts by weight of the perylene pigment represented by the above formula (9-1) as the electric charge generating material, a single-layer type electrophotosensitive material for analogue light source was produced.

In addition, the electric charge transferring materials used in the Examples are shown by the number of the above compounds in Table 47, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 47.

TABLE 47

| Example No. | CTM | | Initial Characteristics | | | After Repeating | |
|---|---|---|---|---|---|---|---|
| | | | $V_0$ | Vr | $E_{1/2}$ | $\Delta V_0$ | $\Delta Vr$ |
| 360 | 11-2 | 71-1 | 703 | 113 | 1.69 | −20 | +12 |
| 361 | 11-2 | 71-2 | 714 | 110 | 1.68 | −17 | +15 |
| 362 | 11-2 | 71-3 | 691 | 118 | 1.71 | −19 | +10 |
| 363 | 11-11 | 71-1 | 698 | 119 | 1.71 | −15 | +10 |
| 364 | 13-2 | 71-1 | 700 | 115 | 1.70 | −18 | +14 |
| 365 | 11-2 | 72-1 | 697 | 112 | 1.70 | −18 | +13 |

Examples 366 to 371
(Single-layer type electrophotosensitive material for analogue light source)

According to the same manner as that described in Examples 354 to 359 except for using 5 parts by weight of the bisazo pigment represented by the above formula (10-1) as the electric charge generating material, a single-layer type electrophotosensitive material for analogue light source was produced.

In addition, the electric charge transferring materials used in the Examples are shown by the number of the above compounds in Table 48, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 48.

TABLE 48

| Example No. | CTM | Initial Characteristics | | | After Repeating | |
|---|---|---|---|---|---|---|
| | | $V_0$ | Vr | $E_{1/2}$ | $\Delta V_0$ | $\Delta Vr$ |
| 366 | 11-2 | 71-1 | 715 | 44 | 1.25 | −20 | +8 |
| 367 | 11-2 | 71-2 | 709 | 48 | 1.28 | −17 | +7 |
| 368 | 11-2 | 71-3 | 702 | 41 | 1.24 | −20 | +10 |
| 369 | 11-11 | 71-1 | 716 | 39 | 1.24 | −15 | +5 |
| 370 | 13-2 | 71-1 | 697 | 47 | 1.27 | −19 | +7 |
| 371 | 11-2 | 72-1 | 718 | 42 | 1.25 | −15 | +8 |

Examples 372 to 377

(Single-layer type electrophotosensitive material for analogue light source)

According to the same manner as that described in Examples 354 to 359 except for using 5 parts by weight of the bisazo pigment represented by the above formula (10-2) as the electric charge generating material, a single-layer type electrophotosensitive material for analogue light source was produced.

In addition, the electric charge transferring materials used in the Examples are shown by the number of the above compounds in Table 49, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 49.

TABLE 49

| Example No. | CTM | Initial Characteristics | | | After Repeating | |
|---|---|---|---|---|---|---|
| | | $V_0$ | Vr | $E_{1/2}$ | $\Delta V_0$ | $\Delta Vr$ |
| 372 | 11-2 | 71-1 | 714 | 39 | 1.31 | −18 | +10 |
| 373 | 11-2 | 71-2 | 691 | 35 | 1.28 | −15 | +8 |
| 374 | 11-2 | 71-3 | 700 | 33 | 1.25 | −20 | +12 |
| 375 | 11-11 | 71-1 | 698 | 33 | 1.23 | −17 | +11 |
| 376 | 13-2 | 71-1 | 703 | 35 | 1.26 | −13 | +11 |
| 377 | 11-2 | 72-1 | 700 | 34 | 1.26 | −17 | +11 |

Examples 378 to 383

(Single-layer type electrophotosensitive material for analogue light source)

According to the same manner as that described in Examples 354 to 359 except for using 5 parts by weight of the bisazo pigment represented by the above formula (10-3) as the electric charge generating material, a single-layer type electrophotosensitive material for analogue light source was produced.

In addition, the electric charge transferring materials used in the Examples are shown by the number of the above compounds in Table 50, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 50.

TABLE 50

| Example No. | CTM | Initial Characteristics | | | After Repeating | |
|---|---|---|---|---|---|---|
| | | $V_0$ | Vr | $E_{1/2}$ | $\Delta V_0$ | $\Delta Vr$ |
| 378 | 11-2 | 71-1 | 711 | 42 | 1.33 | −21 | +17 |
| 379 | 11-2 | 71-2 | 693 | 37 | 1.30 | −18 | +18 |
| 380 | 11-2 | 71-3 | 698 | 33 | 1.28 | −15 | +15 |
| 381 | 11-11 | 71-1 | 709 | 39 | 1.31 | −18 | +20 |
| 382 | 13-2 | 71-1 | 700 | 34 | 1.31 | −15 | +21 |
| 383 | 11-2 | 72-1 | 705 | 35 | 1.29 | −18 | +16 |

Examples 384 to 389

(Single-layer type electrophotosensitive material for analogue light source)

According to the same manner as that described in Examples 354 to 359 except for using 5 parts by weight of the bisazo pigment represented by the above formula (10-4) as the electric charge generating material, a single-layer type electrophotosensitive material for analogue light source was produced.

In addition, the electric charge transferring materials used in the Examples are shown by the number of the above compounds in Table 51, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 51.

TABLE 51

| Example No. | CTM | Initial Characteristics | | | After Repeating | |
|---|---|---|---|---|---|---|
| | | $V_0$ | Vr | $E_{1/2}$ | $\Delta V_0$ | $\Delta Vr$ |
| 384 | 11-2 | 71-1 | 710 | 28 | 1.13 | −22 | +12 |
| 385 | 11-2 | 71-2 | 699 | 24 | 1.10 | −21 | +14 |
| 386 | 11-2 | 71-3 | 708 | 25 | 1.11 | −17 | +12 |
| 387 | 11-11 | 71-1 | 703 | 27 | 1.13 | −15 | +11 |
| 388 | 13-2 | 71-1 | 691 | 23 | 1.10 | −15 | +15 |
| 389 | 11-2 | 72-1 | 699 | 25 | 1.10 | −20 | +12 |

Examples 390 to 395

(Single-layer type electrophotosensitive material for analogue light source)

According to the same manner as that described in Examples 354 to 359 except for using 5 parts by weight of the bisazo pigment represented by the above formula (10-5) as the electric charge generating material, a single-layer type electrophotosensitive material for analogue light source was produced.

In addition, the electric charge transferring materials used in the Examples are shown by the number of the above compounds in Table 52, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 52.

TABLE 52

| Example No. | CTM | | $V_0$ | Vr | $E_{1/2}$ | $\Delta V_0$ | $\Delta Vr$ |
|---|---|---|---|---|---|---|---|
| 390 | 11-2 | 71-1 | 699 | 48 | 1.29 | −19 | +10 |
| 391 | 11-2 | 71-2 | 712 | 45 | 1.25 | −24 | +13 |
| 392 | 11-2 | 71-3 | 705 | 46 | 1.26 | −18 | +17 |
| 393 | 11-11 | 71-1 | 707 | 43 | 1.24 | −20 | +9 |
| 394 | 13-2 | 71-1 | 713 | 45 | 1.25 | −15 | +12 |
| 395 | 11-2 | 72-1 | 712 | 44 | 1.25 | −19 | +8 |

Examples 396 to 401

(Single-layer type electrophotosensitive material for analogue light source)

According to the same manner as that described in Examples 354 to 359 except for using 5 parts by weight of the bisazo pigment represented by the above formula (10-6) as the electric charge generating material, a single-layer type electrophotosensitive material for analogue light source was produced.

In addition, the electric charge transferring materials used in the Examples are shown by the number of the above compounds in Table 53, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 53.

TABLE 53

| Example No. | CTM | | $V_0$ | Vr | $E_{1/2}$ | $\Delta V_0$ | $\Delta Vr$ |
|---|---|---|---|---|---|---|---|
| 396 | 11-2 | 71-1 | 710 | 47 | 1.20 | −18 | ±0 |
| 397 | 11-2 | 71-2 | 695 | 42 | 1.15 | −15 | +2 |
| 398 | 11-2 | 71-3 | 700 | 41 | 1.17 | −15 | +10 |
| 399 | 11-11 | 71-1 | 713 | 45 | 1.15 | −19 | +5 |
| 400 | 13-2 | 71-1 | 698 | 42 | 1.15 | −17 | +3 |
| 401 | 11-2 | 72-1 | 704 | 44 | 1.16 | −16 | ±0 |

Examples 402 to 407

(Single-layer type electrophotosensitive material for analogue light source)

According to the same manner as that described in Examples 354 to 359 except for using 5 parts by weight of the bisazo pigment represented by the above formula (10-7) as the electric charge generating material, a single-layer type electrophotosensitive material for analogue light source was produced.

In addition, the electric charge transferring materials used in the Examples are shown by the number of the above compounds in Table 54, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 54.

TABLE 54

| Example No. | CTM | | $V_0$ | Vr | $E_{1/2}$ | $\Delta V_0$ | $\Delta Vr$ |
|---|---|---|---|---|---|---|---|
| 402 | 11-2 | 71-1 | 704 | 42 | 1.25 | −16 | +1 |
| 403 | 11-2 | 71-2 | 706 | 42 | 1.28 | −12 | ±0 |
| 404 | 11-2 | 71-3 | 708 | 48 | 1.28 | −16 | +2 |
| 405 | 11-11 | 71-1 | 695 | 45 | 1.27 | −15 | ±0 |
| 406 | 13-2 | 71-1 | 697 | 46 | 1.25 | −12 | +5 |
| 407 | 11-2 | 72-1 | 711 | 45 | 1.26 | −13 | +2 |

Examples 408 to 413

(Multi-layer type electrophotosensitive material for digital light source)

According to the same manner as that described in Examples 71 to 77 except for using 0.5 parts by weight of the naphthylenediamine derivative in combination with 0.5 parts by weight of the phenylenediamine derivative as the electric charge transferring material, a multi-layer type electrophotosensitive material for digital light source was produced.

In addition, the electric charge transferring materials used in the Examples are shown by the number of the above compounds in Table 55, according to the same manner as that described above.

The electrophotosensitive materials of the above respective Examples were subjected to the above initial electric characteristics test (III) and electric characteristics test (III) after repeated exposure, and their characteristics were evaluated. The results are shown in Table 55.

TABLE 55

| Example No. | CTM | | $V_0$ | Vr | $E_{1/2}$ | $\Delta V_0$ | $\Delta Vr$ |
|---|---|---|---|---|---|---|---|
| 408 | 11-2 | 71-1 | −715 | −9 | 0.38 | −16 | +10 |
| 409 | 11-2 | 71-2 | −693 | −8 | 0.36 | −13 | +7 |
| 410 | 11-2 | 71-3 | −700 | −10 | 0.38 | −15 | +10 |
| 411 | 11-11 | 71-1 | −702 | −8 | 0.35 | −18 | +9 |
| 412 | 13-2 | 71-1 | −705 | −7 | 0.34 | −17 | +10 |
| 413 | 11-2 | 72-1 | −713 | −10 | 0.37 | −14 | +9 |

Examples 414 to 419

(Multi-layer type electrophotosensitive material for analogue light source)

According to the same manner as that described in Examples 408 to 413 except for using 2.5 parts by weight of the perylene pigment represented by the above formula (9-1) as the electric charge generating material, a multi-layer type electrophotosensitive material for analogue light source was produced.

In addition, the electric charge transferring materials used in the Examples are shown by the number of the above compounds in Table 56, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 56.

TABLE 56

| Example No. | CTM | | $V_0$ | Vr | $E_{1/2}$ | After Repeating $\Delta V_0$ | $\Delta Vr$ |
|---|---|---|---|---|---|---|---|
| 414 | 11-2 | 71-1 | −713 | −120 | 1.85 | −60 | +10 |
| 415 | 11-2 | 71-2 | −707 | −118 | 1.84 | −56 | +12 |
| 416 | 11-2 | 71-3 | −705 | −115 | 1.82 | −50 | +15 |
| 417 | 11-11 | 71-1 | −712 | −117 | 1.84 | −58 | +8 |
| 418 | 13-2 | 71-1 | −699 | −120 | 1.85 | −50 | +9 |
| 419 | 11-2 | 72-1 | −700 | −118 | 1.85 | −56 | +12 |

Examples 420 to 425

(Multi-layer type electrophotosensitive material for analogue light source)

According to the same manner as that described in Examples 408 to 413 except for using 2.5 parts by weight of the bisazo pigment represented by the above formula (10-1) as the electric charge generating material, a multi-layer type electrophotosensitive material for analogue light source was produced.

In addition, the electric charge transferring materials used in the Examples are shown by the number of the above compounds in Table 57, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 57.

TABLE 57

| Example No. | CTM | | $V_0$ | Vr | $E_{1/2}$ | After Repeating $\Delta V_0$ | $\Delta Vr$ |
|---|---|---|---|---|---|---|---|
| 420 | 11-2 | 71-1 | −698 | −20 | 0.36 | −30 | +10 |
| 421 | 11-2 | 71-2 | −713 | −18 | 0.34 | −25 | +5 |
| 422 | 11-2 | 71-3 | −700 | −19 | 0.34 | −27 | +7 |
| 423 | 11-11 | 71-1 | −695 | −20 | 0.35 | −30 | +10 |
| 424 | 13-2 | 71-1 | −710 | −20 | 0.36 | −28 | +8 |
| 425 | 11-2 | 72-1 | −713 | −17 | 0.34 | −28 | +9 |

Examples 426 to 431

(Multi-layer type electrophotosensitive material for analogue light source)

According to the same manner as that described in Examples 408 to 413 except for using 2.5 parts by weight of the bisazo pigment represented by the above formula (10-2) as the electric charge generating material, a multi-layer type electrophotosensitive material for analogue light source was produced.

In addition, the electric charge transferring materials used in the Examples are shown by the number of the above compounds in Table 58, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 58.

TABLE 58

| Example No. | CTM | | $V_0$ | Vr | $E_{1/2}$ | After Repeating $\Delta V_0$ | $\Delta Vr$ |
|---|---|---|---|---|---|---|---|
| 426 | 11-2 | 71-1 | −697 | −20 | 0.34 | −25 | +5 |
| 427 | 11-2 | 71-2 | −695 | −15 | 0.31 | −18 | +10 |
| 428 | 11-2 | 71-3 | −708 | −16 | 0.33 | −19 | +13 |
| 429 | 11-11 | 71-1 | −706 | −15 | 0.32 | −22 | +15 |
| 430 | 13-2 | 71-1 | −704 | −19 | 0.33 | −21 | +13 |
| 431 | 11-2 | 72-1 | −695 | −17 | 0.32 | −20 | +14 |

Examples 432 to 437

(Multi-layer type electrophotosensitive material for analogue light source)

According to the same manner as that described in Examples 408 to 413 except for using 2.5 parts by weight of the bisazo pigment represented by the above formula (10-3) as the electric charge generating material, a multi-layer type electrophotosensitive material for analogue light source was produced.

In addition, the electric charge transferring materials used in the Examples are shown by the number of the above compounds in Table 59, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 59.

TABLE 59

| Example No. | CTM | | $V_0$ | Vr | $E_{1/2}$ | After Repeating $\Delta V_0$ | $\Delta Vr$ |
|---|---|---|---|---|---|---|---|
| 432 | 11-2 | 71-1 | −700 | −19 | 0.40 | −45 | +15 |
| 433 | 11-2 | 71-2 | −698 | −15 | 0.41 | −41 | +20 |
| 434 | 11-2 | 71-3 | −691 | −17 | 0.38 | −46 | +18 |
| 435 | 11-11 | 71-1 | −714 | −19 | 0.38 | −38 | +18 |
| 436 | 13-2 | 71-1 | −703 | −15 | 0.40 | −40 | +20 |
| 437 | 11-2 | 72-1 | −705 | −16 | 0.40 | −43 | +20 |

Examples 438 to 443

(Multi-layer type electrophotosensitive material for analogue light source)

According to the same manner as that described in Examples 408 to 413 except for using 2.5 parts by weight of the bisazo pigment represented by the above formula (10-4) as the electric charge generating material, a multi-layer type electrophotosensitive material for analogue light source was produced.

In addition, the electric charge transferring materials used in the Examples are shown by the number of the above compounds in Table 60, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 60.

TABLE 60

| Example No. | CTM | | $V_0$ | Vr | $E_{1/2}$ | $\Delta V_0$ | $\Delta$Vr |
|---|---|---|---|---|---|---|---|
| 438 | 11-2 | 71-1 | −697 | −10 | 0.33 | −48 | +10 |
| 439 | 11-2 | 71-2 | −716 | −7 | 0.31 | −45 | +20 |
| 440 | 11-2 | 71-3 | −702 | −9 | 0.29 | −43 | +15 |
| 441 | 11-11 | 71-1 | −709 | −11 | 0.30 | −43 | +13 |
| 442 | 13-2 | 71-1 | −715 | −10 | 0.30 | −40 | +17 |
| 443 | 11-2 | 72-1 | −706 | −9 | 0.32 | −45 | +15 |

Examples 444 to 449
(Multi-layer type electrophotosensitive material for analogue light source)

According to the same manner as that described in Examples 408 to 413 except for using 2.5 parts by weight of the bisazo pigment represented by the above formula (10-5) as the electric charge generating material, a multi-layer type electrophotosensitive material for analogue light source was produced.

In addition, the electric charge transferring materials used in the Examples are shown by the number of the above compounds in Table 61, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 61.

TABLE 61

| Example No. | CTM | | $V_0$ | Vr | $E_{1/2}$ | $\Delta V_0$ | $\Delta$Vr |
|---|---|---|---|---|---|---|---|
| 444 | 11-2 | 71-1 | −703 | −28 | 0.52 | −41 | +10 |
| 445 | 11-2 | 71-2 | −698 | −25 | 0.50 | −35 | +9 |
| 446 | 11-2 | 71-3 | −700 | −27 | 0.49 | −38 | +10 |
| 447 | 11-11 | 71-1 | −691 | −25 | 0.50 | −41 | +8 |
| 448 | 13-2 | 71-1 | −714 | −27 | 0.50 | −39 | +10 |
| 449 | 11-2 | 72-1 | −701 | −26 | 0.49 | −39 | +8 |

Examples 450 to 455
(Multi-layer type electrophotosensitive material for analogue light source)

According to the same manner as that described in Examples 408 to 413 except for using 2.5 parts by weight of the bisazo pigment represented by the above formula (10-6) as the electric charge generating material, a multi-layer type electrophotosensitive material for analogue light source was produced.

In addition, the electric charge transferring materials used in the Examples are shown by the number of the above compounds in Table 62, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 62.

TABLE 62

| Example No. | CTM | | $V_0$ | Vr | $E_{1/2}$ | $\Delta V_0$ | $\Delta$Vr |
|---|---|---|---|---|---|---|---|
| 450 | 11-2 | 71-1 | −709 | −23 | 0.52 | −25 | ±0 |
| 451 | 11-2 | 71-2 | −698 | −19 | 0.50 | −20 | +5 |
| 452 | 11-2 | 71-3 | −693 | −20 | 0.48 | −22 | +2 |
| 453 | 11-11 | 71-1 | −711 | −21 | 0.51 | −23 | +14 |
| 454 | 13-2 | 71-1 | −700 | −21 | 0.49 | −23 | +3 |
| 455 | 11-2 | 72-1 | −703 | −21 | 0.51 | −24 | +11 |

Examples 456 to 461
(Multi-layer type electrophotosensitive material for analogue light source)

According to the same manner as that described in Examples 408 to 413 except for using 2.5 parts by weight of the bisazo pigment represented by the above formula (10-7) as the electric charge generating material, a multi-layer type electrophotosensitive material for analogue light source was produced.

In addition, the electric charge transferring materials used in the Examples are shown by the number of the above compounds in Table 63, according to the same manner as that described above.

The electrophotosensitive materials of the above respective Examples were subjected to the above initial electric characteristics test (IV) and electric characteristics test (IV) after repeated exposure, and their characteristics were evaluated. The results are shown in Table 63.

TABLE 63

| Example No. | CTM | | $V_0$ | Vr | $E_{1/2}$ | $\Delta V_0$ | $\Delta$Vr |
|---|---|---|---|---|---|---|---|
| 456 | 11-2 | 71-1 | −691 | −25 | 0.51 | −20 | +10 |
| 457 | 11-2 | 71-2 | −703 | −22 | 0.48 | −18 | +5 |
| 458 | 11-2 | 71-3 | −708 | −23 | 0.45 | −15 | +5 |
| 459 | 11-11 | 71-1 | −699 | −25 | 0.47 | −20 | ±0 |
| 460 | 13-2 | 71-1 | −710 | −24 | 0.47 | −19 | +6 |
| 461 | 11-2 | 72-1 | −698 | −24 | 0.46 | −19 | +2 |

Examples 462 to 469
(Single-layer type electrophotosensitive material for analogue light source)

According to the same manner as that described in Examples 145 to 151 except for using 50 parts by weight of the naphthylenediamine derivative in combination with 50 parts by weight of the phenylenediamine derivative as the hole transferring material, a single-layer type electrophotosensitive material for analogue light source was produced.

The amount of the 2,4,7-trinitrofluorenonimine derivative was 30 parts by weight in all Examples. In addition, the hole transferring materials and electron transferring materials used in the Examples are shown by the number of the above compounds in Table 64, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 64.

TABLE 64

| Example | | | | Initial Characteristics | | | After Repeating | |
|---|---|---|---|---|---|---|---|---|
| No. | HTM | | ETM | $V_0$ | Vr | $E_{1/2}$ | $\Delta V_0$ | $\Delta Vr$ |
| 462 | 11-2 | 71-1 | 2-5 | 700 | 64 | 1.22 | −3 | −2 |
| 463 | 11-2 | 71-2 | 2-5 | 699 | 66 | 1.25 | −9 | −5 |
| 464 | 11-2 | 71-3 | 2-5 | 702 | 61 | 1.21 | −6 | +1 |
| 465 | 11-2 | 71-1 | 2-6 | 701 | 63 | 1.20 | −10 | ±0 |
| 466 | 11-11 | 71-1 | 2-5 | 700 | 63 | 1.26 | −5 | −1 |
| 467 | 11-11 | 71-1 | 2-6 | 698 | 59 | 1.22 | −5 | +5 |
| 468 | 13-2 | 71-1 | 2-5 | 705 | 65 | 1.24 | −10 | +8 |
| 469 | 13-2 | 71-1 | 2-16 | 703 | 70 | 1.27 | −10 | +3 |

Examples 470 to 477
(Single-layer type electrophotosensitive material for analogue light source)

According to the same manner as that described in Examples 462 to 469 except for using 5 parts by weight of the bisazo pigment represented by the above formula (10-1) as the electric charge generating material, a single-layer type electrophotosensitive material for analogue light source was produced.

The amount of the 2,4,7-trinitrofluorenonimine derivative was 30 parts by weight in all Examples. In addition, the hole transferring materials and electron transferring materials used in the Examples are shown by the number of the above compounds in Table 65, according to the same manner as that described above The electrophotosensitive materials of the above respective Examples were subjected to the above initial electric characteristics test (II) and electric characteristics test (II) after repeated exposure, and their characteristics were evaluated. The results are shown in Table 65.

TABLE 65

| Example | | | | Initial Characteristics | | | After Repeating | |
|---|---|---|---|---|---|---|---|---|
| No. | HTM | | ETM | $V_0$ | Vr | $E_{1/2}$ | $\Delta V_0$ | $\Delta Vr$ |
| 470 | 11-2 | 71-1 | 2-5 | 699 | 29 | 1.00 | −5 | +3 |
| 471 | 11-2 | 71-2 | 2-5 | 700 | 24 | 1.03 | −3 | ±0 |
| 472 | 11-2 | 71-3 | 2-5 | 704 | 26 | 1.05 | ±0 | −1 |
| 473 | 11-2 | 71-1 | 2-6 | 705 | 25 | 1.05 | +3 | −3 |
| 474 | 11-11 | 71-1 | 2-5 | 701 | 24 | 1.05 | +5 | −2 |
| 475 | 11-11 | 71-1 | 2-6 | 699 | 28 | 1.01 | −5 | −5 |
| 476 | 13-2 | 71-1 | 2-5 | 697 | 29 | 1.02 | −4 | −4 |
| 477 | 13-2 | 71-1 | 2-16 | 700 | 29 | 1.03 | −5 | −5 |

Examples 478 to 485
(Single-layer type electrophotosensitive material for analogue light source)

According to the same manner as that described in Examples 462 to 469 except for using 5 parts by weight of the bisazo pigment represented by the above formula (10-3) as the electric charge generating material, a single-layer type electrophotosensitive material for analogue light source was produced.

The amount of the 2,4,7-trinitrofluorenonimine derivative was 30 parts by weight in all Examples. In addition, the hole transferring materials and electron transferring materials used in the Examples are shown by the number of the above compounds in Table 66, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 66.

TABLE 66

| Example | | | | Initial Characteristics | | | After Repeating | |
|---|---|---|---|---|---|---|---|---|
| No. | HTM | | ETM | $V_0$ | Vr | $E_{1/2}$ | $\Delta V_0$ | $\Delta Vr$ |
| 478 | 11-2 | 71-1 | 2-5 | 701 | 19 | 1.03 | ±0 | ±0 |
| 479 | 11-2 | 71-2 | 2-5 | 700 | 21 | 1.05 | −3 | −4 |
| 480 | 11-2 | 71-3 | 2-5 | 700 | 18 | 1.02 | −5 | −5 |
| 481 | 11-2 | 71-1 | 2-6 | 697 | 23 | 1.06 | −10 | +3 |
| 482 | 11-11 | 71-1 | 2-5 | 702 | 23 | 1.05 | −8 | −3 |
| 483 | 11-11 | 71-1 | 2-6 | 704 | 25 | 1.07 | −10 | +5 |
| 484 | 13-2 | 71-1 | 2-5 | 701 | 17 | 1.04 | −5 | +1 |
| 485 | 13-2 | 71-1 | 2-16 | 700 | 20 | 1.04 | −10 | +3 |

Examples 486 to 493
(Single-layer type electrophotosensitive material for analogue light source)

Examples 462 to 469 except for using 5 parts by weight of the bisazo pigment represented by the above formula (10-5) as the electric charge generating material, a single-layer type electrophotosensitive material for analogue light source was produced.

The amount of the 2,4,7-trinitrofluorenonimine derivative was 30 parts by weight in all Examples. In addition, the hole transferring materials and electron transferring materials used in the Examples are shown by the number of the above compounds in Table 67, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 67.

TABLE 67

| Example | | | | Initial Characteristics | | | After Repeating | |
|---|---|---|---|---|---|---|---|---|
| No. | HTM | | ETM | $V_0$ | Vr | $E_{1/2}$ | $\Delta V_0$ | $\Delta Vr$ |
| 486 | 11-2 | 71-1 | 2-5 | 705 | 40 | 1.10 | −10 | +5 |
| 487 | 11-2 | 71-2 | 2-5 | 698 | 38 | 1.10 | −8 | +5 |
| 488 | 11-2 | 71-3 | 2-5 | 697 | 39 | 1.10 | −10 | +5 |
| 489 | 11-2 | 71-1 | 2-6 | 698 | 32 | 1.11 | −10 | +8 |
| 490 | 11-11 | 71-1 | 2-5 | 699 | 38 | 1.09 | −5 | +10 |
| 491 | 11-11 | 71-1 | 2-6 | 701 | 35 | 1.10 | −9 | +6 |
| 492 | 13-2 | 71-1 | 2-5 | 702 | 37 | 1.13 | −10 | +10 |
| 493 | 13-2 | 71-1 | 2-16 | 699 | 37 | 1.14 | −10 | +10 |

Examples 494 to 501
(Single-layer type electrophotosensitive material for analogue light source)

According to the same manner as that described in Examples 462 to 469 except for using 5 parts by weight of the bisazo pigment represented by the above formula (10-6) as the electric charge generating material, a single-layer type electrophotosensitive material for analogue light source was produced.

The amount of the 2,4,7-trinitrofluorenonimine derivative was 30 parts by weight in all Examples. In addition, the hole transferring materials and electron transferring materials used in the Examples are shown by the number of the above compounds in Table 68, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 68.

TABLE 68

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 494 | 11-2 | 71-1 | 2-5 | 702 | 35 | 1.14 | −10 | +3 |
| 495 | 11-2 | 71-2 | 2-5 | 700 | 42 | 1.16 | −10 | +5 |
| 496 | 11-2 | 71-3 | 2-5 | 700 | 33 | 1.16 | −8 | +10 |
| 497 | 11-2 | 71-1 | 2-6 | 701 | 44 | 1.16 | −7 | +5 |
| 498 | 11-11 | 71-1 | 2-5 | 706 | 40 | 1.15 | −5 | +5 |
| 499 | 11-11 | 71-1 | 2-6 | 705 | 45 | 1.17 | −10 | +6 |
| 500 | 13-2 | 71-1 | 2-5 | 707 | 42 | 1.15 | −9 | +6 |
| 501 | 13-2 | 71-1 | 2-16 | 698 | 44 | 1.16 | −10 | +6 |

Examples 502 to 509
(Single-layer type electrophotosensitive material for digital light source)

According to the same manner as that described in Examples 180 to 188 except for using 50 parts by weight of the naphthylenediamine derivative in combination with 50 parts by weight of the phenylenediamine derivative as the hole transferring material, a single-layer type electrophotosensitive material for digital light source was produced.

The amount of the diphenoquinone derivative was 30 parts by weight in all Examples. In addition, the hole transferring materials and electron transferring materials used in the Examples are shown by the number of the above compounds in Table 69, according to the same manner as that described above.

The electrophotosensitive materials of the above respective Examples were subjected to the above initial electric characteristics test (I) and electric characteristics test (I) after repeated exposure, and their characteristics were evaluated. The results are shown in Table 69.

TABLE 69

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 502 | 11-2 | 71-1 | 3-1 | 710 | 25 | 1.25 | −10 | +5 |
| 503 | 11-2 | 71-2 | 3-1 | 708 | 20 | 1.20 | −10 | +7 |
| 504 | 11-2 | 71-3 | 3-1 | 695 | 24 | 1.20 | −8 | +8 |
| 505 | 11-11 | 71-1 | 3-1 | 713 | 20 | 1.18 | −9 | +6 |
| 506 | 13-2 | 71-1 | 3-1 | 713 | 20 | 1.20 | −10 | +6 |
| 507 | 11-2 | 71-1 | 3-3 | 708 | 23 | 1.21 | −8 | +5 |
| 508 | 11-2 | 71-1 | 3-7 | 712 | 25 | 1.20 | −10 | +5 |
| 509 | 11-2 | 72-1 | 3-1 | 705 | 21 | 1.20 | −9 | +8 |

Examples 510 to 517
(Single-layer type electrophotosensitive material for analogue light source)

According to the same manner as that described in Examples 502 to 509 except for using 5 parts by weight of the perylene pigment represented by the above formula (9-1) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 70, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 70.

TABLE 70

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 510 | 11-2 | 71-1 | 3-1 | 703 | 106 | 1.65 | −7 | +6 |
| 511 | 11-2 | 71-2 | 3-1 | 695 | 99 | 1.60 | −4 | +8 |
| 512 | 11-2 | 71-3 | 3-1 | 712 | 102 | 1.63 | −1 | +8 |
| 513 | 11-11 | 71-1 | 3-1 | 698 | 101 | 1.62 | −5 | +5 |
| 514 | 13-2 | 71-1 | 3-1 | 700 | 105 | 1.64 | −9 | +7 |
| 515 | 11-2 | 71-1 | 3-3 | 710 | 105 | 1.63 | −10 | +9 |
| 516 | 11-2 | 71-1 | 3-7 | 713 | 99 | 1.63 | −5 | +5 |
| 517 | 11-2 | 72-1 | 3-1 | 697 | 101 | 1.63 | −5 | +8 |

Examples 518 to 525
(Single-layer type electrophotosensitive material for analogue light source)

According to the same manner as that described in Examples 502 to 509 except for using 5 parts by weight of the bisazo pigment represented by the above formula (10-1) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 71, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 71.

TABLE 71

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 518 | 11-2 | 71-1 | 3-1 | 705 | 35 | 1.22 | −10 | ±0 |
| 519 | 11-2 | 71-2 | 3-1 | 708 | 30 | 1.20 | −9 | +5 |
| 520 | 11-2 | 71-3 | 3-1 | 695 | 33 | 1.21 | −5 | +2 |
| 521 | 11-11 | 71-1 | 3-1 | 712 | 34 | 1.19 | −9 | +3 |
| 522 | 13-2 | 71-1 | 3-1 | 702 | 34 | 1.20 | −7 | +5 |
| 523 | 11-2 | 71-1 | 3-3 | 705 | 31 | 1.20 | −8 | +5 |
| 524 | 11-2 | 71-1 | 3-7 | 707 | 30 | 1.19 | −8 | +4 |
| 525 | 11-2 | 72-1 | 3-1 | 711 | 32 | 1.21 | −8 | +3 |

Examples 526 to 533
(Single-layer type electrophotosensitive material for analogue light source)

According to the same manner as that described in Examples 502 to 509 except for using 5 parts by weight of the bisazo pigment represented by the above formula (10-2) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 72, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 72.

TABLE 72

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 526 | 11-2 | 71-1 | 3-1 | 710 | 30 | 1.20 | −10 | +8 |
| 527 | 11-2 | 71-2 | 3-1 | 700 | 28 | 1.15 | −7 | +5 |
| 528 | 11-2 | 71-3 | 3-1 | 695 | 25 | 1.15 | −7 | +8 |
| 529 | 11-11 | 71-1 | 3-1 | 698 | 29 | 1.18 | −8 | +9 |
| 530 | 13-2 | 71-1 | 3-1 | 702 | 30 | 1.17 | −10 | +10 |
| 531 | 11-2 | 71-1 | 3-3 | 713 | 29 | 1.19 | −9 | +5 |
| 532 | 11-2 | 71-1 | 3-7 | 705 | 25 | 1.18 | −9 | +5 |
| 533 | 11-2 | 72-1 | 3-1 | 706 | 29 | 1.16 | −8 | +6 |

Examples 534 to 541
(Single-layer type electrophotosensitive material for analogue light source)

According to the same manner as that described in Examples 502 to 509 except for using 5 parts by weight of the bisazo pigment represented by the above formula (10-3) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 73, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 73.

TABLE 73

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 534 | 11-2 | 71-1 | 3-1 | 695 | 28 | 1.25 | −9 | +8 |
| 535 | 11-2 | 71-2 | 3-1 | 695 | 25 | 1.20 | −9 | +5 |
| 536 | 11-2 | 71-3 | 3-1 | 700 | 25 | 1.21 | −10 | +5 |
| 537 | 11-11 | 71-1 | 3-1 | 704 | 26 | 1.24 | −8 | +9 |
| 538 | 13-2 | 71-1 | 3-1 | 705 | 30 | 1.18 | −9 | +10 |
| 539 | 11-2 | 71-1 | 3-3 | 691 | 29 | 1.19 | −10 | +15 |
| 540 | 11-2 | 71-1 | 3-7 | 715 | 27 | 1.20 | −5 | +10 |
| 541 | 11-2 | 72-1 | 3-1 | 713 | 26 | 1.19 | −10 | +7 |

Examples 542 to 549
(Single-layer type electrophotosensitive material for analogue light source)

According to the same manner as that described in Examples 502 to 509 except for using 5 parts by weight of the bisazo pigment represented by the above formula (10-4) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 74, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 74.

TABLE 74

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 542 | 11-2 | 71-1 | 3-1 | 699 | 18 | 1.08 | −10 | +10 |
| 543 | 11-2 | 71-2 | 3-1 | 712 | 20 | 1.05 | −11 | +9 |
| 544 | 11-2 | 71-3 | 3-1 | 702 | 19 | 1.05 | −8 | +8 |
| 545 | 11-11 | 71-1 | 3-1 | 714 | 19 | 1.08 | −9 | +8 |
| 546 | 13-2 | 71-1 | 3-1 | 708 | 17 | 1.07 | −10 | +10 |
| 547 | 11-2 | 71-1 | 3-3 | 711 | 15 | 1.07 | −7 | +11 |
| 548 | 11-2 | 71-1 | 3-7 | 698 | 20 | 1.08 | −8 | +10 |
| 549 | 11-2 | 72-1 | 3-1 | 701 | 19 | 1.06 | −12 | +9 |

Examples 550 to 557
(Single-layer type electrophotosensitive material for analogue light source)

According to the same manner as that described in Examples 502 to 509 except for using 5 parts by weight of the bisazo pigment represented by the above formula (10-5) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 75, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 75.

TABLE 75

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 550 | 11-2 | 71-1 | 3-1 | 702 | 39 | 1.22 | −7 | +2 |
| 551 | 11-2 | 71-2 | 3-1 | 691 | 40 | 1.20 | −8 | +1 |
| 552 | 11-2 | 71-3 | 3-1 | 695 | 35 | 1.18 | −5 | ±0 |
| 553 | 11-11 | 71-1 | 3-1 | 701 | 38 | 1.20 | −4 | +5 |
| 554 | 13-2 | 71-1 | 3-1 | 710 | 40 | 1.21 | −8 | +3 |
| 555 | 11-2 | 71-1 | 3-3 | 711 | 37 | 1.18 | −7 | +3 |
| 556 | 11-2 | 71-1 | 3-7 | 712 | 36 | 1.20 | −3 | +1 |
| 557 | 11-2 | 72-1 | 3-1 | 714 | 36 | 1.19 | −4 | +2 |

Examples 558 to 565

(Single-layer type electrophotosensitive material for analogue light source)

According to the same manner as that described in Examples 502 to 509 except for using 5 parts by weight of the bisazo pigment represented by the above formula (10-6) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 76, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 76.

TABLE 76

| Example | | | Initial Characteristics | | | After Repeating | |
|---|---|---|---|---|---|---|---|
| No. | HTM | ETM | $V_0$ | Vr | $E_{1/2}$ | $\Delta V_0$ | $\Delta Vr$ |
| 558 | 11-2 | 71-1 | 3-1 | 706 | 30 | 1.10 | −10 | ±0 |
| 559 | 11-2 | 71-2 | 3-1 | 713 | 35 | 1.08 | −9 | +5 |
| 560 | 11-2 | 71-3 | 3-1 | 704 | 30 | 1.10 | −8 | +3 |
| 561 | 11-11 | 71-1 | 3-1 | 695 | 36 | 1.12 | −8 | +1 |
| 562 | 13-2 | 71-1 | 3-1 | 698 | 37 | 1.10 | −9 | +4 |
| 563 | 11-2 | 71-1 | 3-3 | 694 | 32 | 1.09 | −5 | +2 |
| 564 | 11-2 | 71-1 | 3-7 | 708 | 34 | 1.07 | −10 | +2 |
| 565 | 11-2 | 72-1 | 3-1 | 702 | 32 | 1.11 | −9 | +4 |

Examples 566 to 573

(Single-layer type electrophotosensitive material for analogue light source)

According to the same manner as that described in Examples 502 to 509 except for using 5 parts by weight of the bisazo pigment represented by the above formula (10-7) as the electric charge generating material, a single-layer type electrophotosensitive material for analogue light source was produced.

The amount of the diphenoquinone derivative was 30 parts by weight in all Examples. In addition, the hole transferring materials and electron transferring materials used in the Examples are shown by the number of the above compounds in Table 77, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 77.

TABLE 77

| Example | | | Initial Characteristics | | | After Repeating | |
|---|---|---|---|---|---|---|---|
| No. | HTM | ETM | $V_0$ | Vr | $E_{1/2}$ | $\Delta V_0$ | $\Delta Vr$ |
| 566 | 11-2 | 71-1 | 3-1 | 714 | 32 | 1.20 | −7 | ±0 |
| 567 | 11-2 | 71-2 | 3-1 | 698 | 30 | 1.18 | −5 | +5 |
| 568 | 11-2 | 71-3 | 3-1 | 710 | 28 | 1.17 | −7 | +4 |
| 569 | 11-11 | 71-1 | 3-1 | 700 | 35 | 1.15 | −6 | +2 |

TABLE 77-continued

| Example | | | Initial Characteristics | | | After Repeating | |
|---|---|---|---|---|---|---|---|
| No. | HTM | ETM | $V_0$ | Vr | $E_{1/2}$ | $\Delta V_0$ | $\Delta Vr$ |
| 570 | 13-2 | 71-1 | 3-1 | 705 | 38 | 1.17 | −8 | +2 |
| 571 | 11-2 | 71-1 | 3-3 | 708 | 34 | 1.18 | −8 | +2 |
| 572 | 11-2 | 71-1 | 3-7 | 709 | 39 | 1.18 | −9 | +1 |
| 573 | 11-2 | 72-1 | 3-1 | 694 | 38 | 1.17 | −7 | ±0 |

Examples 574 to 583

(Single-layer type electrophotosensitive material for analogue light source)

According to the same manner as that described in Examples 224 to 233 except for using 50 parts by weight of the naphthylenediamine derivative in combination with 50 parts by weight of the phenylenediamine derivative as the hole transferring material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 78, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 78.

TABLE 78

| Example | | | Initial Characteristics | | | After Repeating | |
|---|---|---|---|---|---|---|---|
| No. | HTM | ETM | $V_0$ | Vr | $E_{1/2}$ | $\Delta V_0$ | $\Delta Vr$ |
| 574 | 11-2 | 71-1 | 4-2 | 704 | 62 | 1.22 | −13 | −5 |
| 575 | 11-2 | 71-2 | 4-2 | 701 | 60 | 1.20 | −15 | −6 |
| 576 | 11-2 | 71-3 | 4-2 | 700 | 63 | 1.22 | −14 | −8 |
| 577 | 11-2 | 71-1 | 4-1 | 696 | 65 | 1.23 | −15 | −6 |
| 578 | 11-2 | 71-1 | 4-3 | 699 | 68 | 1.25 | −11 | −5 |
| 579 | 11-2 | 71-1 | 4-4 | 700 | 68 | 1.25 | −13 | +8 |
| 580 | 11-11 | 71-1 | 4-1 | 703 | 64 | 1.24 | −15 | −6 |
| 581 | 11-11 | 71-1 | 4-2 | 706 | 61 | 1.21 | −16 | −7 |
| 582 | 13-2 | 71-1 | 4-3 | 705 | 67 | 1.25 | −17 | −4 |
| 583 | 13-2 | 72-1 | 4-4 | 701 | 68 | 1.25 | −15 | +5 |

Examples 584 to 593

(Single-layer type electrophotosensitive material for analogue light source)

According to the same manner as that described in Examples 574 to 583 except for using 5 parts by weight of the bisazo pigment represented by the above formula (10-1) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 79, according to the same manner as that described above.

The electrophotosensitive materials of the above respective Examples were subjected to the above initial electric characteristics test (II) and electric characteristics test (II)

after repeated exposure, and their characteristics were evaluated. The results are shown in Table 79.

TABLE 79

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 584 | 11-2 | 71-1 | 4-2 | 700 | 30 | 1.10 | −5 | ±0 |
| 585 | 11-2 | 71-2 | 4-2 | 700 | 33 | 1.13 | −4 | −2 |
| 586 | 11-2 | 71-3 | 4-2 | 698 | 32 | 1.11 | −3 | −3 |
| 587 | 11-2 | 71-1 | 4-1 | 695 | 33 | 1.12 | −6 | −6 |
| 588 | 11-2 | 71-1 | 4-3 | 705 | 40 | 1.16 | −5 | −5 |
| 589 | 11-2 | 71-1 | 4-4 | 701 | 42 | 1.17 | −5 | +5 |
| 590 | 11-11 | 71-1 | 4-1 | 706 | 35 | 1.15 | −6 | −5 |
| 591 | 11-11 | 71-1 | 4-2 | 700 | 33 | 1.12 | −3 | −2 |
| 592 | 13-2 | 71-1 | 4-3 | 704 | 38 | 1.15 | −2 | −3 |
| 593 | 13-2 | 72-1 | 4-4 | 700 | 37 | 1.15 | −5 | +5 |

Examples 594 to 603
(Single-layer type electrophotosensitive material for analogue light source)

According to the same manner as that described in Examples 574 to 583 except for using 5 parts by weight of the bisazo pigment represented by the above formula (10-3) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 80, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 80.

TABLE 80

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 594 | 11-2 | 71-1 | 4-2 | 705 | 28 | 1.08 | ±0 | ±0 |
| 595 | 11-2 | 71-2 | 4-2 | 703 | 31 | 1.08 | ±0 | +2 |
| 596 | 11-2 | 71-3 | 4-2 | 707 | 33 | 1.10 | ±0 | −3 |
| 597 | 11-2 | 71-1 | 4-1 | 695 | 35 | 1.12 | −5 | −5 |
| 598 | 11-2 | 71-1 | 4-3 | 693 | 37 | 1.12 | −5 | −5 |
| 599 | 11-2 | 71-1 | 4-4 | 701 | 40 | 1.15 | −5 | +5 |
| 600 | 11-11 | 71-1 | 4-1 | 700 | 32 | 1.08 | −6 | −5 |
| 601 | 11-11 | 71-1 | 4-2 | 700 | 30 | 1.00 | ±0 | ±0 |
| 602 | 13-2 | 71-1 | 4-3 | 704 | 36 | 1.12 | −4 | −3 |
| 603 | 13-2 | 72-1 | 4-4 | 707 | 35 | 1.15 | −7 | +5 |

Examples 604 to 613
(Single-layer type electrophotosensitive material for analogue light source)

According to the same manner as that described in Examples 574 to 583 except for using 5 parts by weight of the bisazo pigment represented by the above formula (10-5) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 81, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 81.

TABLE 81

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 604 | 11-2 | 71-1 | 4-2 | 695 | 40 | 1.15 | ±0 | +2 |
| 605 | 11-2 | 71-2 | 4-2 | 700 | 43 | 1.17 | −6 | +4 |
| 606 | 11-2 | 71-3 | 4-2 | 704 | 41 | 1.15 | −5 | +3 |
| 607 | 11-2 | 71-1 | 4-1 | 701 | 43 | 1.17 | −4 | +2 |
| 608 | 11-2 | 71-1 | 4-3 | 700 | 45 | 1.20 | −7 | +1 |
| 609 | 11-2 | 71-1 | 4-4 | 693 | 46 | 1.20 | −8 | +6 |
| 610 | 11-11 | 71-1 | 4-1 | 705 | 43 | 1.16 | −5 | +3 |
| 611 | 11-11 | 71-1 | 4-2 | 708 | 44 | 1.17 | −3 | −2 |
| 612 | 13-2 | 71-1 | 4-3 | 700 | 46 | 1.20 | −10 | +3 |
| 613 | 13-2 | 72-1 | 4-4 | 704 | 46 | 1.20 | −10 | +8 |

Examples 614 to 623
(Single-layer type electrophotosensitive material for analogue light source)

According to the same manner as that described in Examples 574 to 583 except for using 5 parts by weight of the bisazo pigment represented by the above formula (10-6) as the electric charge generating material, a single-layer type electrophotosensitive material for analogue light source was produced.

The amount of the ethylated nitrofluorenonimine derivative was 30 parts by weight in all Examples. In addition, the hole transferring materials and electron transferring materials used in the Examples are shown by the number of the above compounds in Table 82, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 82.

TABLE 82

| Example No. | HTM | ETM | Initial Characteristics | | | After Repeating | |
|---|---|---|---|---|---|---|---|
| | | | $V_0$ | Vr | $E_{1/2}$ | $\Delta V_0$ | $\Delta Vr$ |
| 614 | 11-2 | 71-1 | 4-2 | 706 | 44 | 1.13 | −5 | −5 |
| 615 | 11-2 | 71-2 | 4-2 | 707 | 42 | 1.13 | −4 | −3 |
| 616 | 11-2 | 71-3 | 4-2 | 699 | 45 | 1.16 | −5 | −4 |
| 617 | 11-2 | 71-1 | 4-1 | 700 | 44 | 1.16 | −6 | −3 |
| 618 | 11-2 | 71-1 | 4-3 | 695 | 48 | 1.18 | −8 | +4 |
| 619 | 11-2 | 71-1 | 4-4 | 704 | 47 | 1.20 | −10 | +9 |
| 620 | 11-11 | 71-1 | 4-1 | 700 | 45 | 1.14 | −10 | −5 |
| 621 | 11-11 | 71-1 | 4-2 | 705 | 43 | 1.12 | −5 | −3 |
| 622 | 13-2 | 71-1 | 4-3 | 703 | 48 | 1.13 | −8 | +3 |
| 623 | 13-2 | 72-1 | 4-4 | 701 | 49 | 1.14 | −12 | +10 |

Examples 624 to 631
(Single-layer type electrophotosensitive material for analogue light source)

According to the same manner as that described in Examples 274 to 280 except for using 50 parts by weight of the naphthylenediamine derivative in combination with 50 parts by weight of the phenylenediamine derivative as the hole transferring material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 83, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 83.

TABLE 83

| Example No. | Characteristics | | Initial Repeating | | | After | |
|---|---|---|---|---|---|---|---|
| | HTM | ETM | $V_0$ | Vr | $E_{1/2}$ | $\Delta V_0$ | $\Delta Vr$ |
| 624 | 11-2 | 71-1 | 5-1 | 708 | 69 | 1.13 | −9 | +3 |
| 625 | 11-2 | 71-2 | 5-1 | 705 | 62 | 1.10 | −5 | +5 |
| 626 | 11-2 | 71-3 | 5-1 | 702 | 68 | 1.13 | −10 | +3 |
| 627 | 11-2 | 71-1 | 5-4 | 695 | 65 | 1.12 | −6 | +1 |
| 628 | 11-11 | 71-1 | 5-1 | 697 | 63 | 1.11 | −6 | +1 |
| 629 | 11-11 | 71-1 | 5-4 | 701 | 63 | 1.11 | −7 | +4 |
| 630 | 13-2 | 71-1 | 5-1 | 704 | 68 | 1.13 | −10 | +5 |
| 631 | 13-2 | 71-1 | 5-4 | 704 | 70 | 1.15 | −10 | +5 |

Examples 632 to 639
(Single-layer type electrophotosensitive material for analogue light source)

According to the same manner as that described in Examples 624 to 631 except for using 5 parts by weight of the bisazo pigment represented by the above formula (10-1) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 84, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 84.

TABLE 84

| Example No. | Characteristics | | Initial Repeating | | | After | |
|---|---|---|---|---|---|---|---|
| | HTM | ETM | $V_0$ | Vr | $E_{1/2}$ | $\Delta V_0$ | $\Delta Vr$ |
| 632 | 11-2 | 71-1 | 5-1 | 699 | 48 | 1.00 | −12 | +8 |
| 633 | 11-2 | 71-2 | 5-1 | 703 | 42 | 0.98 | −13 | +6 |
| 634 | 11-2 | 71-3 | 5-1 | 702 | 40 | 0.96 | −15 | +10 |
| 635 | 11-2 | 71-1 | 5-4 | 709 | 48 | 0.99 | −10 | +5 |
| 636 | 11-11 | 71-1 | 5-1 | 698 | 45 | 0.99 | −10 | +4 |
| 637 | 11-11 | 71-1 | 5-4 | 701 | 46 | 0.99 | −13 | +7 |
| 638 | 13-2 | 71-1 | 5-1 | 704 | 45 | 0.99 | −11 | +6 |
| 639 | 13-2 | 71-1 | 5-4 | 706 | 47 | 0.99 | −16 | +10 |

Examples 640 to 647
(Single-layer type electrophotosensitive material for analogue light source)

According to the same manner as that described in Examples 624 to 631 except for using 5 parts by weight of the bisazo pigment represented by the above formula (10-3) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 85, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 85.

TABLE 85

| Example No. | Characteristics | | Initial Repeating | | | After | |
|---|---|---|---|---|---|---|---|
| | HTM | ETM | $V_0$ | Vr | $E_{1/2}$ | $\Delta V_0$ | $\Delta Vr$ |
| 640 | 11-2 | 71-1 | 5-1 | 703 | 41 | 1.00 | −16 | +7 |
| 641 | 11-2 | 71-2 | 5-1 | 702 | 40 | 1.00 | −15 | +9 |
| 642 | 11-2 | 71-3 | 5-1 | 695 | 38 | 0.99 | −10 | +5 |
| 643 | 11-2 | 71-1 | 5-4 | 700 | 42 | 1.00 | −13 | +6 |
| 644 | 11-11 | 71-1 | 5-1 | 702 | 40 | 1.00 | −11 | +3 |
| 645 | 11-11 | 71-1 | 5-4 | 702 | 45 | 1.02 | −13 | +6 |
| 646 | 13-2 | 71-1 | 5-1 | 706 | 41 | 1.00 | −14 | +10 |
| 647 | 13-2 | 71-1 | 5-4 | 700 | 43 | 1.00 | −14 | +8 |

Examples 648 to 655
(Single-layer type electrophotosensitive material for analogue light source)

According to the same manner as that described in Examples 624 to 631 except for using 5 parts by weight of the bisazo pigment represented by the above formula (10-5) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 86, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 86.

TABLE 86

| Example No. | Characteristics | | Initial Repeating | | | After | |
|---|---|---|---|---|---|---|---|
| | HTM | ETM | $V_0$ | Vr | $E_{1/2}$ | $\Delta V_0$ | $\Delta Vr$ |
| 648 | 11-2 | 71-1 | 5-1 | 701 | 43 | 1.00 | −12 | +6 |
| 649 | 11-2 | 71-2 | 5-1 | 698 | 45 | 1.02 | −14 | +7 |
| 650 | 11-2 | 71-3 | 5-1 | 700 | 41 | 1.00 | −16 | +10 |
| 651 | 11-2 | 71-1 | 5-4 | 705 | 43 | 1.00 | −15 | +9 |

TABLE 86-continued

| Example No. | Characteristics HTM | ETM | Initial Repeating V₀ | Vr | E₁/₂ | After ΔV₀ | ΔVr |
|---|---|---|---|---|---|---|---|
| 652 | 11-11 | 71-1 | 5-1 | 697 | 42 | 1.00 | -15 | +8 |
| 653 | 11-11 | 71-1 | 5-4 | 699 | 42 | 1.00 | -13 | +6 |
| 654 | 13-2 | 71-1 | 5-1 | 700 | 40 | 1.00 | -11 | +4 |
| 655 | 13-2 | 71-1 | 5-4 | 703 | 45 | 1.03 | -16 | +7 |

Examples 656 to 663
(Single-layer type electrophotosensitive material for analogue light source)

According to the same manner as that described in Examples 624 to 631 except for using 5 parts by weight of the bisazo pigment represented by the above formula (10-6) as the electric charge generating material, a single-layer type electrophotosensitive material for analogue light source was produced.

The amount of the tryptoanthrine derivative was 30 parts by weight in all Examples. In addition, the hole transferring materials and electron transferring materials used in the Examples are shown by the number of the above compounds in Table 87, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 87.

TABLE 87

| Example No. | Characteristics HTM | ETM | Initial Repeating V₀ | Vr | E₁/₂ | After ΔV₀ | ΔVr |
|---|---|---|---|---|---|---|---|
| 656 | 11-2 | 71-1 | 5-1 | 700 | 46 | 1.02 | -15 | +10 |
| 657 | 11-2 | 71-2 | 5-1 | 699 | 43 | 1.00 | -13 | +8 |
| 658 | 11-2 | 71-3 | 5-1 | 704 | 45 | 1.02 | -18 | +11 |
| 659 | 11-2 | 71-1 | 5-4 | 703 | 43 | 1.00 | -15 | +9 |
| 660 | 11-11 | 71-1 | 5-1 | 704 | 42 | 1.00 | -16 | +8 |
| 661 | 11-11 | 71-1 | 5-4 | 706 | 43 | 1.00 | -13 | +6 |
| 662 | 13-2 | 71-1 | 5-1 | 694 | 46 | 1.03 | -15 | +7 |
| 663 | 13-2 | 71-1 | 5-4 | 700 | 45 | 1.03 | -15 | +7 |

Examples 664 to 671
(Single-layer type electrophotosensitive material for analogue light source)

According to the same manner as that described in Examples 309 to 317 except for using 50 parts by weight of the naphthylenediamine derivative in combination with 50 parts by weight of the phenylenediamine derivative as the hole transferring material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 88, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 88.

TABLE 88

| Example No. | Characteristics HTM | ETM | Initial Repeating V₀ | Vr | E₁/₂ | After ΔV₀ | ΔVr |
|---|---|---|---|---|---|---|---|
| 664 | 11-2 | 71-1 | 6-3 | 702 | 60 | 1.32 | -16 | +6 |
| 665 | 11-2 | 71-2 | 6-3 | 700 | 63 | 1.33 | -13 | +5 |
| 666 | 11-2 | 71-3 | 6-3 | 705 | 65 | 1.36 | -11 | +8 |
| 667 | 11-2 | 71-1 | 6-10 | 701 | 69 | 1.40 | -16 | +8 |
| 668 | 11-11 | 71-1 | 6-3 | 694 | 63 | 1.35 | -15 | +9 |
| 669 | 11-11 | 71-1 | 6-6 | 707 | 75 | 1.45 | -14 | +7 |
| 670 | 13-2 | 71-1 | 6-3 | 699 | 62 | 1.30 | -10 | +5 |
| 671 | 13-2 | 71-1 | 6-10 | 701 | 70 | 1.35 | -14 | +7 |

Examples 672 to 679
(Single-layer type electrophotosensitive material for analogue light source)

According to the same manner as that described in Examples 664 to 671 except for using 5 parts by weight of the bisazo pigment represented by the above formula (10-1) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 89, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 89.

TABLE 89

| Example No. | Characteristics HTM | ETM | Initial Repeating V₀ | Vr | E₁/₂ | After ΔV₀ | ΔVr |
|---|---|---|---|---|---|---|---|
| 672 | 11-2 | 71-1 | 6-3 | 700 | 38 | 1.08 | -10 | +4 |
| 673 | 11-2 | 71-2 | 6-3 | 694 | 35 | 1.08 | -12 | +7 |
| 674 | 11-2 | 71-3 | 6-3 | 697 | 35 | 1.08 | -10 | +5 |
| 675 | 11-2 | 71-1 | 6-10 | 699 | 45 | 1.15 | -15 | +9 |
| 676 | 11-11 | 71-1 | 6-3 | 702 | 39 | 1.10 | -13 | +4 |
| 677 | 11-11 | 71-1 | 6-6 | 706 | 50 | 1.20 | -17 | +10 |
| 678 | 13-2 | 71-1 | 6-3 | 700 | 40 | 1.12 | -10 | +3 |
| 679 | 13-2 | 71-1 | 6-10 | 700 | 47 | 1.19 | -15 | +6 |

Examples 680 to 687
(Single-layer type electrophotosensitive material for analogue light source)

According to the same manner as that described in Examples 664 to 671 except for using 5 parts by weight of the bisazo pigment represented by the above formula (10-3) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 90, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 90.

TABLE 90

| Example No. | Characteristics HTM | ETM | Initial V₀ | Vr | E₁/₂ | After ΔV₀ | ΔVr |
|---|---|---|---|---|---|---|---|
| 680 | 11-2 | 71-1 | 6-3 | 703 | 27 | 1.00 | −3 | ±0 |
| 681 | 11-2 | 71-2 | 6-3 | 700 | 28 | 1.00 | ±0 | +4 |
| 682 | 11-2 | 71-3 | 6-3 | 702 | 30 | 1.05 | −5 | +3 |
| 683 | 11-2 | 71-1 | 6-10 | 698 | 36 | 1.07 | −7 | +2 |
| 684 | 11-11 | 71-1 | 6-3 | 701 | 26 | 1.00 | −4 | +4 |
| 685 | 11-11 | 71-1 | 6-6 | 706 | 40 | 1.10 | −13 | +6 |
| 686 | 13-2 | 71-1 | 6-3 | 703 | 30 | 1.05 | −5 | +5 |
| 687 | 13-2 | 71-1 | 6-10 | 700 | 35 | 1.06 | −8 | +5 |

Examples 688 to 695
(Single-layer type electrophotosensitive material for analogue light source)

According to the same manner as that described in Examples 664 to 671 except for using 5 parts by weight of the bisazo pigment represented by the above formula (10-5) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 91, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 91.

TABLE 91

| Example No. | Characteristics HTM | ETM | Initial V₀ | Vr | E₁/₂ | After ΔV₀ | ΔVr |
|---|---|---|---|---|---|---|---|
| 688 | 11-2 | 71-1 | 6-3 | 702 | 40 | 1.10 | −8 | +4 |
| 689 | 11-2 | 71-2 | 6-3 | 701 | 43 | 1.11 | −6 | +3 |
| 690 | 11-2 | 71-3 | 6-3 | 697 | 47 | 1.16 | −10 | +5 |
| 691 | 11-2 | 71-1 | 6-10 | 695 | 47 | 1.16 | −8 | +5 |
| 692 | 11-11 | 71-1 | 6-3 | 700 | 45 | 1.13 | −8 | +5 |
| 693 | 11-11 | 71-1 | 6-6 | 700 | 50 | 1.21 | −12 | +10 |
| 694 | 13-2 | 71-1 | 6-3 | 701 | 45 | 1.17 | −6 | +3 |
| 695 | 13-2 | 71-1 | 6-10 | 706 | 46 | 1.16 | −11 | +9 |

Examples 696 to 703
(Single-layer type electrophotosensitive material for analogue light source)

According to the same manner as that described in Examples 664 to 671 except for using 5 parts by weight of the bisazo pigment represented by the above formula (10-6) as the electric charge generating material, a single-layer type electrophotosensitive material for analogue light source was produced.

The amount of the tryptoanthrinimine derivative was 30 parts by weight in all Examples. In addition, the hole transferring materials and electron transferring materials used in the Examples are shown by the number of the above compounds in Table 92, according to the same manner as that described above.

The electrophotosensitive materials of the above respective Examples were subjected to the above initial electric characteristics test (II) and electric characteristics test (II) after repeated exposure, and their characteristics were evaluated. The results are shown in Table 92.

TABLE 92

| Example No. | Characteristics HTM | ETM | Initial V₀ | Vr | E₁/₂ | After ΔV₀ | ΔVr |
|---|---|---|---|---|---|---|---|
| 696 | 11-2 | 71-1 | 6-3 | 701 | 38 | 1.10 | −8 | +5 |
| 697 | 11-2 | 71-2 | 6-3 | 698 | 39 | 1.12 | −7 | +5 |
| 698 | 11-2 | 71-3 | 6-3 | 694 | 40 | 1.10 | −8 | +2 |
| 699 | 11-2 | 71-1 | 6-10 | 705 | 44 | 1.15 | −12 | +6 |
| 700 | 11-11 | 71-1 | 6-3 | 705 | 42 | 1.13 | −5 | +2 |
| 701 | 11-11 | 71-1 | 6-6 | 706 | 49 | 1.22 | −18 | +10 |
| 702 | 13-2 | 71-1 | 6-3 | 704 | 41 | 1.10 | −9 | +3 |
| 703 | 13-2 | 71-1 | 6-10 | 700 | 46 | 1.16 | −15 | +9 |

What is claimed is:

1. An electrophotosensitive material comprising a conductive substrate and a photosensitive layer further comprising a naphthylenediamine derivative represented by the general formula (1):

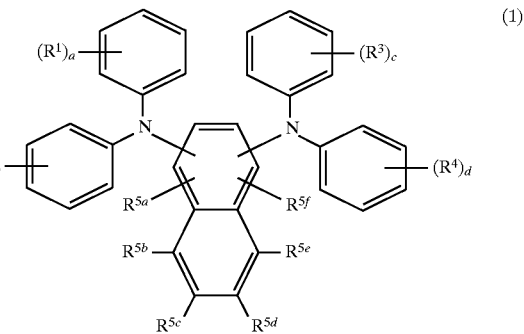

wherein $R^1$, $R^2$, $R^3$ and $R^4$ are the same or different and indicate a halogen atom, an alkyl group or an aryl group which may have an alkyl group; $R^{5a}$, $R^{5b}$, $R^{5c}$, $R^{5d}$, $R^{5d}$, $R^{5e}$ and $R^{5f}$ are the same or different and indicate a hydrogen atom, a halogen atom, a cyano group, a nitro group, an alkyl group or an aryl group; and a, b, c and d, which indicate substituting numbers of the groups $R^1$, $R^2$, $R^3$ and $R^4$, respectively, are the same or different and indicate an integer of 1 to 5.

2. The electrophotosensitive material of claim 1 further comprising:

a 2,4,7-trinitrofluorenonimine derivative represented by the general formula (2):

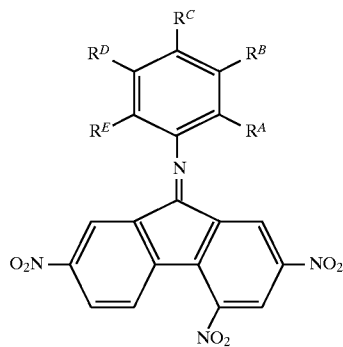

(2)

wherein $R^A$, $R^B$, $R^C$, $R^D$ and $R^E$ are the same or different and indicate a hydrogen atom, a halogen atom, an alkyl group which may have a substituent, an alkoxy group which may have a substituent, an aryl group which may have a substituent, an aralkyl group which may have a substituent or a phenoxy group which may have a substituent.

3. The electrophotosensitive material of claim 1 further comprising:
   a diphenoquinone derivative represented by the general formula (3):

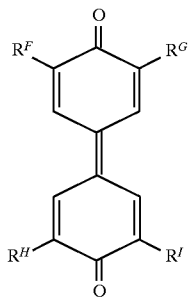

(3)

wherein $R^F$, $R^G$, $R^H$ and $R^I$ are the same or different and indicate a hydrogen atom, an alkyl group which may have a substituent, an alkoxy group which may have a substituent, an aryl group which may have a substituent or an aralkyl group which may have a substituent.

4. The electrophotosensitive material of claim 1 further comprising:
   an ethylated nitrofluorenonimine derivative represented by the general formula (4):

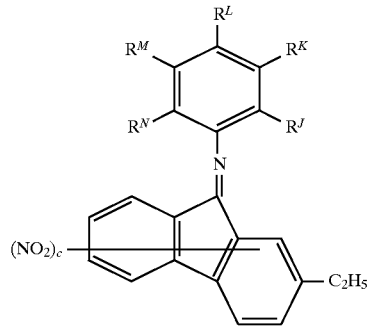

(4)

wherein $R^J$, $R^K$, $R^L$, $R^M$ and $R^N$ are the same or different and indicate a hydrogen atom, a halogen atom, an alkyl group which may have a substituent, an alkoxy group which may have a substituent, an aryl group which may have a substituent, an aralkyl group which may have a substituent or a phenoxy group which may have a substituent, and α is an integer of 1 to 4.

5. The electrophotosensitive material of claim 1 further comprising:
   a tryptoanthrine derivative represented by the general formula (5):

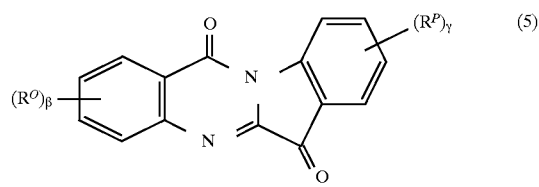

(5)

wherein $R^O$ and $R^P$ are the same or different and indicate an alkyl group which may have a substituent, an alkoxy group which may have a substituent or a nitro group; and β and γ are the same or different and indicate an integer of 0 to 3.

6. The electrophotosensitive material of claim 1 further comprising:
   a tryptoanthrinimine derivative represented by the general formula (6):

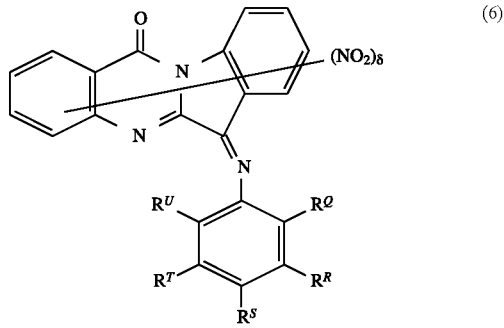

(6)

wherein $R^Q$, $R^R$, $R^S$, $R^T$ and $R^U$ are the same or different and indicate a hydrogen atom, a halogen atom, an alkyl group which may have a substituent, an alkoxy group which may have a substituent, an aryl group which may have a substituent, an aralkyl group which may have a substituent or a phenoxy group which may have a substituent; and δ is an integer of 1 to 4.

7. The electrophotosensitive material of claim 1 further comprising:
   a phenylenediamine derivative represented by the general formula (7):

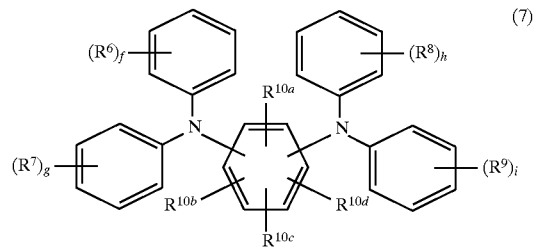

(7)

wherein $R^6$, $R^7$ $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

8. The electrophotosensitive material of claim 2 further comprising:

a phenylenediamine derivative represented by the general formula (7):

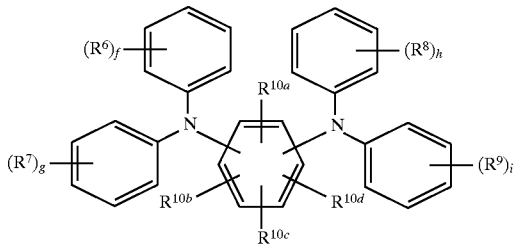

wherein $R^6$, $R^7$, $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

9. The electrophotosensitive material of claim 3 further comprising:

a phenylenediamine derivative represented by the general formula (7):

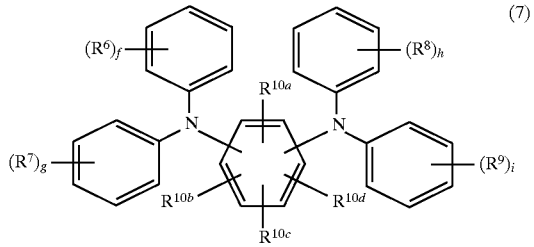

wherein $R^6$, $R^7$, $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

10. The electrophotosensitive material of claim 4 further comprising:

a phenylenediamine derivative represented by the general formula (7):

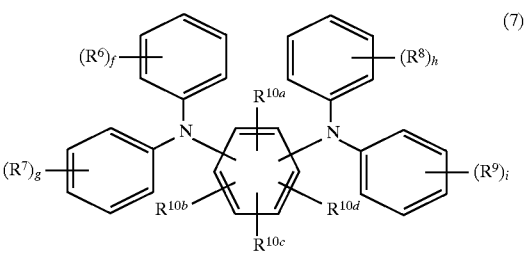

wherein $R^6$, $R^7$, $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

11. The electrophotosensitive material of claim 5 further comprising:

a phenylenediamine derivative represented by the general formula (7):

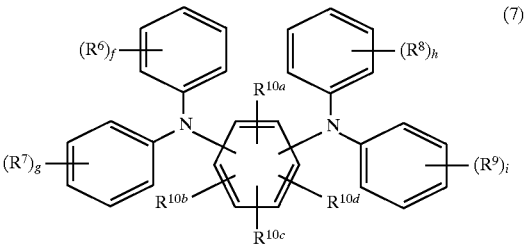

wherein $R^6$, $R^7$, $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

12. The electrophotosensitive material of claim 6 further comprising:

a phenylenediamine derivative represented by the general formula (7):

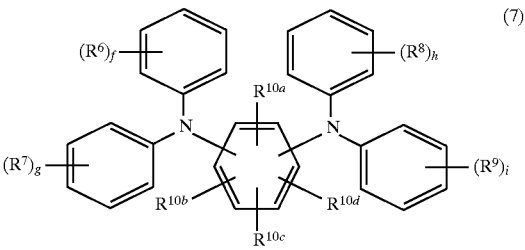

wherein $R^6$, $R^7$, $R^8$ and $R^9$ are the same or different and indicate a hydrogen atom, a halogen atom, an alkyl group which may have a substituent, an alkoxy group which may have a substituent or an aryl group which may have a substituent; $R^{10a}$, $R^{10b}$, $R^{10c}$ and $R^{10d}$ are the same or different and indicate a hydrogen atom, a halogen atom, a cyano group, a nitro group, an alkyl group which may have a substituent, an alkoxy group which may have a substituent or an aryl group which may have a substituent; and f, g, h and i, which indicate substituting numbers of the groups $R^6$, $R^7$, $R^8$ and $R^9$, respectively, and are the same or different and indicate an integer of 1 to 5.

* * * * *